(12) United States Patent
Voelcker et al.

(10) Patent No.: US 10,814,012 B2
(45) Date of Patent: Oct. 27, 2020

(54) COMPOSITIONS AND METHODS FOR ADMINISTERING ANTIBODIES

(71) Applicant: University of South Australia, Adelaide (AU)

(72) Inventors: Nicolas Hans Voelcker, Blackwood (AU); Steven James Peter McInnes, Trinity Gardens (AU); Christopher Travis Turner, Felixstow (AU); Allison June Cowin, St. Georges (AU)

(*) Notice: Subject to any disclaimer, the term of this patent is extended or adjusted under 35 U.S.C. 154(b) by 0 days.

(21) Appl. No.: 15/570,504

(22) PCT Filed: Apr. 29, 2016

(86) PCT No.: PCT/AU2016/050314
§ 371 (c)(1),
(2) Date: Oct. 30, 2017

(87) PCT Pub. No.: WO2016/172769
PCT Pub. Date: Nov. 3, 2016

(65) Prior Publication Data
US 2018/0154019 A1 Jun. 7, 2018

(30) Foreign Application Priority Data
Apr. 29, 2015 (AU) ................................ 2015901533

(51) Int. Cl.
| A61K 47/69 | (2017.01) |
| C07K 16/18 | (2006.01) |
| C07K 16/24 | (2006.01) |
| A61K 9/14 | (2006.01) |
| A61K 47/52 | (2017.01) |
| A61P 17/02 | (2006.01) |
| A61K 47/42 | (2017.01) |
| A61L 15/32 | (2006.01) |
| A61L 15/42 | (2006.01) |
| A61L 15/44 | (2006.01) |
| A61K 39/00 | (2006.01) |

(52) U.S. Cl.
CPC .......... *A61K 47/6923* (2017.08); *A61K 9/143* (2013.01); *A61K 47/42* (2013.01); *A61K 47/52* (2017.08); *A61L 15/32* (2013.01); *A61L 15/425* (2013.01); *A61L 15/44* (2013.01); *A61P 17/02* (2018.01); *C07K 16/18* (2013.01); *C07K 16/241* (2013.01); *A61K 2039/505* (2013.01); *A61L 2300/256* (2013.01); *C07K 2317/34* (2013.01)

(58) Field of Classification Search
CPC combination set(s) only.
See application file for complete search history.

(56) References Cited

U.S. PATENT DOCUMENTS

| 2007/0012574 A1 | 1/2007 | Rauh-Adelmann et al. |
| 2008/0138602 A1* | 6/2008 | Canham ........... A61B 17/06166 428/311.11 |
| 2012/0171292 A1 | 7/2012 | Sailor et al. |

FOREIGN PATENT DOCUMENTS

| WO | WO 03/028643 | 4/2003 |
| WO | WO 2009/009563 | 1/2009 |
| WO | WO 2010/096733 | 8/2010 |

OTHER PUBLICATIONS

Fenollosa et al., "Silicon Particles as Trojan Horses for Potential Cancer Therapy," *J Nanobiotech*, vol. 12:35, 2014.
Gil and Schrum, "Strategies to Stabilize Compact Folding and Minimize Aggregation of Antibody-Based Fragments," *Adv Biosci Biotechnol*, vol. 4:73-84, 2013.
Milgroom et al., "Mesoporous Silica Nanoparticles as a Breast-Cancer Targeting Ultrasound Contrast Agent," *Colloids Surf B Biointerfaces*, vol. 116:652-657, 2014.
Andrew et al., "Sustained Release of a Monoclonal Antibody from Electrochemically Prepared Mesoporous Silicon Oxide," *Advanced Functional Materials*, 20(23): 4168-4174, 2010.
Extended European Search Report dated Aug. 24, 2018 from corresponding European Patent Application No. 16785690.5 (7 pages).
Martinez et al., "Multifunctional to multistage delivery systems: The evolution of nanoparticles for biomedical applications," *Chinese Science Bulletin, Science in China Press*, 57(31): 3961-3971, 2012.
McInnes et al., "Surface engineering of porous silicon to optimise therapeutic antibody loading and release," *Journal of Materials Chemistry*, 3(20): 4123-413, 2015.
Nieto et al., "Ocular silicon distribution and clearance following intravitreal injection of porous silicon microparticles," *Experimental Eye Research*, 116: 161-168, 2013.
Ruzehaji et al., "Attenuation of flightless I improves wound healing and enhances angiogenesis in a murine model of type 1 diabetes," *Diabetologia*, 57(2): 402-412, 2013.
Salonen et al., "Mesoporous silicon microparticles for oral drug delivery: Loading and release of five model drugs," *Journal of Controlled Release*, 108(2): 362-374, 2005.
Streit et al., "Topical application of the tumour necrosis factor-α antibody infliximab improves healing of chronic wounds," *International Wound Journal*, 3(3): 171-179, 2006.

(Continued)

*Primary Examiner* — Hasan S Ahmed
(74) *Attorney, Agent, or Firm* — Klarquist Sparkman, LLP

(57) ABSTRACT

The present invention relates to a drug delivery system and uses thereof. Specifically, a system that can be used to deliver therapeutic proteins, including antibodies, to proteolytic environments is disclosed. In one form of the invention the drug delivery system is a composition which comprises a porous substrate and an antibody bound to the substrate. In one embodiment, the composition comprises nanoporous silicon and can be used to deliver antibodies for the treatment, or for improving the repair, of a wound.

22 Claims, 33 Drawing Sheets

Specification includes a Sequence Listing.

(56) References Cited

OTHER PUBLICATIONS

Tarnuzzer and Schultz, "Biochemical analysis of acute and chronic wound environments," *Wound Repair and Regeneration: Official publication of the wound healing society and the European tissue repair society*, 4(3): 321-325, 1996.
Turner et al., "Delivery of Flightless I Neutralizing Antibody from Porous Silicon Nanoparticles Improves Wound Healing in Diabetic Mice," *Advanced Healthcare Materials*, 6(2): 1600707 (13 pages), 2017.
"Passive Binding Surfaces—Select Surface Guide," ThermoFisher Scientific, https://www.thermofisher.com/us/en/home/products-and-services/promotions/clinical/passive-binding-surfaces-select-surface-guide.html (2 pages).
Anglin et al., "Porous silicon in drug delivery devices and materials," *Advanced Drug Delivery Reviews* 60: 1266-1277, 2008.
Chhablani et al., "Oxidized porous silicon particles covalently grafted with daunorubicin as a sustained intraocular drug delivery system," *Investigative Ophthalmology & Visual Science* 54(2): 1268-1279, 2013.
Pescosolido et al., "Role of Protease-Inhibitors in Ocular Diseases," *Molecules* 19:20557-20569, 2014.

\* cited by examiner

FIG. 1A  FIG. 1B  FIG. 1C
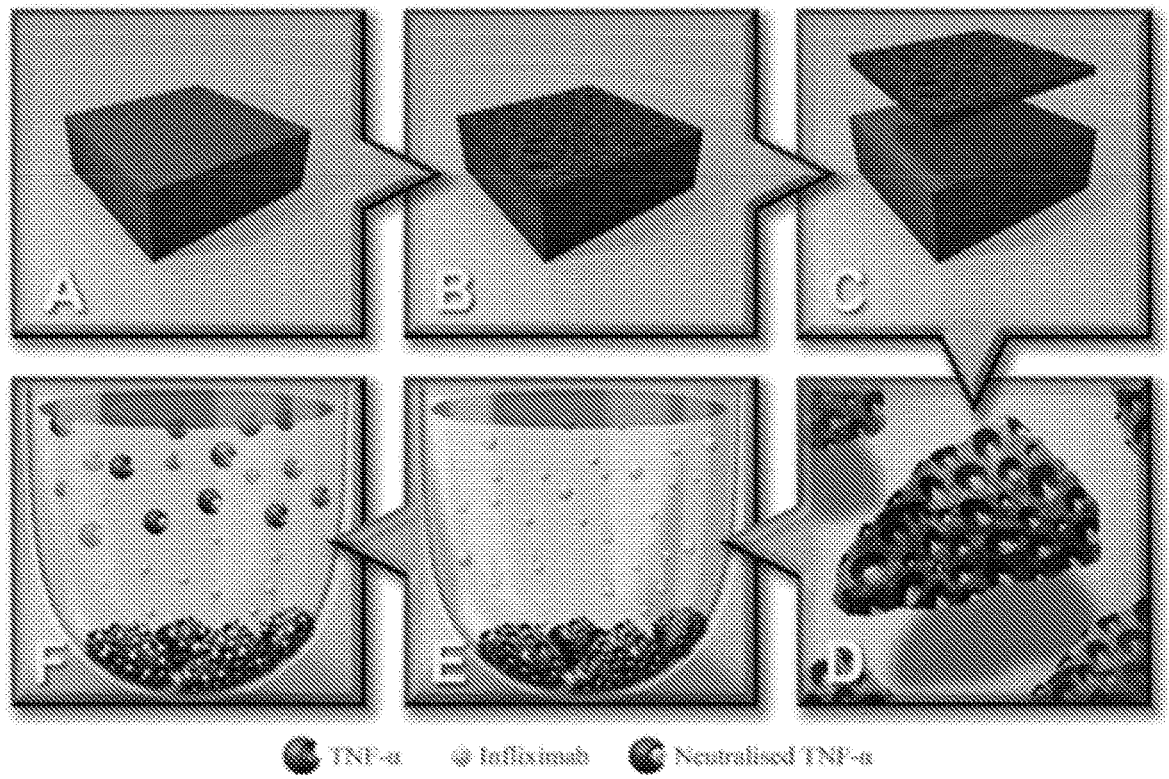
FIG. 1F  FIG. 1E  FIG. 1D
FIG. 2A  FIG. 2B
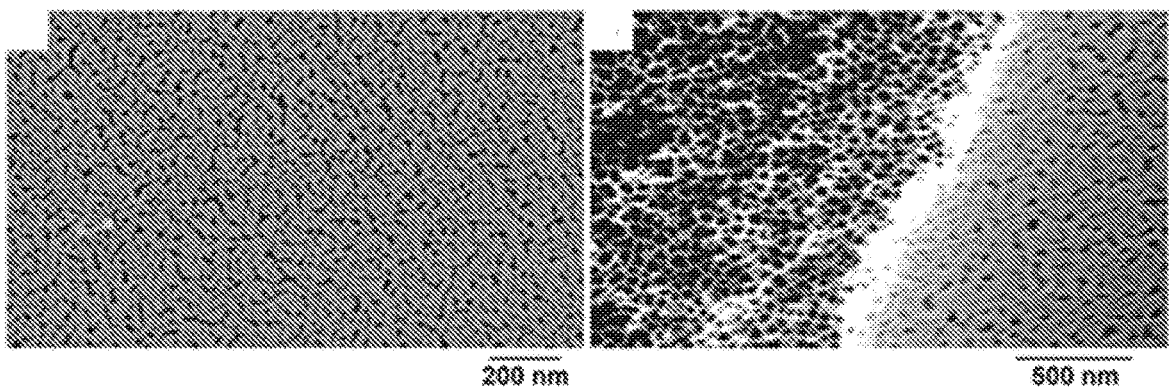

FIG. 5
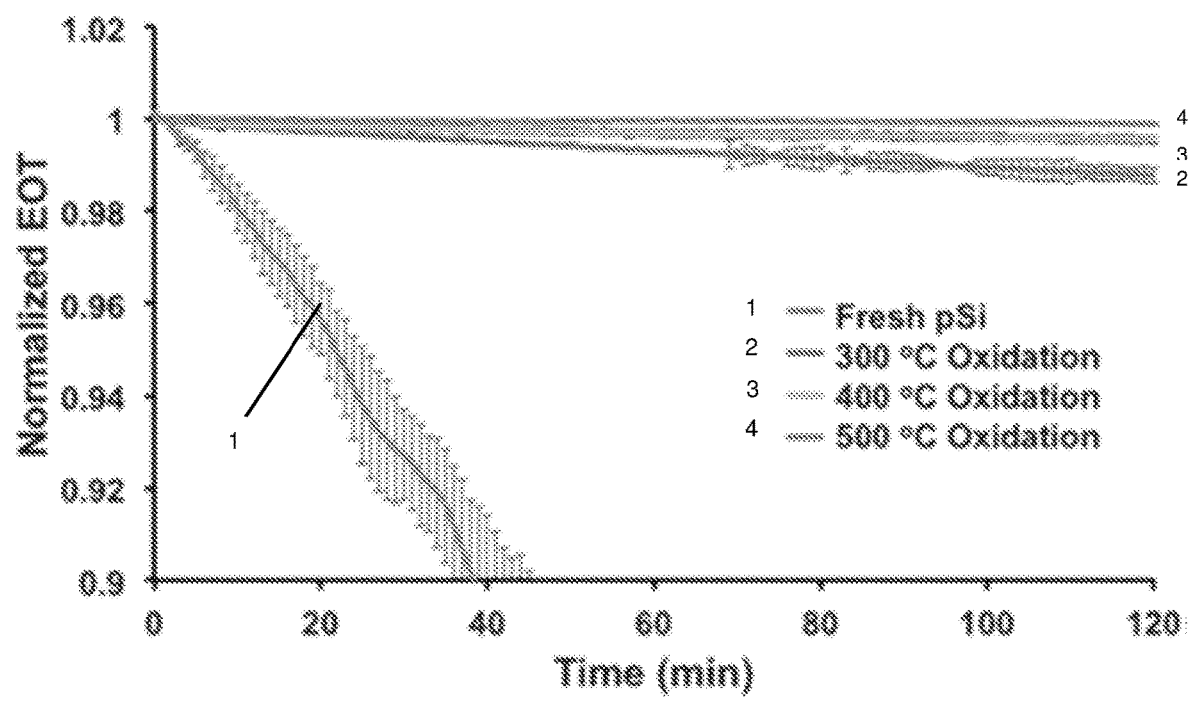
FIG. 6A
FIG. 6B
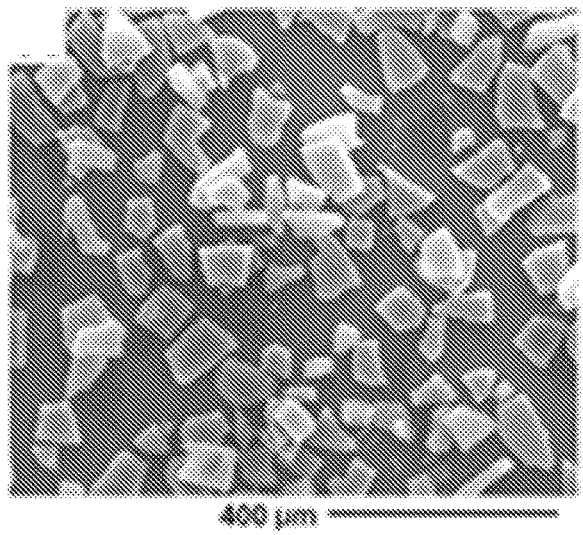
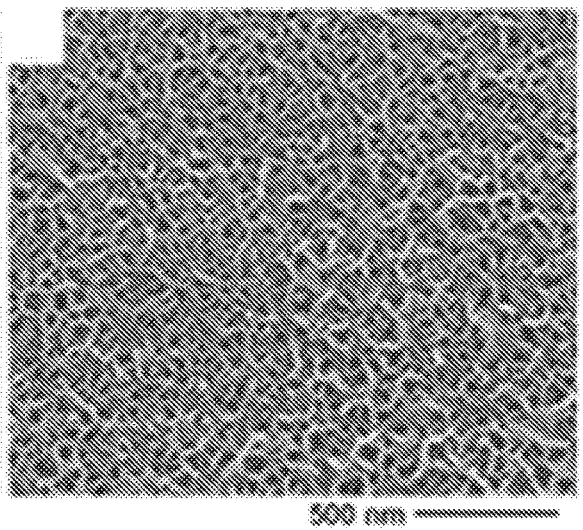

FIG. 7A
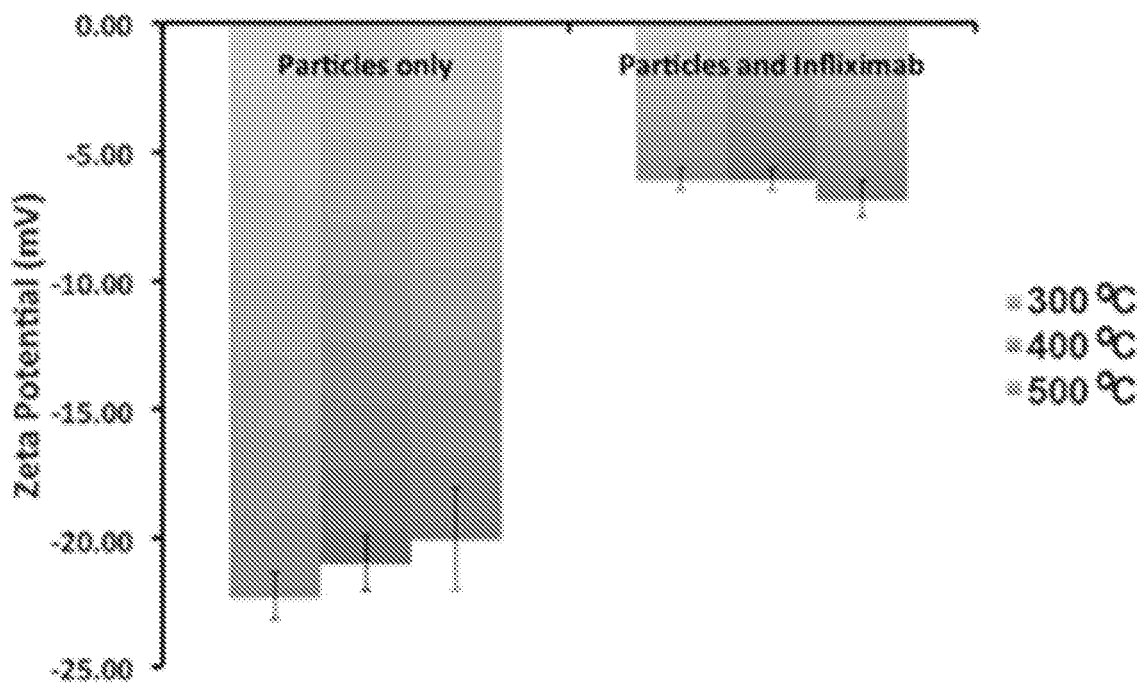
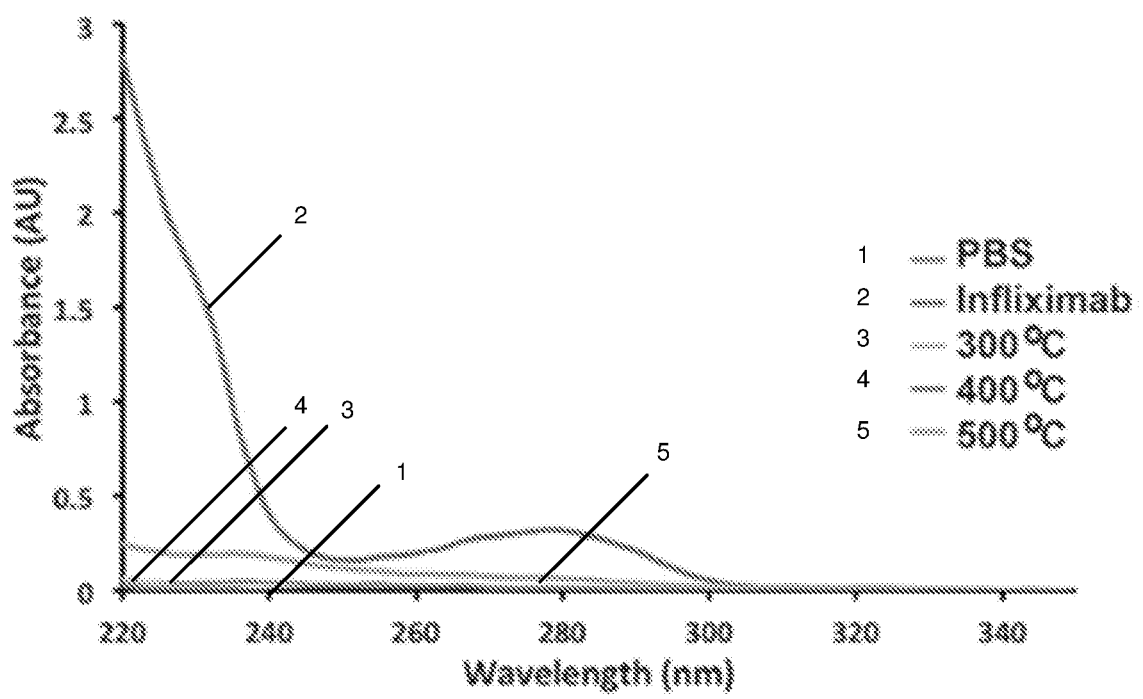
FIG. 7B

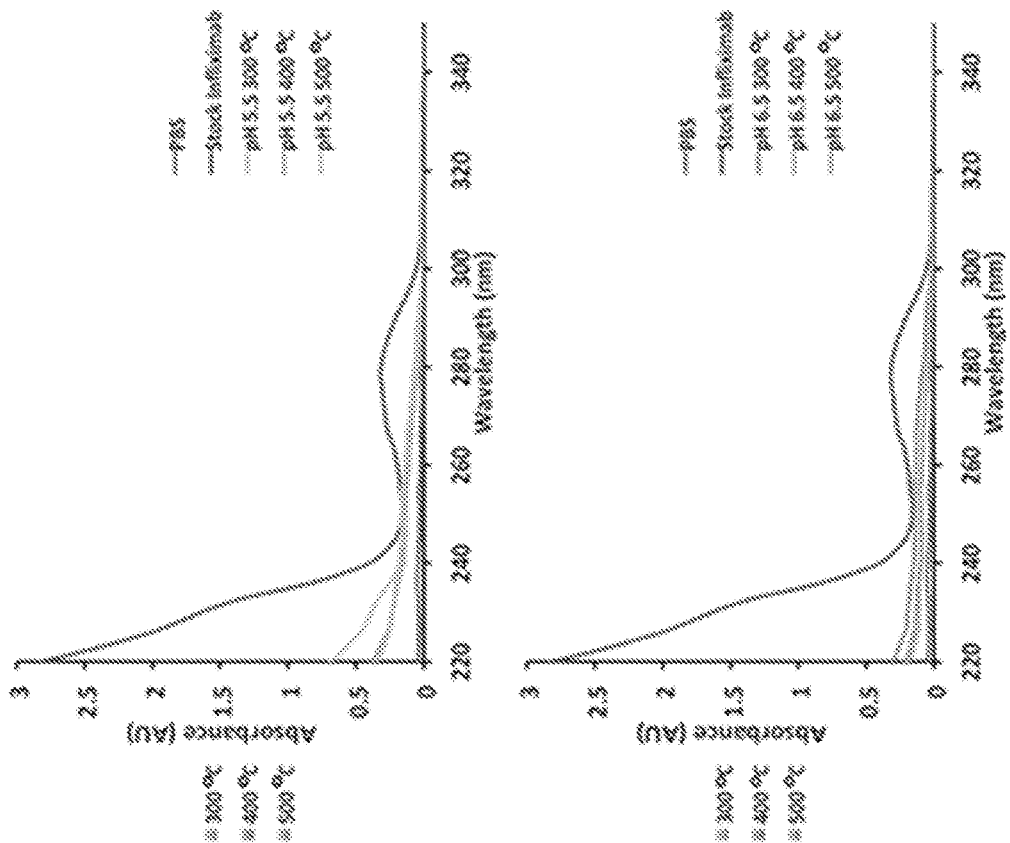
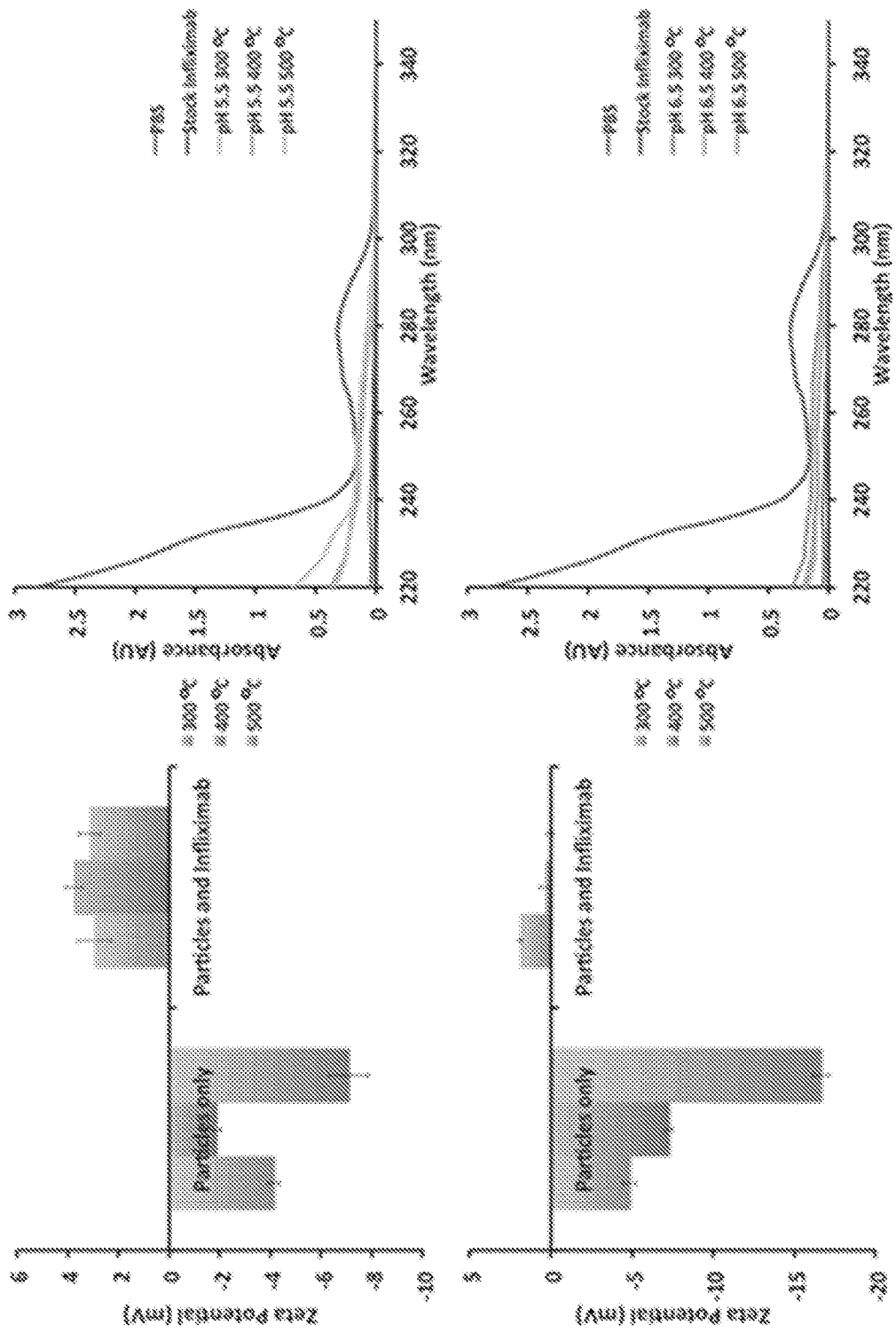
FIG. 8A  FIG. 8B  FIG. 8C  FIG. 8D

FIG. 10A
FIG. 10B
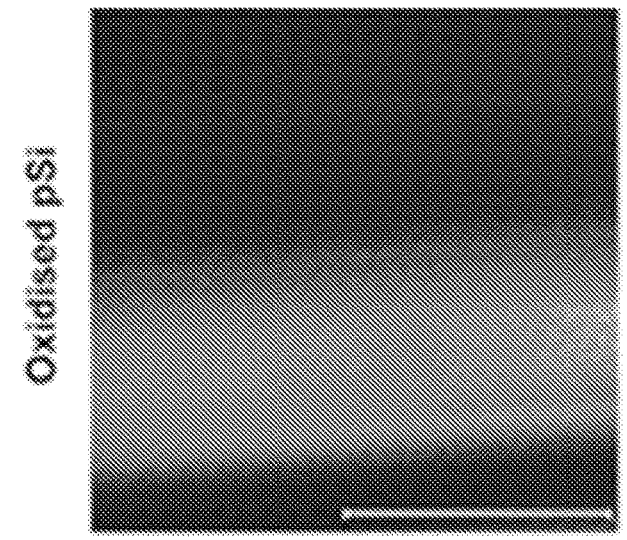
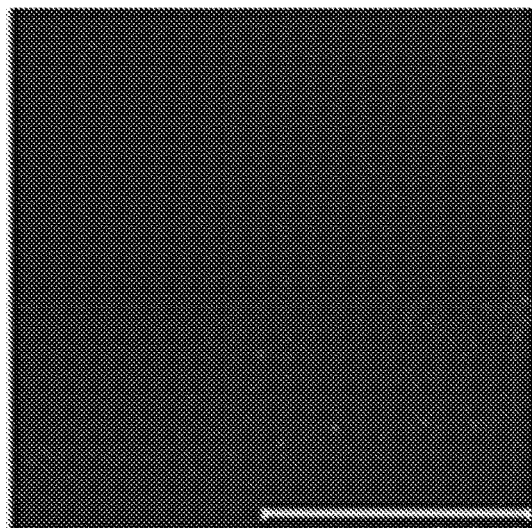
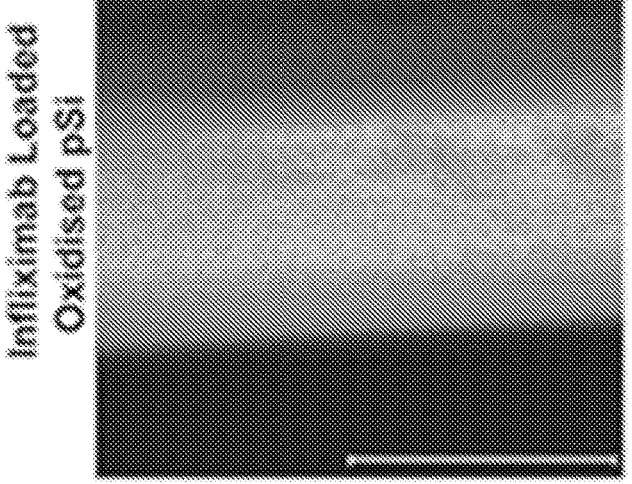
Total Positive Ions
$C_4H_{10}N$ & $C_9H_{12}N$
FIG. 10C
FIG. 10D FIG. 12A  FIG. 12B
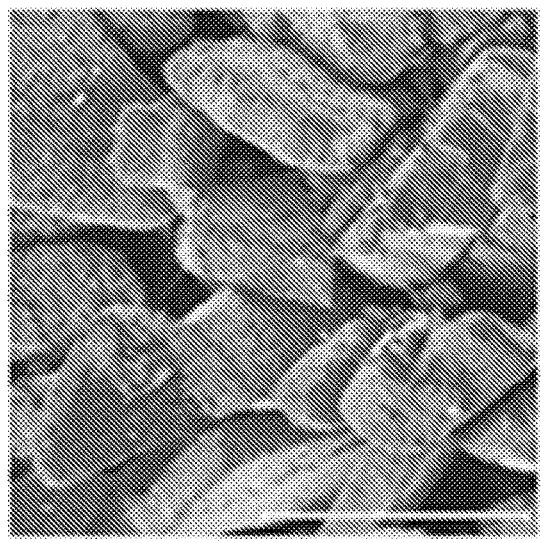
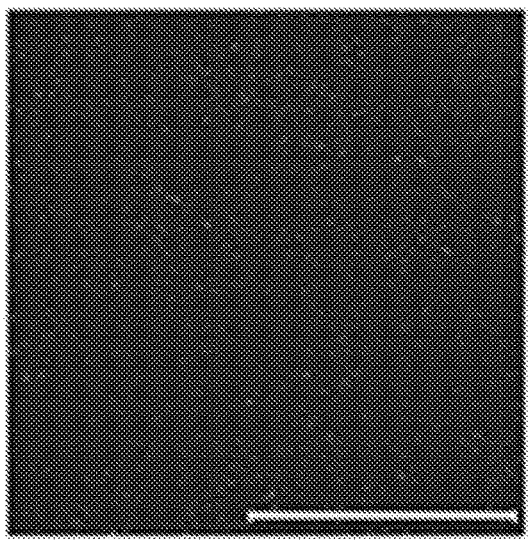
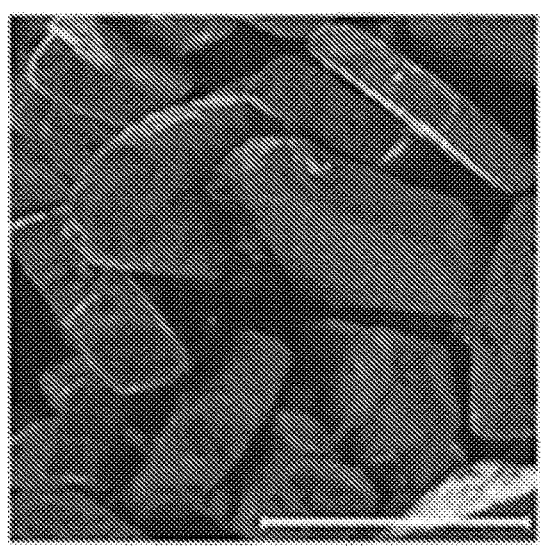
Total Positive Ions  $C_4H_{10}N$ & $C_5H_{12}N$
FIG. 12C  FIG. 12D FIG. 13A
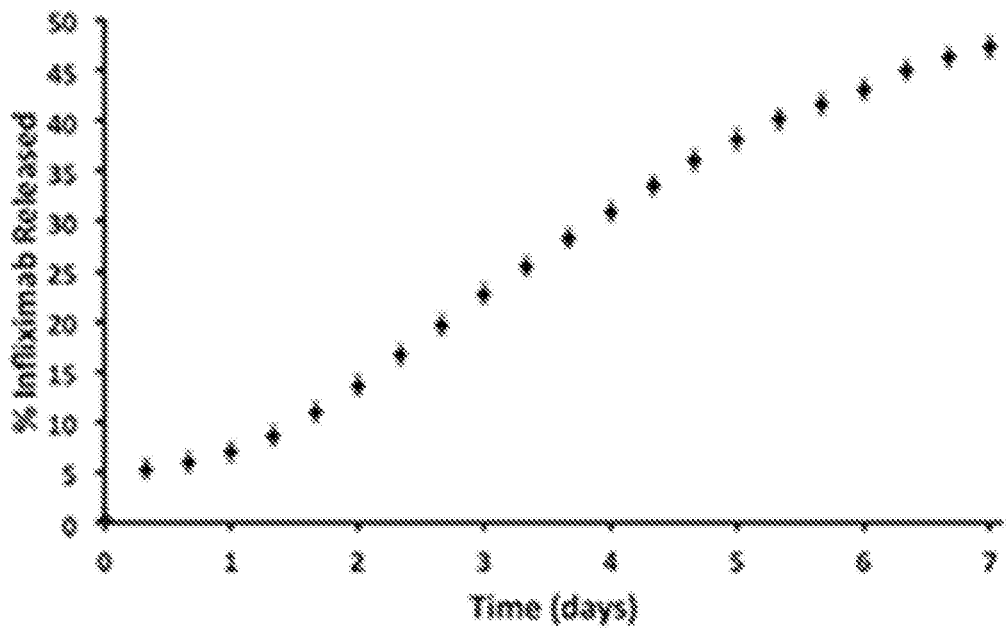
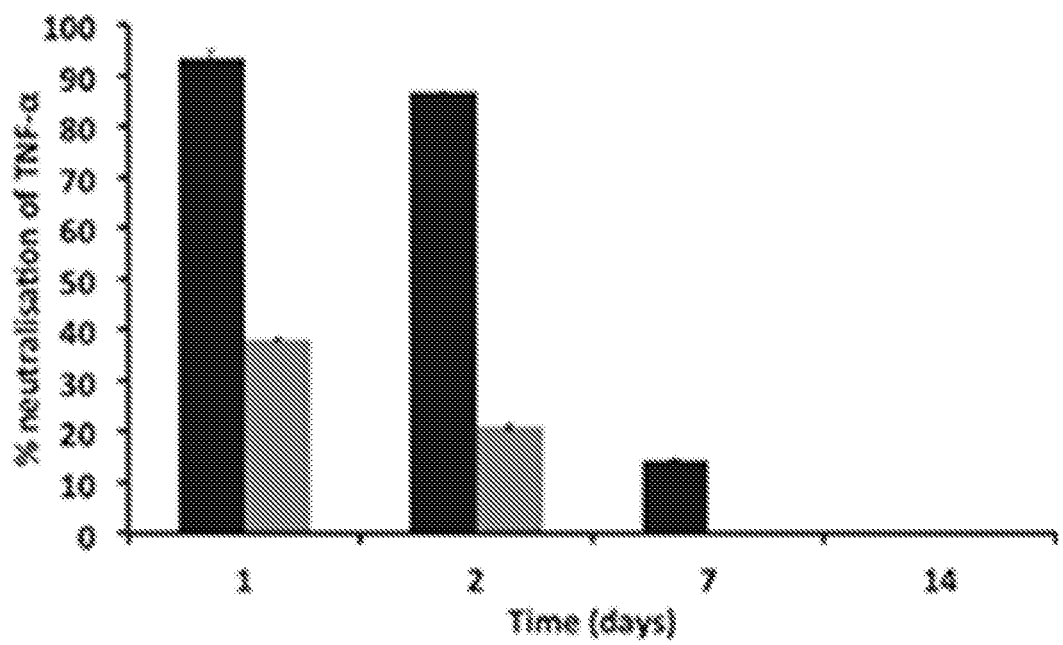
FIG. 13B FIG. 24A
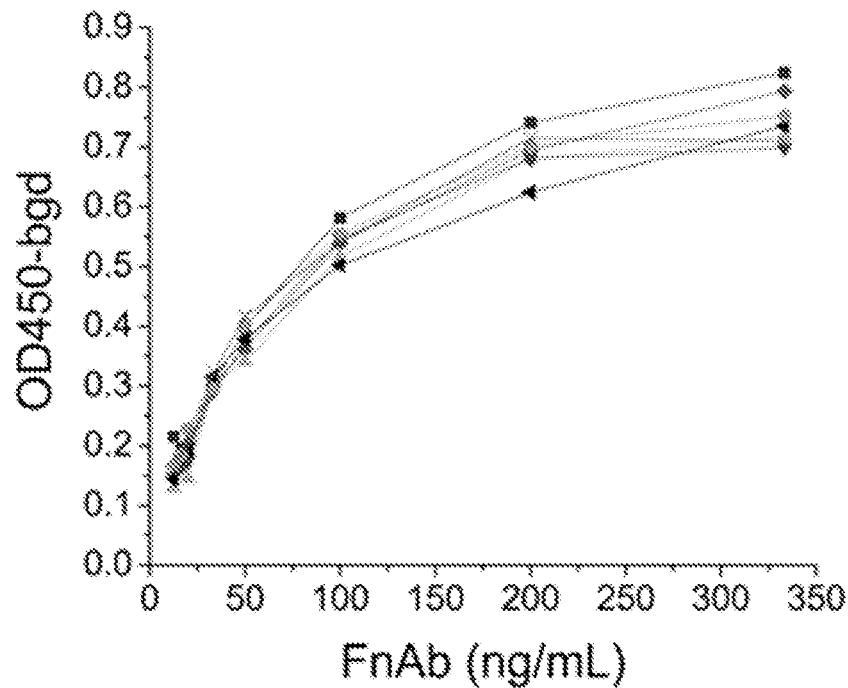
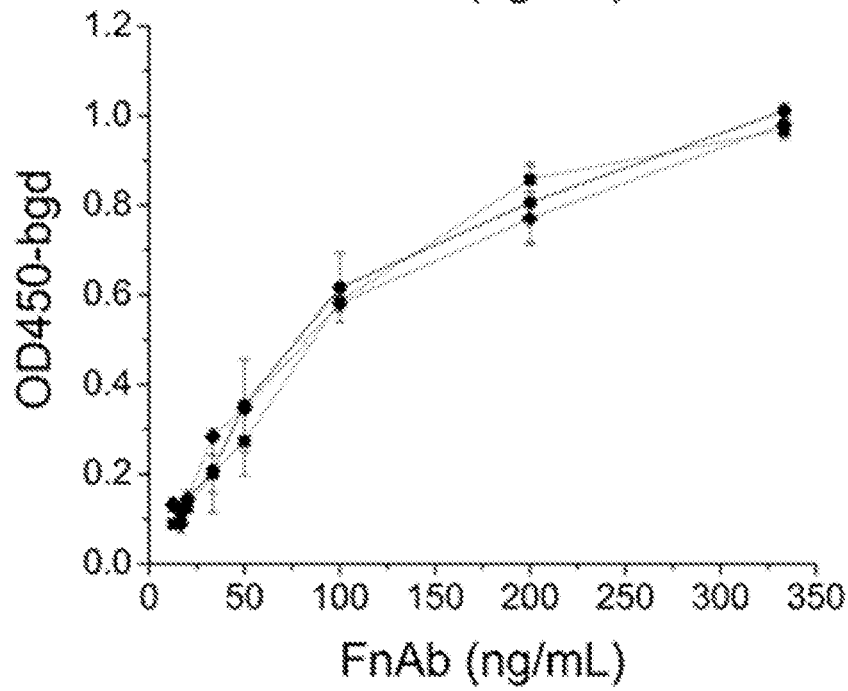
FIG. 24B

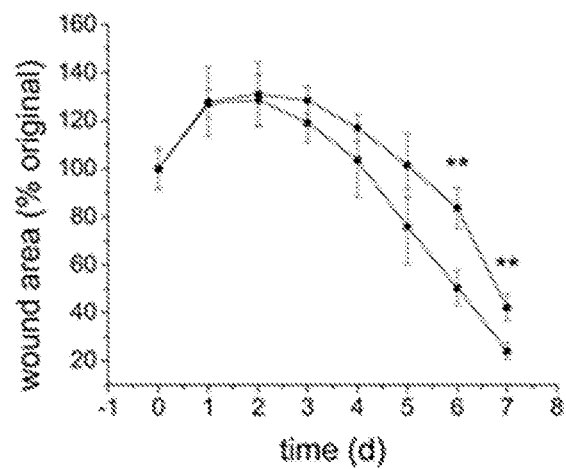 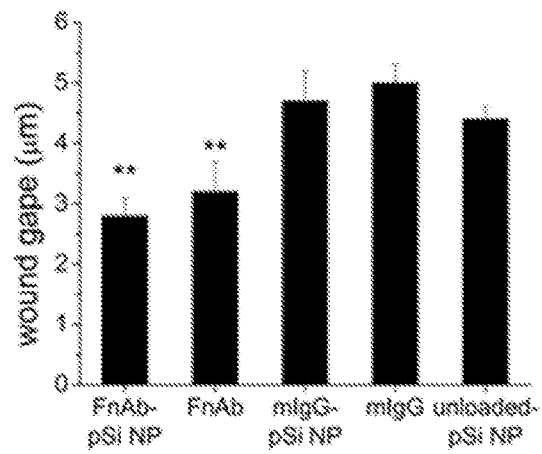
FIG. 26A  FIG. 26B
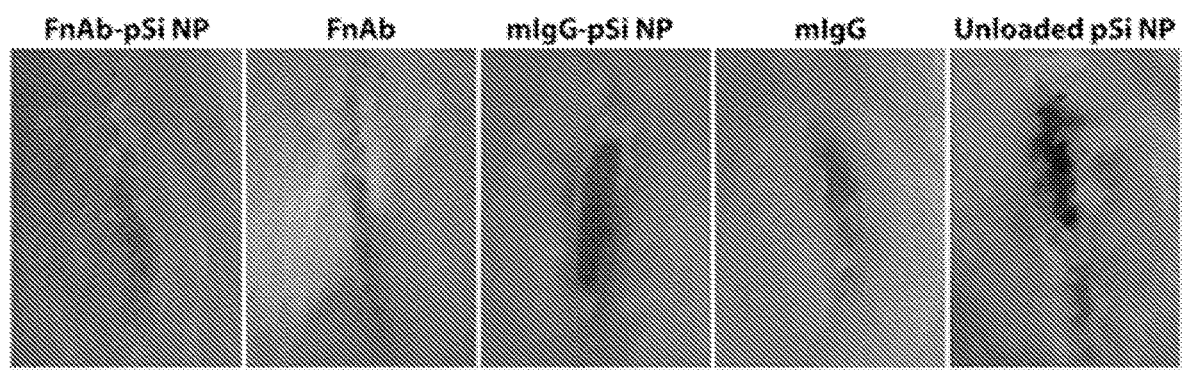
FIG. 26C

COMPOSITIONS AND METHODS FOR ADMINISTERING ANTIBODIES

PRIORITY CLAIM

This is the U.S. National Stage of International Application No. PCT/AU2016/050314, filed Apr. 29, 2016, published in English under PCT Article 21(2), which claims priority from Australian provisional patent application number 2015901533 filed on 29 Apr. 2015, the contents of which are to be taken as incorporated herein by this reference.

FIELD OF THE INVENTION

The present invention relates to compositions formulated to deliver therapeutic antibodies, including compositions that enable delivery of antibodies to, and/or via, proteolytic environments.

BACKGROUND OF THE INVENTION

The use of proteins as therapeutic agents has been increasingly recognized and demonstrated as a relevant treatment modality. Indeed, various protein-based therapeutics have been successful in the clinic with more than 100 proteins being approved for therapeutic use in the USA and Europe.

Antibodies account for a significant portion of protein therapeutics. For example, there are currently more than 30 monoclonal antibodies that have been approved for clinical use and novel molecules are entering clinical trials at an average rate of 50 per year, which is predicted to continue well into the future. Therapeutic antibodies first entered clinical studies in the early 1980s, soon after the description of the original hybridoma technology by Kohler and Milstein. Advances in antibody engineering saw the subsequent production of chimeric, humanized, and human antibodies having lower immunogenicity and the potential to interact more efficiently with effector cells of the immune system. A number of the current generation of antibodies have yielded major commercial and therapeutic successes.

Despite the demonstrated usefulness of a select range of antibodies as treatment agents to date, the identification and development of new therapeutic antibodies, or improving the utility of those currently in the clinic, will need to address inherent barriers to their therapeutic effectiveness. One of those barriers is efficient delivery of the antibody to a subject. For antibodies that have a limited therapeutic window or where biological barriers to delivery exist, high doses of the antibody to the treatment site (locally or systemically) are often required, and this can lead to toxicity or unwanted side effects.

One biological barrier is the use of antibodies for the treatment of diseases, disorders or conditions which are inherently associated with a proteolytic environment. For example, a consistent feature of wounds (such as chronic leg and pressure ulcers) is Ironic inflammation associated with an elevated infiltration of neutrophils. Neutrophils secrete an armament of proteases that participate in various functions at the wound site, including antimicrobial defence. Proteases readily degrade antibodies and so clinical effectiveness of antibodies for the treatment of wounds needs to address the issue of protein degradation in the proteolytic environment of the wound.

Orally administered antibodies are also susceptible to degradation as they pass through the stomach, which is a highly proteolytic environment. Accordingly, systemic oral delivery modalities need to be formulated to allow the antibody to navigate through the stomach and to the ultimate site of action (for example in the lower gastrointestinal tract) without undue degradation prior to delivery to the site of action.

In light of the issues above, there is a need for the development of improved delivery systems for antibodies, particularly those that can protect the antibody from degradation in proteolytic environments.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

The present invention is predicated in part on the development of compositions comprising porous substrates, such as porous silicon, porous polymer, and porous ceramic, as a delivery vehicle for the administration of therapeutic antibodies, including monoclonal antibodies, to and/or via biologically harsh environments.

Accordingly, in a first aspect the present invention provides a method of administering an antibody to, and/or via, a proteolytic environment, the method comprising administering a composition to, and/or via, the proteolytic environment, wherein the composition comprises a porous substrate and the antibody bound to the substrate, and releasing the antibody from the substrate so as to administer the antibody to, and/or via, the proteolytic environment.

In some embodiments, the porous substrate comprises a porous silicon substrate, a porous polymer substrate, or a porous ceramic substrate. In some embodiments, the porous substrate comprises nanoporous silicon or comprises mesoporous silicon.

In some embodiments, the porous silicon substrate comprises a porosified silicon film produced from a crystalline silicon wafer by more than one etching step. In one embodiment, the porosified silicon film is produced from the crystalline silicon wafer by at least two etching steps.

In some embodiments, the porous silicon substrate comprises mesoporous nanoparticles and/or mesoporous microparticles. In one embodiment, the mesoporous nanoparticles and/or mesoporous microparticles are produced by sonication of the porous silicon substrate. In some embodiments, the mesoporous nanoparticles comprise an average size of between about 100 nm to about 1000 nm, and the mesoporous microparticles comprise an average size of between about 1 μm to about 500 μm.

In some embodiments, the porous silicon substrate comprises an average pore size of between about 10 nm to about 40 nm.

In some embodiments, the porous silicon substrate has been thermally oxidized. In some embodiments, the porous silicon substrate has been thermally oxidized at a temperature less than about 600° C. In some embodiments, the porous silicon substrate has been thermally oxidized at a temperature less than about 500° C. In some embodiments, the porous silicon substrate has been thermally oxidized at a temperature of about 400° C.

In some embodiments, the method is used to treat a disease, disorder or condition in a proteolytic environment. In one embodiment, the disease, disorder or condition is selected from the group consisting of a wound, an ocular condition, cancer, or an inflammatory condition. In some embodiments, the wound includes an acute wound, a chronic wound, or a wound in an individual with compromised wound healing capacity. In one embodiment, the acute wound is the result of a penetrative injury, a burn, nerve damage or from elective surgery. In one embodiment, the chronic wound is a diabetic, veneous, arterial, or decubitus, ulcer. In one embodiment, the ocular condition is corneal neovascularization or uveitis. In one embodiment, the inflammatory condition is arthritis, ocular inflammation, chronic pain, rheumatic disease, gastritis, gastroenteritis, inflammatory bowel disease, irritable bowel syndrome, ulcerative colitis, or Crohn's disease.

In some embodiments, the porous substrate protects the antibody from degradation. In some embodiments, the porous substrate protects the antibody from proteolysis and/or hydrolysis.

In some embodiments, the porous substrate protects the antibody from proteolysis.

In some embodiments, the composition further comprises an agent that protects the antibody from proteolysis, reduces protein misfolding, and/or reduces protein denaturation. In one embodiment, the agent comprises a protein. In one embodiment, the protein is present in the composition in an amount from about 1% to about 400% by weight of the antibody present in the composition. In one embodiment, the protein comprises an albumin. In one embodiment, the protein comprises a serum albumin. In one embodiment, the protein is bovine serum albumin. In one embodiment, the bovine serum albumin is present in the composition in an amount from about 10% to about 400% by weight of the antibody present in the composition. In one embodiment, the agent comprises a peptide, an oligopeptide and/or a polypeptide.

In some embodiments, the antibody comprises a monoclonal antibody or a polyclonal antibody. In some embodiments, the antibody comprises a therapeutic antibody. In some embodiments, the antibody comprises a monoclonal antibody to Flightless I. In some embodiments, the antibody comprises a monoclonal antibody to TNF-α. In one embodiment, the monoclonal antibody comprises Infliximab.

In some embodiments, the porous substrate is a porous silicon substrate which is biodegradable vivo.

In some embodiments, the administering comprises exposing the proteolytic environment to a dressing or bandage that comprises a composition comprising a porous substrate and an antibody. In some embodiments, the administering comprises topical administration of the composition to the proteolytic environment. In some embodiments, the administering comprises systemic administration of the composition. In one embodiment, the systemic administration comprises oral administration of the composition.

In a second aspect, the present invention provides a method of administering an antibody to a wound, the method composing administering a composition to the wound, wherein the composition comprises a porous silicon substrate and the antibody bound to the substrate, and releasing the antibody from the substrate so as to administer the antibody to the wound.

In a third aspect, the present invention provides a method of treating a wound, the method comprising administering a composition to the wound, wherein the composition comprises a porous silicon substrate and an antibody bound to the substrate, and releasing the antibody from the substrate so as to administer the antibody to the wound, thereby treating the wound.

In a fourth aspect, the present invention provides a method of improving repair of a wound, the method comprising administering a composition to the wound, wherein the composition comprises a porous silicon substrate and an antibody bound to the substrate, and releasing the antibody from the substrate so as to administer the antibody to the wound, thereby improving repair of the wound.

In a fifth aspect, the present invention provides a composition for protecting an antibody from degradation in a proteolytic environment, the composition comprising a porous substrate and an antibody bound to the substrate.

In some embodiments of the fifth aspect, the porous substrate comprises a porous silicon substrate, a porous polymer substrate, or a porous ceramic substrate. In some embodiments, the porous substrate comprises nanoporous silicon or comprises mesoporous silicon.

In some embodiments of the fifth aspect, the porous silicon substrate comprises a porosified silicon film produced from a crystalline silicon wafer by more than one etching step. In one embodiment, the porosified silicon film is produced from the crystalline silicon wafer by at least two etching steps.

In some embodiments of the fifth aspect, the porous silicon substrate comprises mesoporous nanoparticles and/or mesoporous microparticles. In one embodiment, the mesoporous nanoparticles and/or mesoporous microparticles are produced by sonication of the porous silicon substrate. In some embodiments, the mesoporous nanoparticles comprise an average size of between about 100 nm to about 1000 nm, and the mesoporous microparticles comprise an average size of between about 1 μm to about 500 μm.

In some embodiments of the fifth aspect, the porous silicon substrate comprises an average pore size of between about 10 nm to about 40 nm.

In some embodiments of the fifth aspect, the porous silicon substrate has been thermally oxidized. In some embodiments of the fifth aspect, the porous silicon substrate has been thermally oxidized at a temperature less than about 600° C. In some embodiments of the fifth aspect, the porous silicon substrate has been thermally oxidized at a temperature less than about 500° C. In some embodiments, the porous silicon substrate has been thermally oxidized at a temperature of about 400° C.

In some embodiments of the fifth aspect, the porous substrate comprises a porous silicon substrate that protects the antibody from proteolysis.

In some embodiments of the fifth aspect, the composition further comprises an agent that protects the antibody from proteolysis, reduces protein misfolding, and/or reduces protein denaturation. In one embodiment, the agent comprises a protein. In one embodiment, the protein is present in the composition in an amount from about 1% to about 400% by weight of the antibody present in the composition. In one embodiment, the protein comprises an albumin. In one embodiment, the protein comprises a serum albumin. In one embodiment, the protein is bovine serum albumin. In one embodiment, the bovine serum albumin is present in the composition in an amount from about 10% to about 400% by weight of the antibody present in the composition. In one embodiment, the agent comprises a peptide, an oligopeptide and/or a polypeptide.

In some embodiments of the fifth aspect, the antibody comprises a monoclonal antibody or a polyclonal antibody. In some embodiments, the antibody comprises a monoclonal antibody to Flightless I. In some embodiments, the antibody comprises a monoclonal antibody to TNF-α. In one embodiment, the monoclonal antibody comprises Infliximab.

In some embodiments of the fifth aspect, the porous silicon substrate is biodegradable in vivo.

In some embodiments of the fifth aspect, the composition comprises a wound healing composition. In some embodiments, the composition is part of a dressing or bandage. In some embodiments, the composition is a topical composition, an oral composition or an ocular composition.

In a sixth aspect, the present invention provides a composition for protecting an antibody from degradation in a proteolytic environment, the composition comprising a porous silicon substrate comprising mesoporous nanoparticles and/or mesoporous microparticles and an antibody bound to the substrate.

In a seventh aspect, the present invention provides a composition for protecting an antibody from degradation in a proteolytic environment, wherein the composition comprises a porous silicon substrate and an antibody bound to the substrate.

In an eighth aspect, the present invention provides a composition for protecting an antibody from degradation in a proteolytic environment, wherein the composition comprises a porous silicon substrate comprising mesoporous nanoparticles and/or mesoporous microparticles and an antibody bound to the substrate.

In a ninth aspect, the present invention provides a composition for protecting an antibody from degradation in a proteolytic environment, wherein the composition comprises a porous silicon substrate, and wherein the porous substrate comprises a porosified silicon film produced from a crystalline silicon wafer by more than one etching step.

In a tenth aspect, the present invention provides a composition for protecting an antibody in a proteolytic environment, wherein the composition comprises a porous silicon substrate and an antibody bound to the substrate, the porous silicon substrate comprising mesoporous nanoparticles and/or mesoporous microparticles, and wherein the mesoporous nanoparticles and/or mesoporous microparticles are produced by sonication of a porosified silicon film produced from a crystalline silicon wafer by more than one etching step.

In an eleventh aspect, the present invention provides a wound healing composition comprising a porous silicon substrate and an antibody bound to the substrate.

In a twelfth aspect, the present invention provides an oral pharmaceutical composition comprising a porous silicon substrate and an antibody bound to the substrate.

In a thirteenth aspect, the present invention provides a method of using a composition of any one of the fifth to twelfth aspects of the invention to treat a disease, disorder or condition in, and/or via, a proteolytic environment.

In a fourteenth aspect, the present invention provides an antibody loaded onto a porous silicon substrate for use in delivering the antibody to, and/or via, a proteolytic environment.

In a fifteenth aspect, the present invention provides a dressing or bandage comprising a composition of the fifth to twelfth aspects of the invention.

In a sixteenth aspect, the present invention provides a method of preparing a porous silicon substrate, the method comprising the steps of:
(i) providing a crystalline silicon wafer;
(ii) porosifying the crystalline silicon wafer to produce a porosified silicon film on a surface of the crystalline silicon wafer; and
(iii) removing the porosified silicon film from the crystalline silicon wafer by more than one etching step, thereby preparing the porous silicon substrate.

In some embodiments of the sixteenth aspect, the porosified silicon film is removed from the crystalline silicon wafer by at least two etching steps.

In some embodiments of the sixteenth aspect, the porous silicon substrate has an average pore size of between about 10 nm to about 40 nm.

In some embodiments of the sixteenth aspect, the method further includes the step of (iv) oxidizing the porisified silicon film. In some embodiments of the sixteenth aspect, the method further includes the step of (iv) oxidizing the porisified silicon film at about 400° C. In some embodiments, prior to step (iv), the porisified silicon film is subdivided into discrete particles.

In some embodiments of the sixteenth aspect, the porisified silicon film is subdivided into discrete particles by sonification of the porisified silicon film. In one embodiment the particles are in the form of mesoporous nanoparticles and/or mesoporous microparticles. In one embodiment the mesoporous nanoparticles comprise an average size of between about 100 nm to about 1000 nm, and the mesoporous microparticles comprise an average size of between about 1 µm to about 500 µm. In some embodiments, the mesoporous nanoparticles comprise an average size of between about 100 nm to about 250 nm, and the mesoporous microparticles comprise an average size of between about 20 µm to about 85 µm.

In a seventeenth aspect, the present invention provides a porous silicon substrate prepared by the method of the sixteenth aspect of the invention.

In an eighteenth aspect, the present invention provides mesoporous nanoparticles or mesoporous microparticles prepared by the method of the sixteenth aspect of the invention.

BRIEF DESCRIPTION OF THE FIGURES

For a further understanding of the aspects and advantages of the present invention, reference should be made to the following detailed description, taken in conjunction with the accompanying figures.

FIG. 1—shows the general scheme for the studies demonstrating that an antibody (in this embodiment Infliximab) released from porous silicon (pSi) microparticles (MPs) remained active and was able to neutralise TNF-α, providing an improved therapeutic delivery system for the treatment of chronic wounds and ocular conditions such as uveitis. Panel (A) shows a crystalline silicon wafer prior to (B) electrochemical anodization to produce a pSi film. The film is then removed from the crystalline substrate via an electropolishing etch (C). The resulting free-standing pSi film is sonicated to generate pSi MPs which are subsequently oxidized at 400° C. (D) and then loaded with the therapeutic antibody Infliximab (E). The Infliximab is released from the pSi and neutralizes TNF-α (F).

FIG. 2—shows in panel (A) SEM of the microporous layer remaining above pSi etches if not removed via techniques such as NaOH dissolution or a first sacrificial etching step. (B) A defect site in the films shown in (A) showing both the microporous layer and the desired porous layer beneath it.

FIG. 5—shows degradation profiles over 120 min of freshly etched pSi films as well as pSi films oxidized at 300° C., 400° C. and 500° C., as determined by IRS measurements in PBS buffer at pH 7.2 at 25° C. (n=3).

FIG. 6—shows in panel (A) a SEM micrograph showing the size distribution of the pSi MPs and (B) a higher resolution SEM micrograph showing mesopores of the pSi MPs.

FIG. 7—shows in panel (A) change in zeta potential upon binding of Infliximab to pSi MPs in pH 7.4 buffer for different pSi MP oxidation conditions (300° C.—left columns, 400° C.—middle columns, and 500° C.—right columns) (n=3) and (B) UV-Vis monitoring of the Infliximab in supernatant during the binding experiment in panel (A) at pH 7.4.

FIG. 8—shows zeta potential measurements of the Infliximab binding at 300° C. (left column), 400° C. (middle column) and 500° C. (right column) oxidized pSi at pH 5.5 (A). (B) Corresponding UV-Vis monitoring of the Infliximab in solution during the zeta-potential binding experiment in panel (A). (C) zeta potential measurements of the Infliximab binding at to 300° C. (left column), 400° C. (middle column) and 500° C. (right column) oxidized pSi at pH 6.5 for different oxidation conditions (n=3). (D) UV-Vis monitoring of the Infliximab in solution during the zeta-potential binding experiment in panel (C) at pH 6.5 (n=3).

FIG. 10—shows ToF-SIMS images (200 μm×200 μm) for the total positive ions (panels A and C) and for the positive ion fragments $C_4H_{10}N^+$ (m/z 72.081) and $C_5H_{12}N^+$ (m/z 86.096) (panels B and D) characteristic of the amino acids valine and leucine/isoleucine acquired on the cross-section of oxidized pSi (400° C.) and Infliximab-loaded oxidized pSi films. Scale bar on the images=100 μm. To help aid analysis in imaging mode, pSi films were etched for 20 min to produce a pSi layer of approximately 80 μm thickness.

FIG. 12—shows ToF-SIMS images (200 μm×200 μm) for the total positive ions (panels A and C) and for the positive ion fragments $C_4H_{10}N^+$ (m/z 72.081) and $C_5H_{12}N^+$ (m/z 86.096) (panels B and D) characteristic of the amino acids valine and leucine/isoleucine acquired on the oxidized pSi (400° C.) and Infliximab-loaded pSi MPs. Scale bar on the images=100 μm.

FIG. 13—shows in panel (A) FITC tracking of Infliximab released at 25° C. and pH 7.4 from oxidized pSi MPs (400° C.) over a 7 day period. (B) ELISA detection of TNF-α. Supernatant containing Infliximab released from pSi was incubated with human TNF-α for 10 minutes at 37° C. Non-neutralized TNF-α was then detected by ELISA. Supernatant was collected from 400° C. oxidized pSi MPs loaded with Infliximab and incubated at 25° C. over a 14 day period (black bars). Fresh Infliximab (i.e. not associated with pSi MPs) was also incubated in PBS (grey bars). Data at each time point are presented as the % inhibition of TNF-α by Infliximab. The assay was performed in triplicate and presented as mean+/− one standard deviation.

FIG. 24—shows the effect of pSi breakdown products on FnAb functionality. An ELISA was used to detect functional FnAb following incubation in sodium metasilicate (A) and buffer containing degraded pSi MPs (B). In panel (A), FnAb vias incubated with sodium metasilicate at 0 μg/mL (♦), 0.13 μg/mL (×), 1.3 μg/mL (●), 13 μg/mL (◄) 130 μg/mL (■) 650 μg/mL (▲) and 1300 μg/mL (▼). In panel (B), FnAb was incubated with supernatant containing PBS alone (●, solid line), pSi MPs incubated in PBS for 20 d at 25° C. (♦, dashed line) and pSi MPs incubated in PBS for 27 d at 25° C. (■, dotted line). Data presented as signal at 450 nm minus background. In panel (B), data is presented as mean+/− one standard deviation (n=3).

FIG. 26—shows macroscopic analysis of incisional wound trial in healthy wild-type mice. Wounds were treated with intradermal injections of FnAb-pSi NPs (■) or mIgG-pSi NPs (●) at the time of injury (A). (A) Wound gape calculated as a % of original wound area. Each wound was treated with the equivalent of 50 μg of FnAb or mIgG. (B) At day 7, wound gape was also determined in mice treated with FnAb alone, mIgG alone and unloaded pSi NPs. (C) Images of the incisional wounds at day 7. Each treatment group contained six mice, with two wounds per mouse. Images (C) were representative of each treatment group. *P<0.05. **P<0.005.

DETAILED DESCRIPTION OF THE INVENTION

Figure 3:
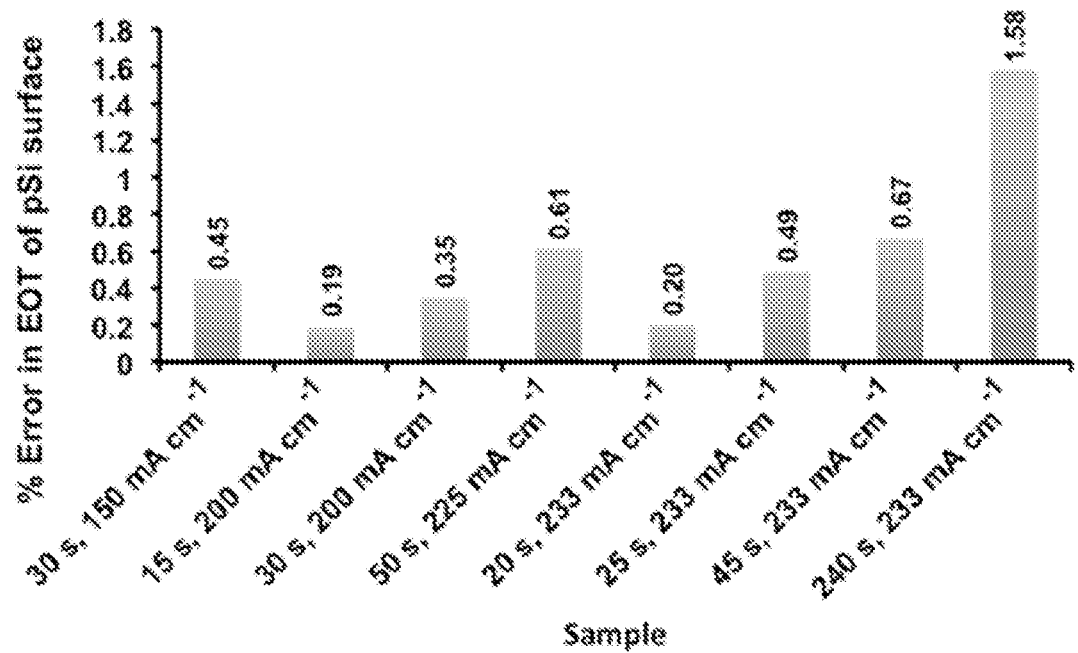
FIG. 3—shows effective optical thickness (EOT) readings of the different etching conditions (time and current) (n=20) as a measure of degradation kinetic of the material.

Nucleotide sequences are referred to herein by a sequence identifier number (SEQ ID NO:). A summary of the sequence identifiers is provided in Table 1. A sequence listing is also provided. The Sequence Listing is submitted as an ASCII text file, created on Oct. 30, 2017, 53.0 KB, which is incorporated by reference herein.

TABLE 1

Summary of Sequence Identifiers

| Sequence Identifier | Sequence |
| --- | --- |
| SEQ ID NO: 1 | Human Flightless I mRNA sequence - variant 1 (NM_002018.3) |
| SEQ ID NO: 2 | Human Flightless I amino acid sequence - variant 1 (NP_002009.1) |
| SEQ ID NO: 3 | Human Flightless I mRNA sequence -variant 2 (NM_001256264.1) |
| SEQ ID NO: 4 | Human Flightless I amino acid sequence - variant 2 (NP_001243193.1) |
| SEQ ID NO: 5 | Human Flightless I mRNA sequence - variant 3 (NM_001256265.1) |
| SEQ ID NO: 6 | Human Flightless I amino acid sequence - variant 3 (NP_001243194.1) |
| SEQ ID NO: 7 | Human TNF-α mRNA sequence (NM_000594.3) |
| SEQ ID NO: 8 | Human TNF-α amino acid sequence (NP_000585.2) |
| SEQ ID NO: 9 | Flightless I peptide sequence |

The present invention is predicated in part on the development and use of porous substrates, such as porous silicon, as a delivery vehicle for the administration of antibodies, including therapeutic monoclonal antibodies, to and/or via biologically harsh environments, including proteolytic environments.

Certain disclosed embodiments have one or more combinations of advantages. For example, some of the advantages of the embodiments disclosed herein include one or more of the following: a drug delivery system with improved characteristics; an improved composition for therapeutic use; a biodegradable drug delivery system; a drug delivery vehicle with low toxicity; a delivery system that can be used to deliver therapeutic proteins, including antibodies, to proteolytic environments; a delivery system with reduced side effects; a drug delivery system with improved efficacy; a delivery system that is inorganic and/or sterilisable; a delivery system that is substantially biologically inert; a delivery system that degrades into a non-toxic product; a delivery system that utilises the porous nature of the carrier to load increased amounts of a therapeutic protein as compared to a non-porous carrier; a delivery system with a high loading capacity; a system that allows delivery of large molecules, such as antibodies; a delivery system that is amenable to imaging in vivo; an to provide reduced dosages of existing drugs; to address one or more problems in the art; to provide one or more advantages in the art; and/or to provide a useful commercial choice. Other advantages of certain embodiments are disclosed herein.

In a first aspect the present invention provides a method of administering an antibody to, and/or via, a proteolytic environment, the method comprising administering a composition to, and/or via, the proteolytic environment, wherein the composition comprises a porous substrate and the antibody bound to the substrate, and releasing the antibody from the substrate so as to administer the antibody to, and/or via, the proteolytic environment.

A proteolytic environment in the context of the present invention is a site having enzymes that break down proteins into smaller polypeptides, and even to discrete amino acids. The process by which these enzymes degrade proteins is hydrolysis of the peptide bond between amino acids in the protein. Proteolytic enzymes are typically referred to as proteases of which there are six broad groups, namely serine proteases, threonine proteases, cysteine proteases, aspartate proteases, glutamic acid proteases, and metalloproteases.

Examples of proteolytic environments include those associated with wounds and the wound healing process. A wound can be described as a defect or a break in the skin, resulting from physical or thermal damage or as a result of the presence of an underlying medical or physiological condition.

Based on the nature of the repair process, wounds can be broadly classified as acute wounds (such as those resulting from penetrative injuries, burns, nerve damage and wounds resulting from elective surgery), chronic wounds (such as diabetic, venous, arterial and decubitus ulceration), or wounds in individuals with compromized wound healing capacity, such as the elderly.

Acute wounds are usually tissue injuries that heal completely, with minimal scarring, within the expected time frame (usually 8-12 weeks). The primary causes of acute wounds include mechanical injuries due to external factors such as abrasions and tears which are caused by frictional contact between the skin and hard surfaces. Mechanical injuries also include penetrating wounds caused by knives and gun shots and surgical wounds caused by surgical incisions, for example to remove tumours. Another category of acute wounds include burns and chemical injuries, which arise from a variety of sources such as radiation, electricity, corrosive chemicals and thermal sources. The temperature of the source and the exposure time influence the degree of a thermal burn. Burns will normally require specialist care because of the associated trauma.

Chronic wounds arise from tissue injuries that heal slowly (i.e. those that have not healed beyond 12 weeks) and often reoccur. Such wounds fail to heal due to repeated tissue insults or underlying physiological conditions, such as diabetes and malignancies, persistent infections, poor primary treatment and other patient related factors. These result in a disruption of the orderly sequence of events during the wound healing process.

Wounds have also been classified based on the number of skin layers and area of skin affected. Injury that affects the epidermal skin surface alone is referred to as a superficial wound, whilst injury involving both the epidermis and the deeper dermal layers, including the blood vessels, sweat glands and hair follicles is referred to as partial thickness wound. Full thickness wounds occur when the underlying subcutaneous fat or deeper tissues are damaged in addition to the epidermis and dermal layers.

The wound healing process is complex and dynamic and that results in the restoration of cellular structures and tissue layers. Generally, the wound healing process can be divided into three distinct phases: the inflammatory phase, the proliferative phase, and the remodelling phase. Each of these phases involves a complex and coordinated series of events that includes chemotaxis, phagocytosis, neo-collagenosis, collagen degradation, and collagen remodelling. The recruitment of a variety of specialized cell types to the site of a wound is also a critical part of the process of wound healing. This process requires extracellular matrix and basement membrane deposition, angiogenesis, selective protease activity and re-epithelialisation.

A consistent feature of wounds, including arterial, venous and decubitus ulcers, is chronic inflammation that is associated with increased neutrophil infiltration. Although neutrophils have important positive roles in host defence and debridement of damaged tissues, these cells and their proteases have been implicated in mediating much of the tissue damage associated with chronic inflammatory diseases such as rheumatoid arthritis. It has therefore been proposed that an over exuberant neutrophil response may participate to a significant extent in the pathophysiology of chronic wounds (see Yager D R and Nwomeh B C, 1999, *Wound Rep. Reg.,* 7: 433-441). The presence of neutrophil proteases therefore contributes significantly to the proteolytic environment of the wound. However, the composition of the present invention assists with protection of the antibody from degradation in proteolytic environments such as wounds.

Another example of a proteolytic environment is the digestive tract. Orally administered therapeutic agents pass through the highly proteolytic environment of the stomach as a precursor to their systemic distribution through the body. Protein therapeutics such as antibodies are therefore particularly susceptible to degradation when administered orally and indeed therapeutically effective amounts of the antibody may not ultimately make it to their intended destination. However, the composition of the present invention may assist with protection of the antibody from degradation as it passes via the proteolytic environment of the stomach. For example, the composition of the present invention may assist with protection of the antibody from degradation as it passes via the proteolytic environment of the stomach to the intended destination of the gastrointestinal tract or via systemic distribution to other regions of the body.

The inventors have unexpectedly found that administering an antibody when bound to a porous substrate has an enhanced therapeutic effect in proteolytic environments compared to administration of the antibody alone. This surprising result evidences the protective effect that the porous substrate imparts on the antibody.

Porous substrates that can be used in accordance with the presence invention include porous silicon substrates, porous polymer substrates, or porous ceramic substrates.

Porous polymer substrates useful for the present invention are known in the art. Such substrates include those containing poly(glycolic acid) (PGA), poly(lactic acid) (PLA) and poly(lactic acidco-glycolic acid) (PLGA), poly(ε-caprolactone) (PCL) and its copolymer, poly(L-lactic acid-co-ε-caprolactone) (PLCL), poly(β-hydroxybutyrate) (PHB) and its copolymer, poly(β-hydroxybutyrate-co-β-hydroxyvalerate (PHBV), polydioxanone (PDO), poly(valerolactone), poly(tartronic acid), poly(β-malonic acid), polytrimethylene carbonate (PTMC), polyorthoesters, polyanhydrides, polypropylene fumarate) (PPF), pseudopoly(amino acids), poly(alkyl cyanoacrylate), polyphosphazene, polyphosphoester and polyurethane. These materials are made via techniques such as non-woven fiber mesh fabrication, particulate leaching, thermally induced phase separation (TIPS), emulsion freeze drying, centrifugation, electrospinning and solid freeform fabrication (SFF). Particulate leaching is a simple and popular technique to fabricate porous scaffolds. Using this approach, the pore size and porosity of the scaffold can be controlled by the size of the particulate (porogen) and particulate/polymer ratio, respectively. In this method, the particulates (sodium chloride, sodium citrate, gelatin, paraffin, etc) are dispersed in a polymer solution in an organic solvent) and the dispersion is cast into a predefined 3D mold.

Particle sizes of porous polymer substrates can range from about 10 nm to about 1000 nm (nanoparticles) to about 1 µm to about 500 µm. Porous polymer substrates can also be made in the form of films and monoliths with structures on the mm/cm scale. Pore sizes of porous polymeric substrates produced via particle/salt leaching methods are typically between about 250 µm to about 355 µm. Other methods known in the art can produce pore sizes ranging from about 20 nm to about 5000 nm, and from about 50 µm to about 400 µm (for example as described in Sosnowski et al. *Macromol. Biosci.* 2006, 6, 425-434).

Porous ceramic substrates useful for the present invention are known in the art. Such substrates include those containing materials such as Hydroxyapatite (HA) and tricalcium phosphate. The biocompatibility is attributed to their chemical composition being similar to that of bone. Porous calcium phosphate ceramics have a high surface area that leads to excellent osteoconductivity and resorbability providing fast bone ingrowth. Hence they can be used in biomedical applications including bone tissue regeneration, cell proliferation, and drug delivery. Porous calcium phosphate can be produced by a variety of methods including conversion of natural bones, ceramic foaming technique, polymeric sponge method, gel casting of foams, solvent casting/salt leaching method, selective laser sintering, precision extrusion deposition, starch consolidation, microwave processing, slip casting, and electrophoretic deposition technique.

Particle sizes of porous ceramic substrates can range from about 10 nm to about 1000 nm (nanoparticles) to about 1 µm to about 500 µm. Pore sizes of porous ceramic substrates produced via particle/salt leaching methods can range up to about 500 µm depending on the size of the porogen (for example as described in Davim et al, *Journal of the European Ceramic Society* 35 (2015, 329-336). Other self-assembly methods can produce pores from about 1.5 µm to about 80 nm (for example as described in Cheng et al. *Crystal Growth & Design.* Vol. 10, No. 3, 2010).

Porous silicon is typically produced by etching pores in crystalline silicon, such as a crystalline silicon wafer. Unusually for mesoporous materials, porous silicon is a crystalline material, in which a coherent crystal structure extends over the whole particle. Furthermore, the structure of porous silicon can be altered over an exceptionally large range by tuning the preparation parameters and by varying the doping of the silicon which makes it suitable for a wide range of applications.

Porous silicon is commonly produced in hydrofluoric acid (HF) containing solutions by one of three methods: chemical stain etching, metal assisted etching and electrochemical etching. In stain etching, an oxidant, such as $HNO_3$, is added into the HF solution. The oxidant creates a cathode reaction resulting in the development of holes which in turn participate in the anode reaction where silicon is selectively dissolved by HF, producing a porous structure. Stain etching is considered a simple method of producing porous silicon but it produces relatively thin porous layers and the ways to control the structure via preparation parameters are limited. Metal assisted etching utilizes deposited metal films or metal particles in the etching process. However, electrochemical etching is by far the most widely used method to form porous silicon as this method provides the best possibilities to control the structure during formation. Electrochemical etching allows for the ability to change the pore structure as the etch propagates into the crystalline silicon. For example, a square wave-form of alternating low and high currents can generate a porous silicon structure that has alternating layers of high and low porosity in the one structure. This is the basis for the generation of high yields of both porous silicon nanoparticles and microparticles. The low porosity layer forms the porous silicon nano- or microparticles while the high porosity layer is removed due to the mechanical processing (ball milling or sonication) destroying this layer.

In electrochemical etching, a voltage is applied between a silicon wafer, acting as an anode, and a cathode (typically made of platinum) in an HF containing electrolyte. The voltage causes holes to appear on the silicon-electrolyte interface where it weakens a bond of a silicon atom which is then dissolved by HF. The pore formation comprises two processes, pore initiation and pore growth. The initial pore formation can take place at structural defects, mechanically strained areas or local perturbations of the surface potential field. Once the pores have been initiated the holes flow preferentially to the bottom of the pores where the dissolution of silicon takes place. The pore growth continues virtually as long as the voltage is being applied, producing a porous layer on the surface of the wafer. There are many parameters that can be used to control the electrochemical etching of porous silicon, including silicon doping, crystal orientation, electrolyte composition), current density, time, temperature and illumination.

Various pore structures can be prepared by varying the etching parameters. In this way, materials with a pore size in the range of few nanometers (i.e. nanoporous silicon and mesoporous silicon) to several micrometers (i.e. microporous silicon and macroporous silicon), surface area from a few $m^2/g$ to 1000 $m^2/g$, and porosities between 5 and 95%, can be achieved. The pores can be smooth walled or branched, interconnected or independent. In addition to the typical fairly uniform porous layers, layered structures can also be formed by periodically varying the current density during electrochemical etching. Furthermore, by sharply increasing the current density just before the end of etching, the silicon under the porous layer can be dissolved making it easy to collect the porous material.

In some embodiments, the porous silicon substrate comprises a porosified silicon film produced from a crystalline silicon wafer by more than one etching step. A single etching step can often result in non-homogeneous pore sizes and the formation of a microporous layer when etching some wafers that possess a highly doped surface. This microporous layer needs to be removed by a first etching step (a sacrificial etching step) to expose the desired porous layer beneath the microporous layer. A second etching step can then be utilized to obtain a porosified silicon film with the desired pore size characteristics.

Since porous silicon produced by electrochemical etching is in the form of a thin film (from a few microns to a few hundreds of microns thick), a size reduction is necessary to produce a particulate form of the porous silicon. Comminution is typically achieved by ball milling, jet milling or sonication. After comminution, the particles typically show a wide size distribution from tens of nanometers (i.e. nanoparticles) to several micrometers (i.e. microparticles). The particles with desired size can be obtained, if required, through sieving or centrifuge separation.

In some embodiments, the porous silicon substrate comprises mesoporous nanoparticles with an average size of between about 100 nm to about 1,000 nm. In some embodiments, the mesoporous nanoparticles comprise an average size in the range of about 100 to about 500 nm, about 100 to about 400 nm, about 100 to about 300 nm, and about 100 to about 200 nm. In some embodiments, the mesoporous nanoparticles comprise an average size in the range of at least about 100 nm to at least about 220 nm. Other sizes are contemplated. Methods for determining the mean size of silicon particles are known in the art.

In some embodiment, the porous silicon substrate comprises mesoporous microparticles with an average size of between about 1 μm to about 500 μm. In some embodiments, the mesoporous microparticles comprise an average size in the range of about 10 to about 500 μm, about 10 to about 400 μm, about 10 to about 300 μm, about 10 to about 200 μm and about 10 to about 100 μm. In some embodiments, the mesoporous microparticles comprise an average size in the range of at least about 40 μm to at least about 100 μm. Other sizes are contemplated.

In some embodiments, the porous silicon substrate comprises a porosity of at least about 50%, at least about 60%, at least about 70%, at least about 80%, or at least 90%. In some embodiments, the porous silicon substrate comprises a porosity of about 90% or less, about 80% or less, about 70% or less, or about 60% or less. In some embodiments, the porous silicon substrate comprises a porosity of about 50 to about 90%, about 60 to about 90%, about 70 to about 90%, about 80 to about 90%, about 50 to about 80%, about 60 to about 80%, about 70 to about 80%, about 50 to about 70%, about 60 to about 70%, or about 50 to about 60%. In some embodiments, the porous silicon substrate comprises a porosity of about 70 to about 90%. Other levels of porosity are contemplated. Methods for determining the porosity of silicon substrates are known in the art.

In some embodiments, the porous silicon substrate comprises a pore size of about 3 to about 200 nm. In some embodiments, the porous silicon substrate comprises a pore size of about 5 to about 200 nm, about 10 to about 200 nm, about 20 to about 200 nm, about 50 to about 200 nm, about 100 to about 200 nm, about 150 to about 200 nm, about 5 to about 150 nm, about 10 to about 150 nm, about 20 to about 150 nm, about 50 to about 150 nm, about 5 to about 100 nm, about 10 to about 100 nm, about 20 to about 100 nm, about 50 to about 100 nm, about 5 to about 50 nm, about 10 to about 50 nm, about 20 to about 50 nm, about 5 to about 40 nm, about 10 to about 40 nm, about 20 to about 40 nm, about 5 to about 20 nm, about 10 to about 20 nm, or about 5 to about 10 nm. In some embodiments, the porous silicon about comprises a pore size of about 250 nm or less, about 200 nm or less, about 150 nm or less, about 100 nm or less, or about 50 nm or less. In some embodiments, the porous silicon about comprises a pore size of at least about 3 nm, at least about 5 nm, at least about 10 nm, at least about 20 nm, at least about 50 nm, or at least about 100 nm. Other sizes are contemplated. Methods for determining the pore size of silicon substrates are known in the art.

In some embodiments, the porous silicon substrate comprises a BET surface area of between about 100 to about 1000 $m^2/g$. In some embodiments, the porous silicon substrate comprises a BET surface area of between about 200 to about 1000 $m^2/g$, about 200 to about 500 $m^2/g$, about 200 to about 750 $m^2/g$, about 200 to about 500 $m^2/g$, about 500 to about 1000 $m^2/g$, about 500 to about 800 $m^2/g$, about 500 to about 750 $m^2/g$, about 750 to about 1000 $m^2/g$, about 750 to about 800 $m^2/g$, or about 800 to about 1000 $m^2/g$. In some embodiments, the porous silicon substrate comprises a BET surface area of at least about 100 $m^2/g$, at least about 200 $m^2/g$, at least about 500 $m^2/g$, at least about 750 $m^2/g$, or at least about 800 $m^2/g$. In some embodiments, the porous silicon substrate comprises a BET surface area of about 1000 $m^2/g$ or less, about 800 $m^2/g$ or less, about 750 $m^2/g$ or less, about 500 $m^2/g$ or less, or about 200 $m^2/g$ or less. Other surface areas are contemplated. Methods for determining the BET surface area of silicon substrates are known in the art.

The surface of freshly prepared porous silicon is covered with hydrides which protect the highly reactive silicon structure against oxidation to some extent. However, the hydrogen terminated porous silicon oxidizes slowly at ambient conditions due to atmospheric oxygen and water vapour. Furthermore, hydride covered porous silicon rapidly oxidizes in water and can act as reducing agent which provides poor stabilization against dissolution in an aqueous environment. Typically, steps are taken to stabilize the surface of the porous silicon substrate. The two most common ways to stabilize porous silicon are the formation of an oxide surface and stabilization by addition of carbon atoms.

A stabilized oxide layer can be achieved in several ways, for example by thermal oxidation, anodic oxidation, liquid phase oxidation, or ozone oxidation. These methods create oxide layers of varying thicknesses with varying densities of surface —H and —OH groups.

In some embodiments, the porous silicon substrate has been thermally oxidized at a temperature less than about 600° C. In some embodiments, the porous silicon substrate has been thermally oxidized at a temperature less than about 500° C. In some embodiments, the porous silicon substrate has been thermally oxidized at a temperature of about 400° C.

In some embodiments, the pores of the substrate are not-functionalized. In some embodiments, the pores of the substrate are functionalized.

In some embodiments, the pores of the substrate comprise one or more stimulus responsive polymers to assist with release in response to a stimulus. In certain embodiments, the pores of the substrate do not comprise a stimulus response polymer.

In accordance with the first aspect of the present invention, the composition comprises an antibody. In some embodiments, the antibody may be a therapeutic antibody. As would be understood by a person skilled in the art an "antibody" refers to a polypeptide comprising a framework region from an immunoglobulin gene or fragments thereof that specifically binds and recognizes an antigen. The term "antibody" in the context of the present invention is therefore used in the broadest sense and encompasses for example intact polyclonal antibodies, intact monoclonal antibodies, antibody fragments which retain the antigen binding part or portion of the intact antibody (such as linear antibodies, single-chain antibody molecules, Fc or Fc' peptides, Fab, Fab', F(ab')2, and Fv fragments), chimeric antibodies, humanised antibodies, single chain Fv (scFv) mutants, multi-specific antibodies such as bispecific antibodies generated from at least two intact antibodies, fusion proteins comprising an antibody portion, and any other modified immunoglobulin molecule comprising an antigen recognition site so long as the antibodies exhibit the desired biological activity.

The recognized immunoglobulin genes include the kappa, lambda, alpha, gamma, delta, epsilon, and mu constant region genes, as well as the multitude of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

Naturally occurring immunoglobulins have a common core structure in which two identical light chains (about 24 kD) and two identical heavy chains (about 55 or 70 kD) form a tetramer. The amino-terminal portion of each chain is known as the variable (V) region and can be distinguished from the more conserved constant (C) regions of the remainder of each chain. Within the variable region of the light chain is a C-terminal portion known as the J region. Within the variable region of the heavy chain, there is a D region in addition to the J region. Most of the amino acid sequence variation in immunoglobulins is confined to three separate locations in the V regions known as hypervariable regions or complementarity determining regions (CDRs) which are directly involved in antigen binding. Proceeding from the amino-terminus, these regions are designated CDR1, CDR2 and CDR3, respectively. The CDRs are held in place by more conserved framework regions (FRs). Proceeding from the amino-terminus, these regions are designated FR1, FR2, FR3, and FR4, respectively. The locations of CDR and FR regions and a numbering system have been defined for example by Kabat et al., 1991 (Sequences of Proteins of immunological Interest, Fifth Edition, U.S. Department of Health and Human Services, U.S. Government Printing Office).

The term "antigen binding part" or "antigen binding portion" is to be understood to mean the antigen-binding portion of the antibody molecule, including for example a Fab, Fab', F(ab')$_2$, Fv, a single-chain antibody (scFv), a chimeric antibody, a diabody or any polypeptide that contains at least a portion of an immunoglobulin that is sufficient to confer specific antigen binding, such as a molecule including one or more CDRs (see further detail below).

Antibodies typically exist as intact immunoglobulins or as a number of well-characterized fragments produced by digestion with various peptidases. Therefore, for example, pepsin digests an antibody below the disulfide linkages in the hinge region to produce F(ab)'$_2$, a dimer of Fab which itself is a light chain joined to $V_H$-$C_H$, by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region. While various antibody fragments are defined in terms of the digestion of an intact antibody, a person skilled in the art would appreciate that such fragments may be synthesized de novo either chemically or by using recombinant DNA methodology. Therefore, the term antibody, as used herein, also includes antibody fragments either produced by the modification of whole antibodies, or those synthesized de novo using recombinant DNA methodologies (e.g. single chain Fv) or those identified using phage display libraries for example McCafferty et al., 1990, *Nature* 348:552-554).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g. an enzyme, toxin, hormone, growth factor, drug, etc.; or (b) the variable region, or a portion thereof, is altered, replaced or exchanged with a variable region having a different or altered antigen specificity. The chimeric antibodies may be monovalent, divalent, or polyvalent immunoglobulins. For example, a monovalent chimeric antibody is a dimer (HL) formed by a chimeric H chain associated through disulfide bridges with a chimeric L chain, as noted above. A divalent chimeric antibody is a tetramer ($H_2L_2$) formed by two HL dimers associated through at least one disulfide bridge. A polyvalent chimeric antibody is based on an aggregation of chains.

In some embodiments, the antibody may be a humanized antibody. A "humanized" antibody is an antibody that retains the reactivity of a non-human antibody while being less immunogenic in humans. This can be achieved, for example, by retaining the non-human CDR regions and replacing the remaining parts of the antibody with their human counterparts. See for example Morrison et al., 1984, *Proc. Natl. Acad. Sci. USA*, 81: 6851-6855; Morrison and Oi, 1988, *Adv. Immuno.*, 44: 65-92; Verhoeyen et al., 1988, *Science*, 239: 1534-1536; Padian, 1991, *Molec. Immun.*, 28: 489-498; and Padlan, 1994, *Molec. Immun.*, 31: 169-217.

In one embodiment, the antibody is a neutralizing antibody. As would be understood by a person skilled in the art, a neutralizing antibody is and antibody that can reduce or neutralise the expression and/or activity of the antigen to which it binds. Methods for producing antibodies, including neutralizing antibodies, are as described below.

Antibodies for use in the compositions of the present invention can be commercially purchased (if available) or can be produced according to well-established techniques in the art, for example by immunizing animals with the relevant antigen. Alternatively, if the amino acid sequence of the relevant antigen is known, the polypeptide (or a portion thereof) can be synthesized and used to generate antibodies by methods well-known in the art. For example, monoclonal antibodies may be prepared using any technique which provides for the production of antibody molecules by continuous cell lines in culture. These include, but are not limited to, the hybridoma technique, the human B-cell hybridoma technique, and the EBV-hybridoma technique (for example, see Kohler et al., 1975, *Nature* 256: 495-497; Kozbor et al., 1985, *J. Immunol. Methods* 81:31-42; Cote et al., 1983, *Proc. Natl. Acad. Sci. USA* 80: 2026-2030; and Cole et al., 1984. *Mol. Cell Biochem.* 62: 109-120).

Antibodies may also be produced by inducing in vivo production in the lymphocyte population or by screening immunoglobulin libraries or panels of highly specific binding reagents as disclosed in the literature (for example, see Orlandi et al., 1989, *Proc. Natl. Acad. Sci. USA* 86: 3833-3837; and Winter and Milstein, 1991, *Nature* 349: 293-299). Antibodies may also be generated using phage display. For example, functional antibody domains are displayed on the surface of phage particles that carry the polynucleotide sequences encoding them. Such phage can be utilized to display antigen-binding domains expressed from a repertoire or combinatorial antibody library (e.g. human or murine). Phage expressing an antigen binding domain that binds to the relevant antigen can be selected or identified, e.g. by using labelled antigen or a portion thereof. Phage used in these methods are typically filamentous phage including fd and MI 3 binding domains expressed from phage with Fab, Fv or disulfide stabilised Fv antibody domains recombinantly fused to either the phage gene III or gene VIII protein. Examples of phage display methods that can be used to make the antibodies may include those disclosed in Brinkman et al., 1995, *J. Immunol. Methods* 182: 41-50; Ames et al., 1995, *J. Immunol. Methods* 184: 177-186; Kettleborough et al., 1994, *Eur. J. Immunol.* 24: 952-958; Persic et al., 1997, *Gene* 187: 9-18; Burton et al., 1994, *Advances in Immunology* 57: 191-280; PCT application number PCT/GB91/01134; PCT publications numbers WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,518,637; 5,780,225; 5,658,727; 5,733,743 and 5,969,108; each of which is incorporated herein by reference in its entirety.

Techniques which can be used to produce single-chain Fvs and antibodies include those described in U.S. Pat. Nos. 4,946,778 and 5,258,498; Huston et al., 1991, *Methods in Enzymology* 203: 46-88; Shu et al., 1993, *Proc. Natl. Acad. Sci. USA* 90: 7995-7999; and Skerra et al., 1988, *Science* 240: 1038-1040.

Antibody fragments which contain specific binding sites for a relevant antigen may be generated using standard techniques known in the art. For example, F(ab')2 fragments may be produced by pepsin digestion of the selected antibody and Fab fragments generated by reducing the disulfide bridges of the F(ab')2 fragments. Alternatively, Fab expression libraries may be constructed to allow rapid and easy identification of monoclonal Fab fragments with the desired specificity (for example, see Huse et al., 1982, *Science* 246: 1275-1281).

Various immunoassays may be used for screening to identify antibodies having the desired specificity. Numerous protocols for competitive binding or immunoradiametric assays using either polyclonal or monoclonal antibodies with established specificities are well known in the art. Such immunoassays typically involve the measurement of complex formation between a protein and its specific antibody. A two-site, monoclonal-based immunoassay utilising antibodies reactive to two non-interfering epitopes is preferred, but a competitive binding assay may also be employed.

In some embodiments, the antibody is an antibody to the Flightless I protein. Flightless I antibodies can be purchased commercially. For example, mouse monoclonal anti-flightless I antibody (sc-21716) can be obtained from Santa Cruz Biotechnology (Santa Cruz, Calif., USA). Flightless I antibody can also be made using the techniques described above.

In some embodiments, the Flightless I antibody is a monoclonal antibody. In some embodiments, the monoclonal antibody is a neutralizing antibody. In one embodiment, the neutralizing antibody binds specifically to the leucine rich repeat domain of the Flightless I protein. Such a neutralizing antibody can be made using the techniques described above or in accordance with those described in Davy D A et al., 2001. "The flightless I protein colocalizes with actin- and microtubule-based structures in motile Swiss 3T3 fibroblasts: evidence for the involvement of PI 3-kinase and Ras-related small GTPases", *J. Cell Sci.* 114: 549-562. For example, peptide corresponding to a sequence of human Flightless I can be synthesized and conjugated to keyhole limpet haemocyanin using established techniques. An appropriate host is then injected subcutaneously and serum collected following clot retraction and stored at −70° C. Flightless I antibodies are then affinity-purified using established techniques.

As used herein, "Flightless I" is to be understood to refer to a gene that encodes a protein with a gelsolin-like actin binding domain and an N-terminal leucine-rich repeat-protein protein interaction domain. Flightless I was originally identified in *Drosophila* where mutations in the gene caused defects in the flight muscles which, consequently, were unable to support flight. The Flightless I gene has since been found to be present in a number of species, including human, chimpanzee, baboon, monkey, mouse, zebrafish, frog, dog and yeast. Indeed, between the higher order species, the Flightless I protein is highly conserved suggesting that it carries out important, conserved functions. In this regard, the Flightless I protein has been shown to be an important mediator of wound repair and cancer, including squamous cell carcinoma. Flightless I is also known as FLI, FLIL, Fli1, Flii, FLII, and flightless I homolog (*Drosophila*).

The human Flightless I gene encodes a 140 kD protein which is a member of the gelsolin family of proteins. The human gene encodes three isoforms variants, the mRNA and amino acid sequences of which are set out in SEQ ID NOs: 1 to 6, and represented by GenBank Accession Numbers NM_002018.3 and NP_002009.1 (variant 1), NM_001256264.1 and NP_001243193.1 (variant 2), and NM_001256265.1 and NP_001243194.1 (variant 3). Further details of the Flightless I gene in human and other species may be accessed from the GenBank database at the National Centre for Biotechnology Information (NCBI) (www.ncbi.nlm.nih.gov). For example, the Gene ID number for human Flightless I is 2314, for chimpanzee is 454486, for baboon is 101019011, for monkey is 700471, for mouse is 14248, for zebrafish is 560281, for frog is 444748, for dog is 479521, and for yeast is 176215.

Further details regarding the Flightless I gene in other species can be found at the UniGene portal of the NCBI (i.e. UniGene Hs. 513984—http://www.ncbi.nlm.nih.gov/UniGene/clust.cgi?ORG=Hs&CID=513984&ALLPROT=1). Alternatively, details of the nucleotide and amino acid sequence for Flightless I can be accessed from the UniProt database (www.uniprot.org) wherein the UniProt ID for human Flightless I is Q13045 (variant 1 and 2), and F5H407 (variant 3). The contents of the GenBank and UniProt records are incorporated herein by reference.

It is to be made clear that reference herein to Flightless I, includes a reference to its naturally-occurring variants. In this regard, a "variant" of Flightless I may exhibit a nucleic acid or an amino acid sequence that is, for example, at least 80% identical, at least 90% identical, at least 95% identical, at least 98% identical, at least 99% identical, or at least 99.9% identical to native Flightless I. In some embodiments, a variant of Flightless I is expected to retain native biological activity or a substantial equivalent thereof.

In some embodiments, the antibody is a monoclonal antibody to tumour necrosis factor-alpha (TNF-α). TNF-α is a potent pro-inflammatory cytokine exerting pleiotropic effects on various cell types and plays a critical role in the pathogenesis of chronic inflammatory diseases, such as rheumatoid arthritis. TNF-α belongs to the tumor necrosis factor (TNF) superfamily. This cytokine is mainly secreted by macrophages. It can bind to, and thus functions through its receptors TNFRSF1A/TNFR1 and TNFRSF1B/TNFBR. This cytokine is involved in the regulation of a wide spectrum of biological processes including cell proliferation, differentiation, apoptosis, lipid metabolism, and coagulation. This cytokine has been implicated in a variety of diseases, including autoimmune diseases, insulin resistance, and cancer. Tumour necrosis factor-alpha is also known as tumor necrosis factor, APC1 protein, TNF, macrophage-derived TNF, monocyte-derived TNF-α, cachectin, and tumor necrosis factor ligand superfamily member 2.

The human TNF-α gene comprises the mRNA sequence set out in SEQ ID NO: 7, and as represented by GenBank Accession Number NM_000594.3. The gene encodes a protein comprising the amino acid sequence set out in SEQ ID NO: 8, and represented by GenBank Accession Number NP_000585.2. Further details of the TNF-α gene in human and other species may be accessed from the GenBank database at the National Centre for Biotechnology Information (NCBI) (www.ncbi.nlm.nih.gov). For example, the Gene ID number for human TNF-α is 7124, for mouse is 21926, for chimpanzee is 744399, for baboon is 100126739, for cow is 280943, for cat is 493755, for dog is 403922, and for horse is 100033834.

Further details regarding the TNF-α gene in other species can be found at the UniGene portal of the NCBI (i.e. UniGene Hs. 241570—http://www.ncbi.nlm.nih.gov/UniGene/clust.cgi?UGID=167910&TAXID=9606&SEARCH=7 124[LID]). Alternatively, details of the nucleotide and amino acid sequence for TNF-α can be accessed from the UniProt database (www.uniprot.org) wherein the UniProt ID for human TNF-α is P01375. The contents of the GenBank and UniProt records are incorporated herein by reference.

It is to be made clear that reference herein to TNF-α, includes a reference to its naturally-occurring variants. In this regard, a "variant" of TNF-α may exhibit a nucleic acid or an amino acid sequence that is, for example, at least 80% identical, at least 90% identical, at least 95% identical, at least 98% identical, at least 99% identical, or at least 99.9% identical to native TNF-α. In some embodiments, a variant of TNF-α is expected to retain native biological activity or a substantial equivalent thereof.

In one embodiment, the monoclonal antibody to TNF-α is Infliximab. Infliximab is clinically approved to treat Crohn's disease and rheumatoid arthritis and functions by neutralizing the function of TNF-α. Infliximab has also been studied for the treatment of psoriasis, ulcerative colitis, chronic venous ulcers and uveitis. Infliximab is administered by intravenous infusion, typically at six- to eight-week intervals. However, it cannot be administered orally due to degradation in the stomach. Infliximab is sold under the trade name of Remicade®.

In some embodiments, the porous substrate comprises antibodies directed to more than one antigen. In some embodiments, the porous substrate comprises antibodies directed to at least two different antigens.

According to a first aspect of the present invention, the antibody is bound to the porous substrate.

Reference herein to an antibody being "bound" to the substrate is taken to mean that the antibody may be, directly or indirectly, "absorbed by", "attached to", "linked to". "loaded onto" the porous substrate at either or both of the surface and internal regions of the substrate (e.g. in the pores of the substrate), and/or that the antibody may be passively bound to the substrate or covalently bound to the substrate.

For example, an antibody may be passively bound to the substrate using electrostatic interactions between the antibody and the substrate.

In some embodiments, the amount of antibody present in the composition is in the range from about 1% to about 300% by weight of the composition. In some embodiments, the amount of antibody present in the composition is in the range from about 1% to about 200%, about 1% to about 100%, about 1% to about 50%, about 1% to about 10%, about 5% to about 300%, about 5% to about 200%, about 5% to about 100%, about 5% to about 50%, about 5% to about 10%, about 10% to about 300%, about 10% to about 200%, about 10% to about 100%, about 10% to about 100%, about 10% to about 50%, about 20% to about 300%, about 20% to about 200%, about 20% to about 100%, about 20% to about 50%, about 50% to about 300%, about 50% to about 200%, about 50% to about 100%, about 100% to about 300%, about 100% to about 200%, and about 200% to about 300%, by weight of the composition.

In some embodiments, the method according to the first aspect of the present invention is used to treat a disease, disorder or condition in a proteolytic environment. In some embodiments, the disease, disorder or condition is selected from the group consisting of a wound, an ocular condition, cancer, or an inflammatory condition. Other types of diseases, disorders or conditions are contemplated.

In some embodiments, the wound includes an acute wound, a chronic wound, or a wound in an individual with compromised wound healing capacity. In some embodiments, the acute wound is the result of a penetrative injury, a burn, nerve damage or from elective surgery. In some embodiments, the chronic wound is a diabetic, venous, arterial, or decubitus, ulcer.

In some embodiments, the ocular condition is selected from the group consisting of glaucoma, proliferative, vitreoretinopathy, macular oedema, including diabetic macular oedema, age-related macular degeneration, diabetic retinopathy, uveitis, ocular neovascularization and ocular infection. In some embodiments, the ocular condition is corneal neovascularization or uveitis.

In some embodiments, the inflammatory condition is selected from the group consisting of arthritis, ocular inflammation, chronic pain, rheumatic disease (including rheumatoid arthritis), gastritis, gastroenteritis, inflammatory bowel disease, irritable bowel syndrome, ulcerative colitis, and Crohn's disease.

In some embodiments, the cancer is selected from the group consisting of carcinoma, bladder cancer, bone cancer, brain cancer, breast cancer, cervical cancer, colorectal cancer including cancer of the colon, rectum, anus, and appendix, cancer of the oesophagus, Hodgkin's disease, kidney cancer, cancer of the larynx, leukaemia, liver cancer, lung cancer, lymphoma, multiple myeloma, muscular cancer, non-Hodgkin's lymphoma, glioblastoma, oral cancer, ovarian cancer, cancer of the pancreas, prostate cancer, sarcoma, skin cancer, stomach cancer, testicular cancer, teratoma, thyroid cancer, and cancer of the uterus.

In one embodiment, the cancer is selected from the group consisting of skin cancer, colorectal cancer, and lung cancer. In one embodiment, the skin cancer is squamous carcinoma.

In some embodiments, the disease, disorder or condition is a disease, disorder or condition of the gastrointestinal tract. In some embodiments, the disease, condition or disorder is a disease, condition or disorder of the lower gastrointestinal tract.

In some embodiments, the composition further comprises an agent that protects the antibody from proteolysis, reduces protein misfolding, and/or reduces protein denaturation.

In some embodiments, the agent comprises a protein. In one embodiment, the protein is present in the composition in an amount from about 1% to about 400% by weight of the antibody present in the composition. For example, the protein may be present in the composition in an amount from about 1% to about 300%, about 1% to about 200%, about 1% to about 100%, about 1% to about 50%, about 10% to about 400%, about 10% to about 300%, about 10% to about 200%, about 10% to about 100%, about 10% to about 50%, about 50% to about 400%, about 50% to about 300%, about 50% to about 200%, about 50% to about 100%, about 100% to about 400%, about 100% to about 300%, about 100% to about 200%, about 200% to about 400%, about 200% to about 300%, and about 300% to about 400%, by weight of the antibody present in the composition. In some embodiments, the protein can be loaded onto the porous substrate before antibody loading or at the same time as antibody loading.

In some embodiments, the agent comprises a peptide, an oligopeptide and/or a polypeptide. In some embodiments, the agent comprises a protein.

In some embodiments, the protein comprises a serum albumin. In one embodiment, the protein is bovine serum albumin. In one embodiment, the protein comprises an albumin. In one embodiment, the protein comprises a serum albumin. In one embodiment, the protein is bovine serum albumin. In one embodiment, the bovine serum albumin is present in the composition in an amount set forth above. For example the bovine serum albumin is present in the composition in an amount from about 10% to about 400% by weight of the antibody present in the composition. Any amount falling within these ranges is included. In some embodiments, the agent comprises a peptide, an oligopeptide and/or a polypeptide.

In some embodiments, the porous substrate is biodegradable in vivo. For example, porous silicon substrates, unlike their crystalline silicon precursors, have been shown to biodeorade in vitro and in vivo producing innocuous by-products, i.e., monomeric silicic acid ($Si(OH)_4$). Silicic acid, which is naturally present in blood plasma at levels of less than 1 mg Si/L from the dietary intake of 20-50 mg/day, is readily removed by the kidneys. Biodegradable, as used herein, refers to the chemical breakdown of materials by a physiological environment. The physiological environment under which the biodegredation occurs may be within an organism or external to an organism such as in a test tube or Petri dish.

In some embodiments, the porous substrate is partially or completely biodegradable. For example, the substrate may comprise biodegradable polymers or porous silicon, such that after the useful life of the substrate, the substrate completely degrades to innocuous by-products. In other exemplary embodiments, the particle may include materials that are biodegradable and non-biodegradable. In such embodiments, the non-biodegradable component may need to be removed from the body following drug release.

In some embodiments, the substrate has a lifespan of hours, days, weeks, months or years. The term lifespan, as referred to herein, indicates the time between a particle's introduction into a biological environment, e.g., in vivo, ex vivo or in vitro, until the particle has completely biodegraded. In some embodiments, the substrate may completely degrade within hours or days such as from about 4 to 24 hours, for example about 5 hours, about 10 hours, about 15 hours, about 20 hours, about 1 day, or from about 2 days to 2 weeks, for example about 2 days, about 5 days, about 10 days, or greater than 2 weeks, such as from about 15 days, or about 20 days. In some embodiments, the substrate degrades over a period of weeks or months such as about 3 weeks, about 1 month, about 2 months, about 3 months, about 6 months, about 9 months, about 1 year, about 2 years or about 3 years.

In some embodiments of the first aspect of the present invention, the administering of the composition comprises exposing the proteolytic environment to a dressing or bandage, or the like, that comprises the composition. Such a mode of delivery of the composition is common for the treatment of wounds or conditions which manifest on external regions of the body and are therefore exposed to the environment in the absence of the dressing or bandage.

For the treatment of wounds, a warm moist wound environment appears to achieve more rapid and successful wound healing. In some embodiments, the dressing and bandages (and the like) encompassed by the present invention meet this requirement. The nature of such dressings and bandages are known to those skilled in the art. A summary of some commonly used dressings and bandages for delivery of active agents to wounds is also summarised in Boateng J S et al., 2008, "Wound healing dressings and drug delivery systems: A review", *J. Pharmac. Sci.*, 97: 2892-2923.

As an example, dressings are classified in a number of ways depending on their function in the wound (debridement, antibacterial, occlusive, absorbent, adherence), type of material employed to produce the dressing (e.g. hydrocolloid, alginate, collagen) and the physical form of the dressing (ointment, film, foam, gel). Dressings are further classified into primary, secondary and island dressings. Dressings which make physical contact with the wound surface are referred to as primary dressings while secondary dressings cover the primary dressing. Island dressings possess a central absorbent region that is surrounded by an adhesive portion.

Bandages are typically made from natural wool and cellulose) and synthetic (e.g. polyamide) materials, which perform different functions. For example, Cotton Conforming Bandage 1988 is used for the retention of light dressings, High Compression Bandages, are used for the application of sustained compression in the treatment of venous insufficiency. Short Stretch Compression Bandage is used for venous leg ulcers and lymphoedema. Polyamide and Cellulose Contour Bandage, Knitted BP 1988 is used for dressing retention.

Hydrocolloid dressings are among the most widely used dressings. The term hydrocolloid describes the family of wound management products obtained from colloidal (gel forming agents) materials combined with other materials such as elastomers and adhesives. Typical gel forming agents include carboxymethylcellulose (CMC), gelatin and pectin. Examples of hydrocolloid dressings include Granuflex and Aquacel (Conva Tec, Hounslow, UK), Comfeel (Coloplast, Peterborough, UK) and Tegasorb (3M Healthcare, Loughborough, UK). They occur in the form of thin films and sheets or as composite dressings in combination with other materials such as alginates. These dressings can be formulated to comprise the compositions of the present invention as described above.

Alginate dressings are produced from the calcium and sodium salts of alginic acid, a polysaccharide comprising mannuronic and guluronic acid units. Alginate dressings occur either in the form of freeze-dried porous sheets (foams) or as flexible fibres, the latter indicated for packing cavity wounds. The use of alginates as dressings stems primarily from their ability to form gels upon contact with wound exudates (high absorbency). The high absorption occurs via strong hydrophilic gel formation, which limits wound secretions and minimises bacterial contamination. Alginates rich in mannuronate, such as Sorbsan (Maersk, Suffolk, UK) form soft flexible gels upon hydration whereas those rich in guluronic acid, like Kaltostat (Conva Tec), form firmer gels upon absorbing wound exudate. Some contain calcium alginate fibre such as Sorbsan and Tegagen (3M Healthcare). Comfeel Plus is a hydrocolloid/alginate combination dressing. When applied to wounds, ions present in the alginate fibre are exchanged with those present in exudate and blood to form a protective film of gel. These dressings can be formulated to comprise the compositions of the present invention as described above.

Hydrogel dressings (hydrogels) are insoluble, swellable hydrophilic materials made from synthetic polymers such as poly(methacrylates) and polyvinylpyrrolidine. Some dressings such as Nu-gel (Johnson & Johnson, Ascot, UK) and Purilon (Coloplast) are hydrogel/alginate combinations. Hydrogels can be applied either as an amorphous gel or as elastic, solid sheet or film. Hydrogels possess most of the desirable characteristics of an 'ideal dressing'. They are suitable for cleansing of dry, sloughy or necrotic wounds by rehydrating dead tissues and enhancing autolytic debridement. Hydrogel dressings are nonreactive with biological tissue, permeable to metabolites and are non-irritant. Hydrogels also promote moist healing, are non-adherent and cool the surface of the wound, which may lead to a marked reduction in pain and therefore have high patient acceptability. These dressings can be formulated to comprise the compositions of the present invention as described above.

Additional dressing types include semi-permeable adhesive film dressings and foam dressings (such as those made from polyurethane), biological dressings, tissue engineered skin substitutes, silicone gels, collagen films, and polymeric dressings, each of which can be formulated to comprise the compositions the present invention as described above.

In some embodiments of the first aspect of the present invention, the administering of the composition comprises topical administration of the composition to the proteolytic environment. For topical administration, the composition of the present invention may be in the form of a solution, spray, lotion, cream (for example a non-ionic cream), gel, paste, bandage, dressing, or ointment.

A cream is a formulation that contains water and oil and is stabilized with an emulsifier. Lipophilic creams are called water-in-oil emulsions, and hydrophilic creams oil-in-water emulsions. The cream base for water-in-oil emulsions are normally absorption bases such as vaseline, ceresin or lanolin. The bases for oil-in-water emulsions are mono-, di-, and tri-glycerides of fatty acids or fatty alcohols with soaps, alkyl sulphates or alkyl polyglycol ethers as emulsifiers.

A lotion is an opaque, thin, non-greasy emulsion liquid dosage form for external application to the skin, which generally contains a water-based vehicle with greater than 50% of volatiles and sufficiently low viscosity that it may be delivered by pouring. Lotions are usually hydrophilic, and contain greater than 50% of volatiles as measured by LOD (loss on drying). A lotion tends to evaporate rapidly with a cooling sensation when rubbed onto the skin.

A paste is an opaque or translucent, viscous, greasy emulsion or suspension semisolid dosage form for external application to the skin, which generally contains greater than 50% of hydrocarbon-based or a polyethylene glycol-based vehicle and less than 20% of volatiles. A paste contains a large proportion (20-50%) of dispersed solids in a fatty or aqueous vehicle.

An ointment is an opaque or translucent, viscous, greasy emulsion or suspension semisolid dosage form for external application to the skin, which generally contains greater than 50% of hydrocarbon-based or a polyethylene glycol-based vehicle and less than 20% of volatiles. An ointment is usually lipophilic, and contains >50% of hydrocarbons or polyethylene glycols as the vehicle and <20% of volatiles as measured by LOD. An ointment tends not to evaporate or be absorbed when rubbed onto the skin.

A gel is usually a translucent, non-greasy emulsion or suspension semisolid dosage form for external application to the skin, which contains a gelling agent in quantities sufficient to impart a three-dimensional, cross-linked matrix. A gel is usually hydrophilic, and contains sufficient quantities of a gelling agent such as starch, cellulose derivatives, carbomers, magnesium-aluminum silicates, xanthan gum, colloidal silica, aluminium or zinc soaps.

The composition for topical administration may further include drying agents, anti-foaming agents; buffers, neutralizing agents, agents to adjust pH; colouring agents and decolouring agents; emollients; emulsifying agents, emulsion stabilizers and viscosity builders; humectants; odorants; preservatives, antioxidants, and chemical stabilizers; solvents; and thickening, stiffening, and suspending agents, and a balance of water or solvent.

In some embodiments of the first aspect of the present invention, the administering of the composition comprises systemic administration of the composition to the proteolytic environment. The composition may be administered systemically through various means including parenteral and oral administration of the composition.

The term parenteral as used herein includes subcutaneous, intravenous, intramuscular, intraperitoneal, intrathecal, intraventricular, intrasternal, and intracranial injection or infusion techniques. When administered parenterally, the composition will normally be in a unit dosage, sterile injectable form (solution, suspension or emulsion) which is preferably isotonic with the blood of the recipient with a pharmaceutically acceptable carrier. Examples of such sterile injectable forms are sterile injectable aqueous or oleaginous suspensions. These suspensions may be formulated according to techniques known in the art using suitable dispersing or wetting agents and suspending agents. The sterile injectable forms may also be sterile injectable solutions or suspensions in non-toxic parenterally acceptable diluents or solvents, for example, as solutions in 1,3-butanediol. Among the acceptable vehicles and solvents that may be employed are water, saline, Ringers solution, dextrose solution, isotonic sodium chloride solution, and Hanks' solution. In addition, sterile, fixed oils are conventionally employed as solvents or suspending mediums. For this purpose, any bland fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethylated versions, are useful in the preparation of injectables. These oil solutions or suspensions may also contain long-chain alcohol diluents or dispersants.

When administered orally, the agent will usually be formulated into unit dosage forms such as tablets, cachets, powder, granules, beads, chewable lozenges, capsules, liquids, aqueous suspensions or solutions, or similar dosage forms, using conventional equipment and techniques known in the art. Such formulations typically include a solid, semisolid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like.

A tablet may be made by compressing or moulding the agent optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Moulded tablets may be made by moulding in a suitable machine, a mixture of the powdered active ingredient and a suitable carrier moistened with an inert liquid diluent.

Additional numerous various excipients, dosage forms, dispersing agents and the like that are suitable for use in connection with the administration of the composition encompassed by the present invention and/or the formulation of said composition into medicaments or pharmaceutical compositions. Formulations are known and described in, for example, Remington's Pharmaceutical Sciences, 17th ed., Mack Publishing Company, Easton, Pa., 1985, which is incorporated herein by reference in its entirety. Methods for preparing, formulating and administering compositions comprising an antibody are known in the art, and include for example "Handbook of Therapeutic Antibodies, $2^{nd}$ Edition" ed, S. Dubel and Reichert J. M. (2014) Wiley-Blackwell, which is also incorporated herein by reference in its entirety.

In a second aspect, the present invention provides a method of administering an antibody to a wound, the method comprising administering a composition to the wound, wherein the composition comprises a porous silicon substrate and the antibody bound to the substrate, and releasing the antibody from the substrate so as to administer the antibody to the wound.

In a third aspect, the present invention provides a method of treating a wound, the method comprising administering a composition to the wound, wherein the composition comprises a porous silicon substrate and an antibody bound to the substrate, and releasing the antibody from the substrate so as to administer the antibody to the wound, thereby treating the wound.

The term "treating", and related terms such as "treatment" and "treat", refer to obtaining a desired pharmacologic and/or physiologic effect in terms of improving the condition of the subject, ameliorating, arresting, suppressing, relieving and/or slowing the progression of one or more symptoms in the subject, a partial or complete stabilization of the subject, a regression of the one or more symptoms, or a cure of a disease, disorder or condition in the subject. The terms include within their scope one or more of the following outcomes: (i) inhibiting to some extent reduction, slowing down or complete stopping) wound progression in a subject, including, slowing down and/or complete regression of the wound; (ii) reducing the pain and distress to the subject associated with the wound; (iii) alleviating, abating or ameliorating at least one symptom of the wound in a subject; (iv) reducing the size of the wound in a subject; (v) improving the life expectancy of a subject as compared to the untreated state; (vi) improving the quality of life of a subject as compared to the untreated state; (vii) relieving a condition in a subject that is caused by the wound; and (vii) stopping symptoms in a subject that are associated with the wound.

In a fourth aspect, the present invention provides a method of improving repair of a wound, the method comprising administering a composition to the wound, wherein the composition comprises a porous silicon substrate and an antibody bound to the substrate, and releasing the antibody from the substrate so as to administer the antibody to the wound, thereby improving repair of the wound.

Typically, the improvement in repair of the wound as a result of administration of the compound to the wound is an assessment of a wound repair characteristic (e.g. rate of wound healing, quality of wound healing, etc) in comparison to a control. Relevant controls would include repair of the wound in the absence of administration of the compound, or the progression of wound repair expected for administration of the antibody alone to the wound (i.e. when not formulated with the porous substrate). Generally, an "improvement" in repair of the wound may be measured as an increase of at least 10%, 20%, 30%, 40%, 50%, 60%, 70%, 80%, 90%, or 100%, relative to a control.

In another aspect, the present invention provides a method of protecting an antibody from proteolytic degradation, the method comprising binding the antibody to a porous substrate and thereby protecting the antibody from proteolytic degradation.

In another aspect, the present invention provide a method of protecting an antibody from degradation in a proteolytic environment, the method comprising binding the antibody to a porous substrate and thereby protecting the antibody from degradation in the proteolytic environment.

In a fifth aspect, the present invention provides a composition for administering an antibody to, and/or via, a proteolytic environment, the composition comprising a porous substrate and an antibody bound to the substrate. Details regarding the composition have been described above.

In another aspect, the present invention provides a composition for protecting an antibody from degradation in a proteolytic environment, wherein the composition comprises a porous silicon substrate and an antibody bound to the substrate.

In one embodiment of the fifth aspect of the present invention, the composition is a wound healing composition that can be used to treat a wound, as described above. Accordingly, in a further embodiment, the present invention provides a wound healing composition comprising a porous silicon substrate and an antibody bound to the substrate. As indicated above, the composition can form the active part of a dressing or bandage which is applied to the wound during treatment of the wound.

In another embodiment of the fifth aspect of the present invention, the composition is a topical composition that can be used to treat a wound, as described above. For example, an antibody to Flightless I may be formulated into a topical composition for topical administration to a wound, or the antibody may be formulated into a composition for injection into one or more regions near or surrounding the wound. In one embodiment, the topical composition is a topical wound healing composition comprising an antibody to Flightless I. Topical compositions including an antibody are generally as described in U.S. Pat. No. 5,702,946.

In another embodiment of the fifth aspect of the present invention, the composition is an oral composition, as described above. Accordingly, in a further embodiment, the present invention provides an oral composition comprising a porous silicon substrate and an antibody bound to the substrate.

The oral composition may be typically useful for delivering the antibody to an appropriate site of action in the body by protecting the antibody from degradation as it passes via the stomach into the lower gastrointestinal tract and beyond. Accordingly, diseases, disorders and conditions of the stomach and lower gastrointestinal tract can be targeted for treatment by the composition of the present invention, including conditions such as gastritis, gastroenteritis, inflammatory bowel disease, irritable bowel syndrome, ulcerative colitis and Crohn's disease.

In another embodiment of the fifth aspect of the present invention, the composition is an ocular composition. That is, the composition is formulated for delivery to the eye. The composition can be formulated for delivery to the eye by any suitable means, including as a liquid "drop" or via intraocular injection as non-limiting examples. When formulated for intraocular injection, the composition may be directly implanted into the vitreous of the eye or may be applied to an intraocular lens. An ocular composition of the present invention may be used to treat a disease, disorder or condition of the eye, including the ocular conditions described above.

In a sixth aspect, the present invention provides a composition for administering an antibody to, and/or via, a proteolytic environment, the composition comprising a porous silicon substrate comprising mesoporous nanoparticles and/or mesoporous microparticles and an antibody bound to the substrate.

In another aspect, the present invention provides a composition for protecting an antibody from degradation in a proteolytic environment, wherein the composition comprises a porous silicon substrate comprising mesoporous nanoparticles and/or mesoporous microparticles and an antibody bound to the substrate.

In a seventh aspect, the present invention provides a composition for administering an antibody, the administering comprising exposing the composition to, and/or via, a proteolytic environment, wherein the composition comprises a porous silicon substrate and an antibody bound to the substrate.

In an eighth aspect, the present invention provides a composition for administering an antibody, the administering comprising exposing the composition to, and/or via, a proteolytic environment, wherein the composition comprises a porous silicon substrate comprising mesoporous nanoparticles and/or mesoporous microparticles and an antibody bound to the substrate.

In a ninth aspect, the present invention provides a composition comprising a porous silicon substrate and an antibody bound to the substrate, wherein the porous silicon substrate comprises a porosified silicon film produced from a crystalline silicon wafer by more than one etching step.

In another aspect, the present invention provide a composition for protecting an antibody from degradation in a proteolytic environment, wherein the composition comprises a porous silicon substrate and an antibody bound to the substrate, and wherein the porous silicon substrate comprises a porosified silicon film produced from a crystalline silicon wafer by more than one etching step.

In a tenth aspect, the present invention provides a composition comprising a porous silicon substrate and an antibody bound to the substrate, wherein the porous silicon substrate comprises mesoporous nanoparticles and/or mesoporous microparticles, wherein the mesoporous nanoparticles and/or mesoporous microparticles are produced by sonication of a porosified silicon film produced from a crystalline silicon wafer by more than one etching step.

In another aspect, the present invention provides a composition for protecting an antibody from degradation in a proteolytic; environment, wherein the composition comprises a porous silicon substrate and an antibody bound to the substrate, the porous silicon substrate comprising mesoporous nanoparticles and/or mesoporous microparticles, and wherein the mesoporous nanoparticles and/or mesoporous microparticles are produced by sonication of a porosified silicon film produced from a crystalline silicon wafer by more than one etching step.

In each of the previous aspects of the present invention, details regarding the composition, including the nature of the porous silicon substrate and the antibody are described above.

In a further aspect, the present invention provides a method of using a composition of any one of the aforementioned aspects of the invention to treat a disease, disorder or condition in, and/or via, a proteolytic environment. Such diseases, disorders or conditions are described in detail above.

In a further aspect, the present invention provides an antibody loaded onto a porous silicon substrate for use in delivering the antibody to, and/or via, a proteolytic environment.

In another aspect, the present invention provides a proteolytically stabilised antibody, wherein the antibody is bound to a porous substrate.

In another aspect, the present invention provides a composition comprising a proteolytically stabilised antibody, the composition comprising a porous substrate bound to the antibody.

In another aspect, the present invention provides a method of producing a proteolytically stabilised antibody, the method comprising binding a porous substrate to the antibody and thereby producing a proteoltyically stabilised antibody.

In another aspect, the present invention provides a proteolytically stabilised antibody produced by a method as described above.

In another aspect, the present invention provides a product comprising a proteolytically stabilised antibody as described above. In some embodiments, the product is a wound healing composition. In some embodiments, the product is a dressing or a bandage.

In another aspect, the present invention provides a composition comprising an antibody bound to a porous substrate, wherein the antibody comprises reduced degradation in a proteolytic environment.

In some embodiments, the antibody comprises a reduced degradation as compared to the antibody alone. Other methods of determining a reduced degradation are contemplated.

In some embodiments, the antibody comprises a reduced degradation of at least 10%, at least 20%, at least 30%, at least 40%, at least 50%, at least 60%, at least 70%, at least 80%, or at least 90%.

In a further aspect, the present invention provides a dressing or bandage comprising a composition of the fifth to twelfth aspects of the invention. The nature of the dressing or bandage is described in detail above.

The present invention also provides for methods of preparing the porous substrates described herein. As indicated above, porous silicon substrates are commonly produced from crystalline silicon wafers in hydrofluoric acid (HF) containing solutions by one of three methods: chemical stain etching, metal assisted etching and electrochemical etching. This step generates a porosified silicon film on the wafer that can be removed by further etching.

Accordingly, in a further aspect, the present invention provides a method of preparing a porous silicon substrate, the method comprising the steps of:
(i) providing a crystalline silicon wafer;
(ii) porosifying the crystalline silicon wafer to produce a porisified silicon film on a surface of the crystalline silicon wafer; and
(iii) removing the porisified silicon film from the crystalline silicon wafer by more than one etching step,
thereby preparing the porous silicon substrate.

Crystalline silicon wafers can be commercially purchased such as those of the p-type boron doped with a resistivity range of 0.00055-0.001 Ωcm and a <100> crystal orientation (Virginia Semiconductors, Fredericksburg, Va., USA) and those of the p-type boron doped with a resistivity range 0.0008-0.0012 Ωcm and a <100> crystal orientation (Siltronix, France).

In one embodiment, the crystalline silicon wafer is porosified electrochemical anodisation. This may involve cutting the wafer into 3 to 4 $cm^2$ pieces, washing the wafer pieces with high purity ethanol and placing them into a Teflon cell between two electrodes. A voltage is applied between the silicon wafer, acting as an anode, and a cathode (typically made of platinum) in an HF-containing electrolyte. In one embodiment, the electrolyte contains 3:1 HF:ethanol (v/v) solution. The voltage causes holes to appear on the silicon-electrolyte interface where it weakens a bond of a silicon atom which is then dissolved by HF. The pore formation comprises two processes, pore initiation and pore growth. The initial pore formation can take place at structural defects, mechanically strained areas or local perturbations of the surface potential field. Once the pores have been initiated the holes flow preferentially to the bottom of the pores where the dissolution of silicon takes place. The pore growth continues virtually as long as the voltage is being applied, producing a porous layer on the surface of the wafer. There are many parameters that can be used to control the electrochemical etching of porous silicon, including silicon doping, crystal orientation, electrolyte composition, current density, time, temperature and illumination.

Anodisation current and time is selected by the user according to the size of the pores required. For example, the current density may range from a few $mA/cm^2$ to 500 $mA/cm^2$ and the time of application of the current may range from a few seconds to hours. In some embodiments, the wafer is anodized with a current density of 222 $mA/cm^2$ for 4 minutes. In some embodiments, the wafer is anodized with an initial current density of 50 $mA/cm^2$ for 7.3 seconds and second current density of 400 $mA/cm^2$ for 0.4 seconds. This two-step cycle can be repeated continuously to generate a porous silicon film with alternating low and high porosity layers.

Once the silicon film has been porosified it is removed from the crystalline silicon wafer by more than one etching step. A single etching step can often result in non-homogeneous pore sizes and the formation of a microporous layer when etching some wafers that possess a highly doped surface. This microporous layer needs to be removed by a first etching step (a sacrificial etching step) to expose the desired porous layer beneath the microporous layer. A second etching step can then be utilised to obtain a porosified silicon film with the desired pore size characteristics.

In some embodiments, the first and second etching steps may be carried out with current densities ranging from a few $mA/cm^2$ to 500 $mA/cm^2$ and times for application of the current ranging from a few seconds to hours. In some embodiments, the first etching step may be carried out at 200 mA (113 $mA/cm^2$) for 15 seconds. In some embodiments, the second etching step may be performed with current densities ranging from 150 to 233 $mA/cm^2$ and etching times of 15 to 291 seconds.

As indicated above, various pore structures can be prepared by varying the etching parameters. In this way, materials with a pore size in the range of few nanometers (i.e. nanoporous silicon and mesoporous silicon) to several micrometers (i.e. microporous silicon and macroporous silicon), surface area from a few $m^2/g$ to 1000 $m^2/g$, and porosities between 5 and 95%, can be achieved.

As indicated above, the surface of freshly prepared porous silicon substrate is covered with hydrides which protect the highly reactive silicon structure against oxidation to some extent. However, the hydrogen terminated porous silicon oxidizes slowly at ambient conditions due to atmospheric oxygen and water vapor. Furthermore, hydride covered porous silicon rapidly oxidizes in water and can act as reducing agent which provides poor stabilization against dissolution in an aqueous environment. Therefore, it is important to stabilize the surface of the porous silicon substrate. The two most common ways to stabilize porous silicon are the formation of an oxide surface and stabilization by addition of carbon atoms.

Formation of an oxide surface can be achieved in one embodiment by thermal oxidation of the surface. Accordingly, the method of preparing a porous silicon substrate includes an oxidisation step (iv). In some embodiments, the porosified silicon film is oxidized at a temperature of about 400° C.

As indicated above, porous silicon produced by electrochemical etching is in the form of a thin film (from a few microns to a few hundreds of microns thick). Accordingly, a size reduction is necessary to produce a particulate form of the porous silicon. Comminution is typically achieved by ball milling, jet milling or sonication. After comminution, the particles typically show a wide size distribution from tens of nanometers (i.e. nanoparticles) to several micrometers (i.e. microparticles). The particles with desired size can be obtained through sieving or centrifuge separation.

Accordingly, in some embodiments, prior to the oxidation in step (iv), the porosified silicon film is subdivided into discrete particles. In some embodiments, the subdivision is performed by sonication. The intensity and duration of the sonication will dictate the size of the particles generated. The size of the particles generated is described in detail above.

In a further aspect, the present invention provides a porous silicon substrate prepared by the method described above.

In a further aspect, the present invention provides an antibody bound to a porous silicon substrate prepared by the method described above.

In a further aspect, the present invention provides mesoporous nanoparticles or mesoporous microparticles prepared by the method described above.

The term "about" as used in the specification means approximately or nearly and in the context of a numerical value or range set forth herein is meant to encompass variations of +/−10% or less, +/−5% or less, +/−1% or less, or +/−0.1% or less of and from the numerical value or range recited or claimed.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Finally, reference is made to standard textbooks of molecular biology that contain methods for carrying out basic techniques encompassed by the present invention. See, for example, Green M R and Sambrook J, *Molecular Cloning: A Laboratory Manual* (4th edition), Cold Spring Harbor Laboratory Press, 2012.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

The invention is further illustrated in the following examples. The examples are for the purpose of describing particular embodiments only and is not intended to be limiting with respect to the above description.

EXAMPLE 1

Surface Engineering of Porous Silicon to Optimise Therapeutic Antibody Loading and Release The studies described herein demonstrate the versatility of porous silicon (pSi) as a reservoir for antibody delivery in both in vivo and ex vivo applications in proteolytic environments. In this particular example, it is shown that Infliximab released from pSi MPs remained active in a proteolytic environment and was able to neutralise TNF-α (in accordance with the scheme shown in FIG. 1). This provides one example of an improved therapeutic delivery system for the treatment of chronic wounds and ocular conditions such as uveitis.

Experimental Details

Chemicals

Hydrofluoric acid (HF) 48% (Merck), dichloromethane ($CH_2Cl_2$, Labserv, analytical grade, 99.5%), methanol (Merck, analytical grade, 99.5%), acetone (Ajax, analytical grade, 99.5%), and ethanol (Ajax, absolute, 100%) were used without further purification. N,N-dimethylformamide (DMF, EMD Chemicals, Belgium) was purified via standard laboratory protocols including drying over $MgSO_4$ followed by distillation at reduced pressure. Milli-Q water was obtained from an Advantage A10 water purification system provided by Merck Millipore (water resistivity of 18.2 MΩcm at 25° C., TOC<5 ppb). Phosphate buffered saline (PBS) solution was prepared by dissolving one PBS tablet (Sigma) in 200 mL of MilliQ water, giving a pH of 7.4.

Infliximab (Remicade®) powder was purchased from Janssen, Australia. Each vial contains 100 mg of Infliximab, 6.1 mg of sodium phosphate dibasic dehydrate, 2.2 mg of sodium phosphate monobasic monohydrate, 500 mg of sucrose and 0.5 mg of polysorbate 80. The undiluted Infliximab powder was stored at 4° C. Before use the Infliximab powder was diluted to 1 mg/mL with MilliQ water (10 mL).

pSi Film Preparation

Si wafers (p-type boron doped with a resistivity range of 0.00055-0.001 Ωcm and a <100> crystal orientation) were cut in 3-4 $cm^2$ pieces, washed with high purity ethanol (Ajax, absolute, 100%) and placed into a Teflon cell, between two electrodes (a platinum mesh as cathode and an aluminum foil as anode for the back contact of Si). The exposed surface area was 1.767 $cm^2$ and the distance between the silicon and the Pt cathode was approximately 1.5 cm. A Keithley 2425 100 W Source Meter was used for anodisation. Etching current and time were controlled by a custom written Labview 8.2 computer program. Polished silicon wafers (CZ process, diameter of 76.2 mm and thickness between 475-525 µm) were provided by Siltronix. The wafer pieces were etched in a 3:1 HF:ethanol (v/v) solution. One sacrificial etching step was carried out at 200 mA (113 $mA/cm^2$) for 15 s and the freshly etched surface was washed with ethanol before treatment with 1 N sodium hydroxide for 1 min. The silicon surface was washed again with MilliQ water and ethanol and dried under nitrogen gas. The second etching process was performed with etching current densities ranging from 150 to 233 $mA/cm^2$ and etching times of 15 to 291 s. After etching, washes were performed with ethanol and dichloromethane and dried with nitrogen gas.

pSi MP Preparation

Microparticles were fabricated from p-type Si wafers (boron-doped, resistivity <0.001 Ωcm, <100>) supplied by Virginia Semiconductors (Fredericksburg, Va., USA). The wafer was anodized in an 18 $cm^2$ etching cell in 3:1 HF:ethanol (via) solution with a current density of 222 $mA/cm^2$ for 4 min, and then electropolished for 30 s at 500 $mA/cm^2$. Then, 20 min of sonication was performed (S30H Elmasonic, 280 W, Elma) to fracture the pSi membrane into MPs. The pSi MP suspension was filtered, washed with ethanol and dichloromethane before drying to completeness.

Gravimetric Analysis

The porosity of pSi was determined by weight measurements. To do this, the wafer is weighed before etching ($m_1$), after etching ($m_2$) and after the porous layer is dissolved from the bulk Si, with NaOH ($m_3$). These three values can then be used to calculate the porosity using the following equation:

$$\text{Porosity (\%)} = (m_1 - m_2)/(m_1 - m_2) \quad \text{equation (1)}$$

Zeta Potential

The surface zeta ($\zeta$)-potential of pSi MPs was determined by using a disposable zeta potential cell on a Zetasizer Nano ZS (Malvern instruments). The analysis was carried out at a temperature of 25° C. using pSi MPs dispersed in PBS buffer at pHs ranging from 5.5 to 8.5. Zeta potential was acquired from 50 runs performed in triplicate for each sample.

Thermal Oxidation

A Labec horizontal tube furnace (heating rate of 20° C./min) was used to thermally oxidise the freshly etched pSi. Samples being oxidized were situated in the middle of the furnace and the ends of the tube were closed with ceramic caps. Various oxidation temperatures (300, 400 and 500° C.) were used. All thermal oxidations commenced at room temperature and the furnace was ramped to the desired temperature before remaining at that constant temperature for 1 h. The pSi samples were allowed to slowly cool to room temperature inside the furnace. The oxidized films were cut in two smaller pieces leaving out the nm of the etched area. The pieces were then washed in ethanol and dried with nitrogen gas before being loaded with Infliximab (see loading section below).

Time-of-Flight Secondary Ion Mass Spectrometry (TOF-SIMS)

ToF-SIMS measurements were performed using a Physical Electronics Inc. PHI TRIFT V nanoToF instrument (Chanhassen, Minn., USA) equipped with a pulsed liquid metal Au$^+$ primary ion gun (LMIG), operating at 30 kV. The extractor current of the ion source was maintained at 3 µA. Positive ion ToF-SIMS images (200 µm×200 µm) were acquired on the unloaded and Infliximab-loaded oxidized porous silicon macro-particles using 'unbunched' Au1 beam settings to deliver optimized spatial resolution. Positive ion mass spectra (200 µm×200 µm) were acquired on the same surfaces using a 'bunched' Au1 beam setting for optimal mass resolution. The acquisition time for both images and spectra was 5 min each. Mass calibration of the spectra was done with $CH_3^+$, $C_2H_5^+$, and $C_3CH_7^+$ ions. Experiments were performed a high vacuum (<10$^{-8}$ Torr), in static mode (i.e. below 10$^{12}$ ions/cm$^2$) to minimise sample damage.

Infrared Spectroscopy

Attenuated total reflectance infrared (ATR-IR) spectra were obtained using a Bruker Hyperion 1000 IR microscope operating with a Bruker Vertex 80 IR spectrometer. The IR microscope was equipped with a liquid nitrogen cooled MCT detector. ATR spectra were collected over 64 scans, with a resolution of 4 cm$^{-1}$, using a Ge ATR crystal. All spectra were background corrected with an unetched silicon wafer of the same type. Spectra of the pSi layers were recorded and analysed using OPUS version 7.0 software, in the range of 650-4000 cm$^{-1}$. All IR spectra are presented with absorbance normalized to the Si—O peak at approximately 1100 cm$^{-1}$.

Scanning Electron Microscopy (SEM)

SEM was performed on a FEI Quanta 450 FEG environmental SEM fitted with an SSD detector, and operated at 30 keV with a spot size of 2 mm. To help facilitate the dissipation of charge build-up, samples were coated with 5 nm thick layer of Pt prior to analysis, according to our standard laboratory protocol (S. P. Low, N. H. Voelcker, L. T. Canham, and K. A. Williams, *Biomaterials*, 2009, 30, 2873-2880). pSi MPs were dispersed directly onto conductive aluminium stubs for analysis, and were not coated for analysis.

Loading and Quantification of Infliximab

Infliximab powder was dissolved in 10 mL of sterile MilliQ water for injection, giving a drug concentration of 10 mg/mL. The solution was subsequently diluted out in PBS to achieve a working concentration of 1 mg/mL. The antibody solution was aliquated and stored at −80° C. The loading of Infliximab (1 mg/mL, pH 7.4) into the oxidized pSi MPs was carried out using a sealed low protein binding Eppendorf tube. After loading the MPs were rinsed with PBS (pH 7.4, 15 min) to remove the weakly adsorbed antibody. The amount of protein loaded was determined from UV-Vis measurements of the supernatant before and after incubation with the pSi MPs.

Interferometric Reflectance Spectroscopy (IRS) of pSi Films

IRS was used to monitor the effective optical thickness (EOT) of the pSi layer in time-lapse mode. The experiments were performed using an interferometer with a bifurcated fiber on a motorized stage that allowed the same sample spots to be accurately analysed. The interferometer consisted of a tungsten light source and USB2000 CCD Detector (Ocean Optics, USA). For the EOT comparison, pSi substrates were placed directly on the motorized stage and monitored in air. For degradation studies, the pSi substrates were placed in a custom-built cell (as described in E. J. Szili, A. Jane, S. P. Low, M. Sweetman, P. Macardle, S. Kumar, R. S. C. Smart, and N. H. Voelcker, *Sensor. Actuat. B: Chem.*, 2011, 160: 341-348) that allowed solutions to be flowed over the sample while monitoring the EOT in real time.

Infliximab Release (Using ELISA and L929 Assay)

Infliximab loaded pSi-MPs (15 mg) were incubated in 500 µL PBS, pH 7.2, for 2 weeks at 25° C., to more closely mimic the skin surface temperature, which can vary significantly especially when wounded. At days 1, 2, 7, 14, 21 and 28 days, samples were spun briefly to pellet the pSi and then all of the supernatant was decanted. A 500 µL aliquot of fresh PBS, pH 7.4, was added to each sample, to continue the incubation. Each aliquot was tested for the amount of antibody release via ELISA (see section, TNF-α ELISA, below) and TNF-α based bioassay (see section, TNF-α cell-based bioassay, below).

Infliximab Release (Using Fluorimetry)

Infliximab (0.1 mg/mL) was labeled with fluorescein isothiocyanate (FITC) for 4 h in a sodium carbonate buffer (100 mM, pH 9.5). After labeling the labeled protein was recovered using a Vivaspin 2 10,000 MWCO spin tube (Sartorius Stedim) according to the manufacturer's instructions. This FTC labeled protein was then added to unlabeled Infliximab at a ratio of 1:5.85 and this stock was used to load pSi MPs as outlined above. Release was then monitored on an Agilent Technologies Cary Eclipse fluorimeter fitted with a Peltier temperature control system with a PMT of 650 V and excitation and emission slit widths of 5 nm. The emission was monitored at 525 µm and the excitation was performed at 490 nm. Data was recorded in an automated kinetic mode every 8 h for 7 d. The FITC signal was calibrated against a calibration curve constructed from dilutions of the FITC labeled Infliximab stock solution.

TNF-α ELISA

The Duo TNF-α ELISA kit (R&D Systems) was used to detect non-neutralized human TNF-α as per the manufacturer's instructions. TNF-α was evaluated in post-pSi supernatant and TNF-α spiked (1 µg/mL) acute wound fluid (obtained with institutional ethics approvals Human Research Ethics Committee, The Queen Elizabeth Hospital, Lyell McEwin Hospital, Modbury Hospital (TQEH/LMH/MH) Ref #: HREC/12/TQEHLMH/107). The optical density of each well was determined immediately using a microplate reader set to 450 nm (Sunrise™, Tecan Group Ltd., Australia).

TNF-α Cell-Based Assay

A cell-based cytotoxic bioassay based on a subclone of the murine L929 fibroblast cell line (Sigma-Aldrich, Sydney, Australia) was used. Briefly, L929 cells were seeded at $2 \times 10^4$ cells per well in 96-well microtiter plates containing 50 μL of culture medium (Dulbecco's modified Eagle's medium containing 10% (v/v) fetal bovine serum) (Sigma-Aldrich, Sydney, Australia). The cells were incubated for 24 h before the addition of 50 μL test solution, containing from 1 mg/mL to 1 pg/mL recombinant human TNF-α (R&D Systems, Minneapolis, Minn.), and Infliximab released from pSi MPs to each well. Fresh Infliximab (1 to 1000 μg/mL) was added to some wells as a positive control. After a further 24 h incubation, 20 μL of 2.5 mg/mL 3-(4,5-dimethyithiazol-2-yl)-2,5-diphenyl tetrazolium bromide (MTT; Sigma-Aldrich, Sydney, Australia) and 50 μL culture medium was added per well and incubated for 4 h before solubilisation in 100 μL/well 10% (w/v) sodium dodecyl sulfate-HCl. After a final overnight incubation, the blue formazan product was measured at 570 nm on a microplate reader (Sunrise™, Tecan Group Ltd., Australia).

Statistical Analysis

Statistical differences were determined using the Student's t-test or an ANOVA. For data not following a normal distribution, the Mann-Whitney U-test was performed. A P value of less than 0.05 was considered significant.

Results

Infliximab (molecular weight of 149 kDa) has a hydrodynamic radius of 5-6 nm and an isoelectric point (pI) of approximately 8.3. The radius and the pI dictate that a >10 nm pore radius and a negative surface charge at neutral pH should be used to facilitate antibody loading and retention. When working with monoclonal antibodies, using a buffer with the correct pH and ionic strength is important. As the pI of Infliximab is 8.3 working at pH 7.4 which is below this pI should keep the Infliximab positively charged and subsequently less likely to aggregate, hence, helping the protein to remain in its fully active conformation.

The original pSi etching conditions were adapted from previous studies, although we observed that these conditions resulted in non-homogeneous pore sizes and a microporous layer formed when etching some wafers that possess a highly doped surface layer. In order to remove this microporous layer, a sacrificial etching step (a first etching step) was applied (FIG. 2). After the sacrificial etching step, etching current densities from 2:33 to 150 mA/cm$^2$ were used in combination with etching times from 15 to 240 s. Interferometric reflectance spectroscopy (IRS) analysis of the effective optical thickness (EOT) from 20 locations on each film showed that the 233 mA/cm$^2$ etch for 20 s produced the most homogeneous surfaces with EOT variations of less than 0.20% across the scanned etched region (FIG. 3).

Figure 4A:
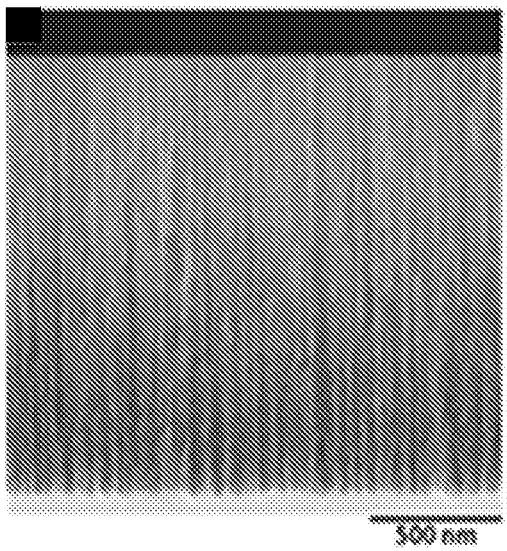
FIG. 4—shows scanning electron microscopy (SEM) images of (A) a cross-sectional view and (B) a top down view of an oxidized (400° C.) pSi film.
Figure 4B:
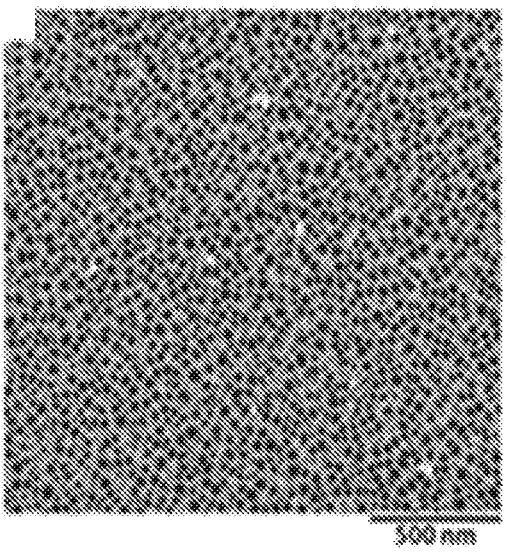

Scanning electron microscopy (SEM) images of the pSi surfaces etched using the optimal conditions of 233 mA cm$^{-2}$ for 20 s and oxidized at 400° C. (FIG. 4) revealed pore sizes are approximately 22.2±4.4 nm. The thickness of the porous layer, measured via SEM, was 1.39 μm and the porosity, determined by means of IRS, was 76±5%.

The temperature at which the pSi film surface is oxidized controls both the extent of antibody loading (assuming that a larger difference in net charge between the pSi surface and antibody encourages more protein binding), and the rate at which the pSi will degrade in aqueous buffers. pSi Functionalized at 600° C. or above will not readily degrade in aqueous solutions either in vitro or in vivo. For this reason, we chose to investigate oxidation temperatures of 300, 400 and 500° C. with freshly etched pSi as a control. FIG. 5 shows the average degradation curves for each oxidation temperature over a 2 h period. Combining this analysis with the pre-determined film thickness, we can estimate the expected degradation time. As anticipated, the fastest surface to degrade was the freshly etched pSi surface at a rate of 18.13% EOT/h, resulting in complete degradation of the film in just 2.5 h (0.10 d). The time for degradation of the films oxidized at 300° C. extended to 73.8 h (3.1 d at a rate of 0.61% EOT/h). This degradation time increased further to 201.3 h (8.4 d at 0.22% EOT/h) for the film oxidized at 400° C. and to 790.0 h (32.91 d at 0.06% EOT/h) for the sample after 500° C. oxidation.

The optimal etching conditions were then used to produce pSi MPs that were thicker in nature than the pSi films (FIG. 6) and could be suitable for either implantation or injection. pSi MPs were etched using the conditions adapted from those optimized for the pSi films, with an etching time of 4 min and a subsequent 30 s electropolish at 500 mA/cm$^2$ to lift off the film, which was then subsequently sonicated to generate particles. SEM revealed that the pSi MPs had a thickness of 23.4±1.3 μm (FIG. 6A). Higher resolution SEM analysis showed an average pore diameter of 19.5±8.2 nm (FIG. 6B), very similar to that of the pSi films (22.2±4.4 nm, FIG. 4B). Typical particle sizes were in the range of 66.5±20.9 μm. Gravimetric analysis determined the porosity of the pSi MPs to be 84.2±2.0%, again very close to that of the pSi film preparations (76±5%).

Zeta potential investigations into the pSi MPs prepared with various oxidation conditions at pH 7.4 revealed that the surface was negatively charged at about –20 mV for all oxidation temperatures (see Table 2).

TABLE 2

Zeta potential measurements of pSi MP surfaces oxidized at different temperatures in PBS at pH 7.4 (n = 3).

| pSi Oxidation Temperature (° C.) | Zeta Potential (mV) |
|---|---|
| 300 | −20.3 ± 0.9 |
| 400 | −19.4 ± 1.5 |
| 500 | −20.3 ± 1.7 |

This is in line with the literature and is attributed to the presence of Si—OH on the surface. Next, Infliximab binding was analysed overnight at room temperature by observing the change in zeta potential of the pSi MPs before and after the injection of Infliximab at 266 μg/mL (FIG. 7A).

It was observed that the zeta potential of the MPs after overnight incubation decreased significantly for all oxidation conditions, due to the adsorption of protein. Loading of the Infliximab into the pSi MPs during the zeta measurements was also confirmed by the UV-Vis spectroscopy of the supernatant before and after the loading experiment. The supernatant after loading showed complete removal of the protein peak at 2.80 nm (FIG. 7B), suggesting that the protein was completely sequestered by the pSi MPs.

Considering the degradation and zeta potential data, we chose to use 400° C. oxidized pSi MPs to perform binding Infliximab experiments since this sample was stable over several days (the desired timeframe of drug release) and was negatively charged where Infliximab at pH 7.4 is positively charged.

Antibody loading experiments performed at pH 6.5 and 5.5 showed a similar trend in both zeta potential measurements and UV-Vis analysis (FIG. 8), suggesting no advantage of loading at more acidic pH values. Subsequently, our typical loadings of the pSi MPs were performed with approximately 15 mg of pSi and 1 mg (at 1 mg/mL) Infliximab in PBS at 7.4. Loading values were individually assessed by UV-Vis spectrophotometry of the supernatant before and after for each particle preparation used, and were typically in the range of 0.063±0.010 mg/mg similar to literature values. Loadings could be further improved by the use of higher concentrations of Infliximab (Table 3).

TABLE 3

Loading of Infliximab at concentrations >1 mg/mL

| Infliximab Concentration (mg/mL) | Loading (mg/mg) | Loading Efficiency (%) |
|---|---|---|
| 1.0 | 0.063 ± 0.010 | 94.5 |
| 2.4 | 0.159 ± 0.010 | 85.0 |
| 5.2 | 0.225 ± 0.004 | 65.0 |
| 8.3 | 0.321 ± 0.004 | 58.3 |

Figure 9:
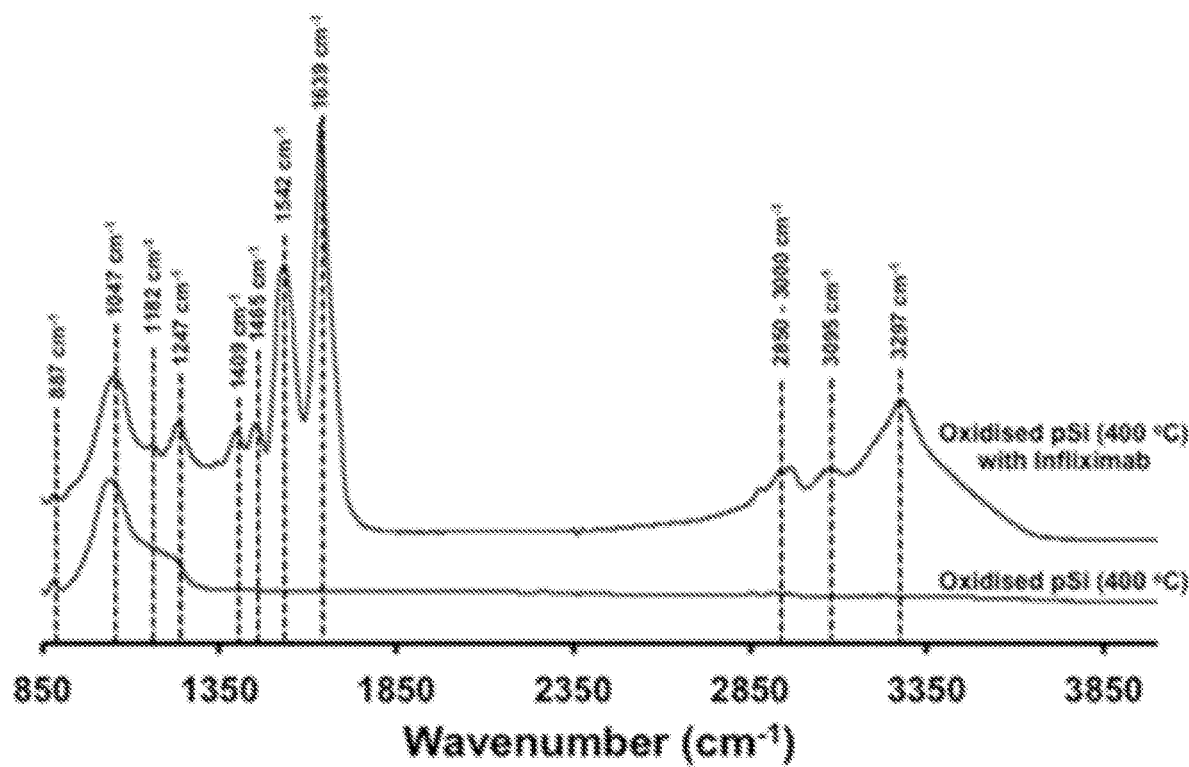
FIG. 9—shows ATR-IR spectra of pSi film oxidized at 400° C. before and after loading of Infliximab.

Successful loading of Infliximab was also confirmed by infrared (IR) spectroscopy. The IR in attenuated total reflection (ATR) spectra of oxidized pSi (FIG. 9, 400° C. oxidized pSi) showed a broad, intense peak centered at 1047 cm$^{-1}$ attributed to the asymmetric stretching of Si—O—Si groups and at 887 cm$^{-1}$ due to Si—O bending in O—Si—O. The shoulder located at approximately 1182 cm$^{-1}$ was attributed to the stretching of surface oxide species including O—Si—O. After loading of Infliximab, into the oxidized pSi (FIG. 9, 400° C. oxidized pSi with Infliximab), the spectra still showed surface peaks characteristic of oxidized pSi in addition to new peaks at 1465 cm$^{-1}$ from the asymmetric CH$_3$ deformation and dual peaks at 2850-3000 cm$^{-1}$ for the C—H stretching vibrations of the protein. Two prominent peaks at 1542 cm$^{-1}$ and 1639 cm$^{-1}$ were attributed to C—N—H bending vibrations (amide II) and C=O stretching vibrations (amide I) of the peptide bonds, respectively. The 1247 cm$^{-1}$ peak could also be ascribed to amide III of the protein,[81] while the secondary amine (N—H) stretching appeared at 3290 cm$^{-1}$. The IR results therefore confirm the presence of Infliximab on the pSi surface. X-ray photoelectron spectroscopy (XPS) further corroborated those results (Table 4).

TABLE 4

At. % of loaded and non-loaded oxidized pSi surfaces

| Sample/Element | Non-loaded Oxidized pSi | Loaded Oxidized pSi |
|---|---|---|
| Si 2p | 42.26 | 31.56 |
| O 1s | 46.54 | 40.07 |
| C 1s | 11.19 | 24.75 |
| N 1s | 0.00 | 3.62 |

Figure 11A:
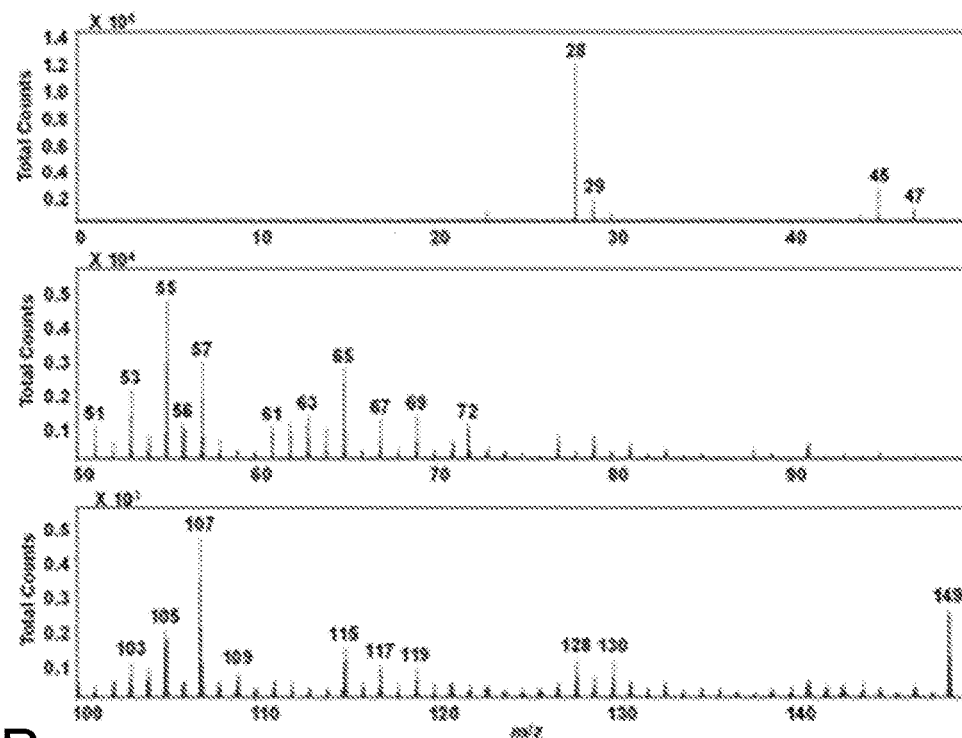
FIG. 11—shows positive ion ToF-SIMS mass spectra (0-150 m/z) for (A) unloaded and (B) Infliximab-loaded pSi MPs.
Figure 11B:
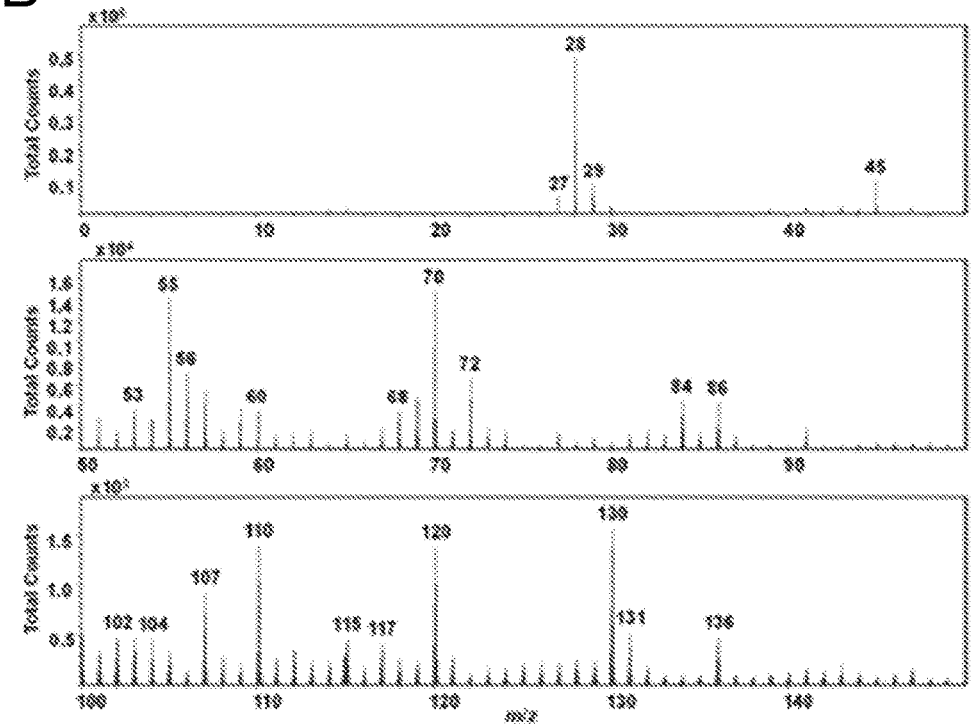

To verify that Infliximab diffused completely through the oxidized pSi layer, the cross-sections of pSi films before and after Infliximab loading were imaged by time-of-flight secondary ion mass spectrometry (ToF-SIMS) to detect characteristic positive ion fragments, appearing in the mass spectra after loading Infliximab into pSi. FIG. 10 shows ToF-SIMS images of the total positive ions and the total intensity of the selected positive ion fragments C$_4$H$_{10}$N$^+$ (m/z 72.081) and C$_5$H$_{12}$N$^+$ (m/z 86.096) characteristic of the amino acids valine and leucine/isoleucine, respectively (see FIG. 11 for ToF-SIMS mass spectra and Table 5 for Mass peak assignments).

TABLE 5

Positive ion fragments of Infliximab detected on loaded pSi-Ox surfaces and their corresponding amino acids over mass range 0-150 m/z.

| Mass (m/z) | Positive fragment | Amino acid |
|---|---|---|
| 30.036 | CH$_4$N | Glycine, Lysine |
| 44.049 | C$_2$H$_6$N | Alanine |
| 56.05 | C$_3$H$_6$N | Lysine |
| 59.05 | CH$_5$N$_3$ | Arginine |
| 60.054 | C$_2$H$_6$NO | Serine |
| 61.018 | C$_2$H$_5$S | Methionine |
| 68.05 | C$_4$H$_6$N | Proline |
| 69.043 | C$_4$H$_5$O | Threonine |
| 70.029 | C$_3$H$_4$NO | Asparagine |
| 70.066 | C$_4$H$_8$N | Proline, arginine |
| 71.014 | C$_3$H$_3$O$_2$ | Serine |
| 72.081 | C$_4$H$_{10}$N | Valine |
| 73.064 | C$_2$H$_7$N$_3$ | Arginine |
| 74.067 | C$_3$H$_8$NO | Threonine |
| 81.054 | C$_4$H$_5$N$_2$ | Histidine |
| 82.052 | C$_4$H$_6$N$_2$ | Histidine |
| 83.052 | C$_5$H$_7$O | Valine |
| 84.054 | C$_4$H$_6$NO | Glutamine, Glutamic acid |
| 84.088 | C$_5$H$_{10}$N | Lysine |
| 86.097 | C$_5$H$_{12}$N | Leucine, isoleucine |
| 87.06 | C$_3$H$_7$N$_2$O | Asparagine |
| 88.046 | C$_3$H$_6$NO$_2$ | Asparagine, aspartic acid |
| 91.055 | C$_7$H$_7$ | Phenylalanine |
| 98.019 | C$_4$H$_4$NO$_2$ | Asparagine |
| 100.089 | C$_4$H$_{10}$N$_3$ | Arginine |
| 101.091 | C$_4$H$_{11}$N$_3$ | Arginine |
| 102.058 | C$_4$H$_8$NO$_2$ | Glutamic acid |
| 104.062 | C$_4$H$_{10}$NS | Methionine |
| 107.059 | C$_7$H$_7$O | Tyrosine |
| 110.077 | C$_5$H$_8$N$_3$ | Histidine, arginine |
| 120.089 | C$_8$H$_{10}$N | Phenylalanine |
| 127.1 | C$_5$H$_{11}$N$_4$ | Arginine |
| 130.073 | C$_9$H$_8$N | Tryptophane |
| 131.055 | C$_9$H$_7$O | Phenylalanine |
| 132.064 | C$_9$H$_8$O | Phenylalanine |
| 136.083 | C$_8$H$_{10}$NO | Tyrosine |

As expected, no signal was detected for the C$_4$H$_{10}$N$^+$ & C$_5$H$_{12}$N$^+$ positive fragments within the oxidized porous layer of the unloaded sample. In contrast, both positive ion fragments were observed after Infliximab loading. The ToF-SIMS imaging also showed that the protein was present throughout the porous layer although signal intensity decreased with increasing depth. It should be noted that in order to facilitate the ToF-SIMS imaging, a very thick pSi film (80 μm) was used, much thicker than what was used for pSi MPs (23.4 μm). Indeed, ToF-SIMS imaging of oxidized pSi MPs after loading with Infliximab showed representative positive ion fragments, C$_4$H$_{10}$N$^+$ (m/z 72.081) and C$_5$H$_{12}$N$^+$ (m/z 86.096) over across the MPs (FIG. 12). As expected, however, mapping these fragments on the unloaded oxidized pSi MPs showed a very weak intensity. While it was impractical to cross-section the oxidized pSi MPs, we expected MPs with open pores on both sides would allow antibody loading easier than pSi films.

To obtain the antibody release kinetics from the 400° C. pSi MPs, we followed the emission of FITC-labeled Infliximab releasing into solution via fluorimetry (FIG. 13A). The release kinetics appeared initially to show a small burst release (approx. 5.3% at 8 h) followed by a near linear release profile ($R^2=0.976$) release profile. This is desirable to maximise the therapeutic benefits of a localized drug delivery platform. It was observed that the optimally loaded pSi MPs released the Infliximab at a rate of 22.56 μg of Infliximab per day. These results show that the release of Infliximab should continue for approximately 14 d (47.34% release observed at 7 d).

To test the functionality of the Infliximab released from the pSi MPs oxidized at 400° C., we carried cut a TNF-α neutralisation ELISA periodically over 14 d. Infliximab released from pSi was functional with >90% TNF-α neutralisation observed for the day 1 and 2 samples (FIG. 13B, black bars). However, the activity of the released Infliximab diminished over time, with no effect observed past the day 7 time-point, Infliximab functionality when incubated in the absence of pSi (FIG. 13B, grey bars) (at an equivalent concentration to the amount released from pSi) was less than observed for antibody released from pSi, with no activity detected after the 2 day time-point. This indicated that the incubation of low concentrations of Infliximab in PBS at 25° C. leads to degradation, providing a limitation for the assay, but importantly provided evidence that pSi protected Infliximab from degradation prior to release.

Figure 14:
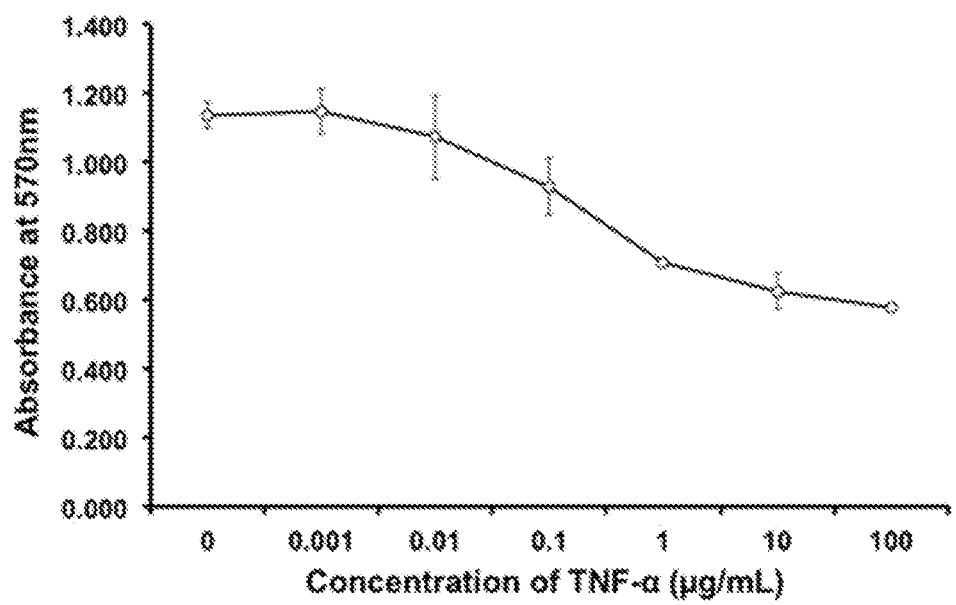
FIG. 14—shows a MTT assay to determine the viability of TNF-α-treated L929 cells. Increasing doses of human TNF-α were added to L929 cells, with viability measured using the absorbance at 570 nm. Data is presented as mean+/− one standard deviation (n=4).
Figure 15:
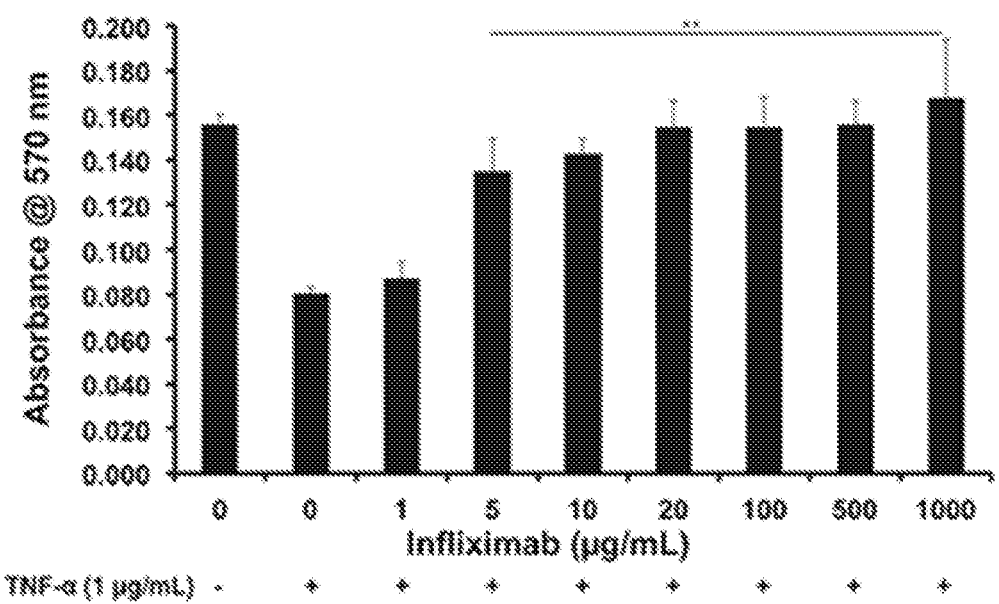
FIG. 15—shows a MTT assay to measure Infliximab-induced recovery of TNF-α-treated L929 cells. Increasing concentrations of Infliximab were incubated with 1 μg/mL human TNF-α for 10 minutes at 37° C., and then added to L929 cells. A MTT assay was used to measure L929 cell viability using absorbance at 570 nm. Data is presented as mean+/− one standard deviation (n=4).
Figure 16A:
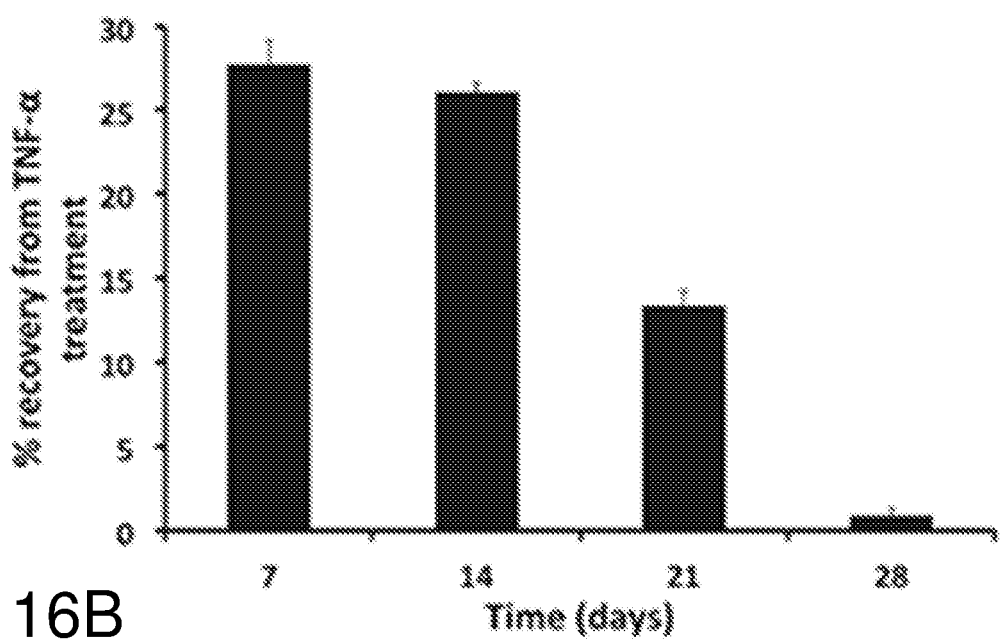
FIG. 16—shows recovery of TNF-α-treated L929 cell viability with Infliximab released from pSi. In panel (A), supernatant from Infliximab-loaded pSi MPs incubated at 25° C. in PBS was incubated with human TNF-α for 10 minutes at 37° C., and then added to L929 cells. In panel (B), supernatant from Infliximab-loaded pSi MPs incubated at 25° C. in acute wound fluid was incubated with human TNF-α for 10 minutes at 37° C., and then added to L929 cells. A MTT assay was used to measure L929 cell viability using absorbance at 570 nm. Data is presented as a % recovery of L929 cells as determined by the difference in signal between TNF-α-treated (0%) and TNF-α/Infliximab-treated (100%) cells. The assay was performed in triplicate and presented as mean+/− one standard deviation.

To confirm that Infliximab released from pSi MPs neutralises TNF-α whilst showing efficacy in a cellular environment, a L929 cell bioassay was used (Sugarman B J et al., 1985, Science, 230: 943-945; Cowin A J et al., 2006, Wound Repair Regen, 14: 421-426). Recovery of TNF-α treated L929 cells was assessed after 7, 14, 21 and 28 d of release. Recombinant TNF-α was cytotoxic to L929 cells in a dose dependent manner ($p<0.005$) (FIG. 14) and this cytotoxicity could subsequently be inhibited by Infliximab at ≥5 μg/mL. (FIG. 15). The addition of supernatant from Infliximab-loaded pSi MPs was demonstrated to increase L929 cell viability for up to 21 d (FIG. 16A). It should be noted that the MTT assay (FIG. 16A) showed the presence of functional Infliximab in samples up to day 28, longer than could be detected by ELISA (FIG. 13B). The discrepancy may be caused by differences in the sensitivity of these two assays and variations in the strength of TNF-α/Infliximab binding due to the different buffers, pH values and incubation times required. Together, the ELISA and L929 cell bioassay was able to confirm that Infliximab released from pSi MPs remained both stable and active.

Figure 16B:
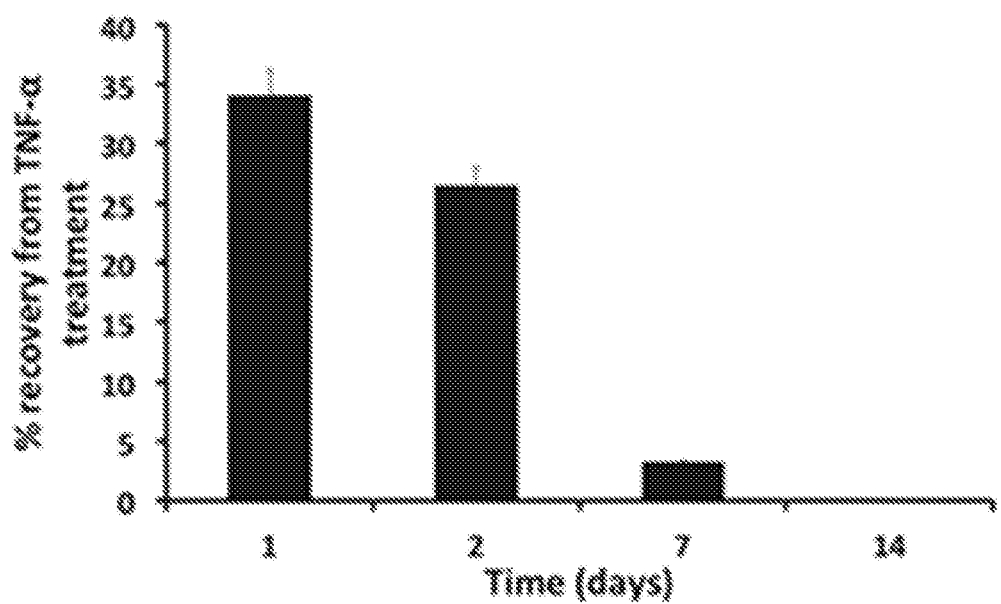
Figure 17A:
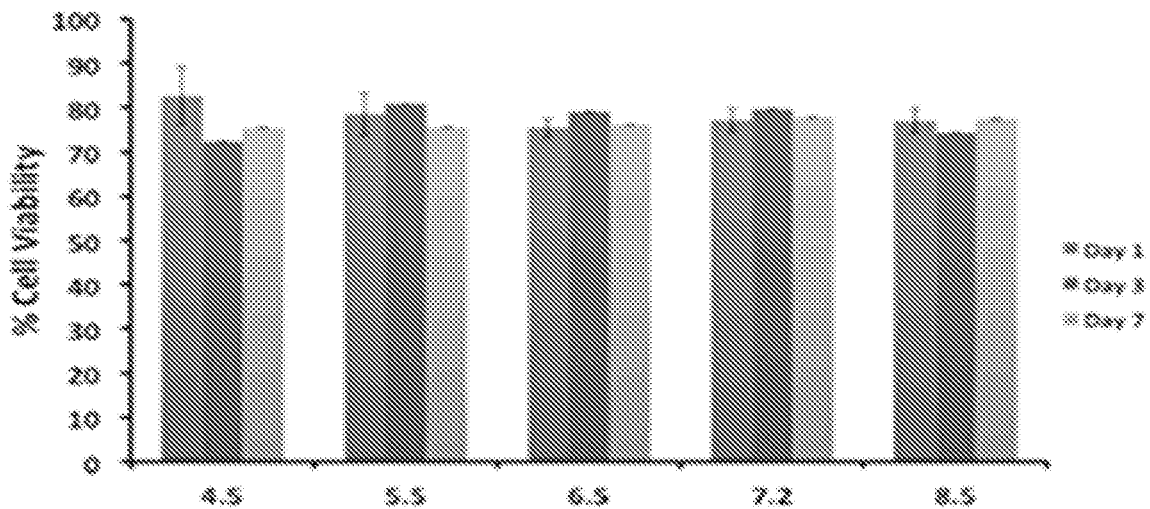
FIG. 17—shows the effect of pH and temperature on the functionality of Infliximab (1 mg/mL) was incubated in pH adjusted PBS at 4° C. (A), 25° C. (B) and 37° C. (C). Samples were then incubated with 1 μg/mL human TNF-α for 10 minutes at 37° C., and then added to L929 cells. MTT assay was used to measure L929 cell viability using absorbance at 570 nm. Data is presented as mean+/− one standard deviation (n=3). Data is presented as a % of cell viability at Day 1 (left colums), Day 3 (middle columns), and Day 7 (right columns).
Figure 17B:
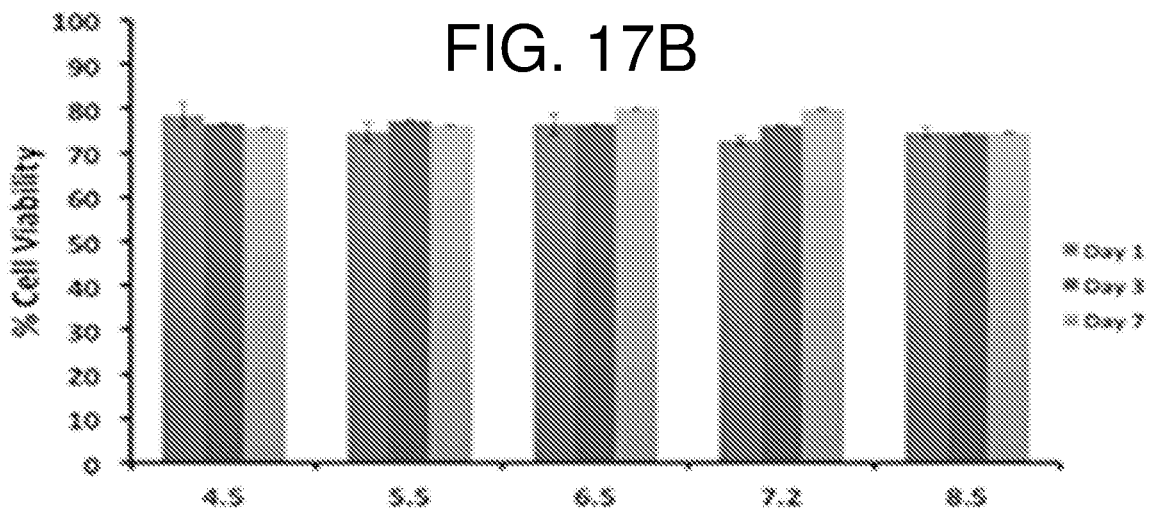
Figure 17C:
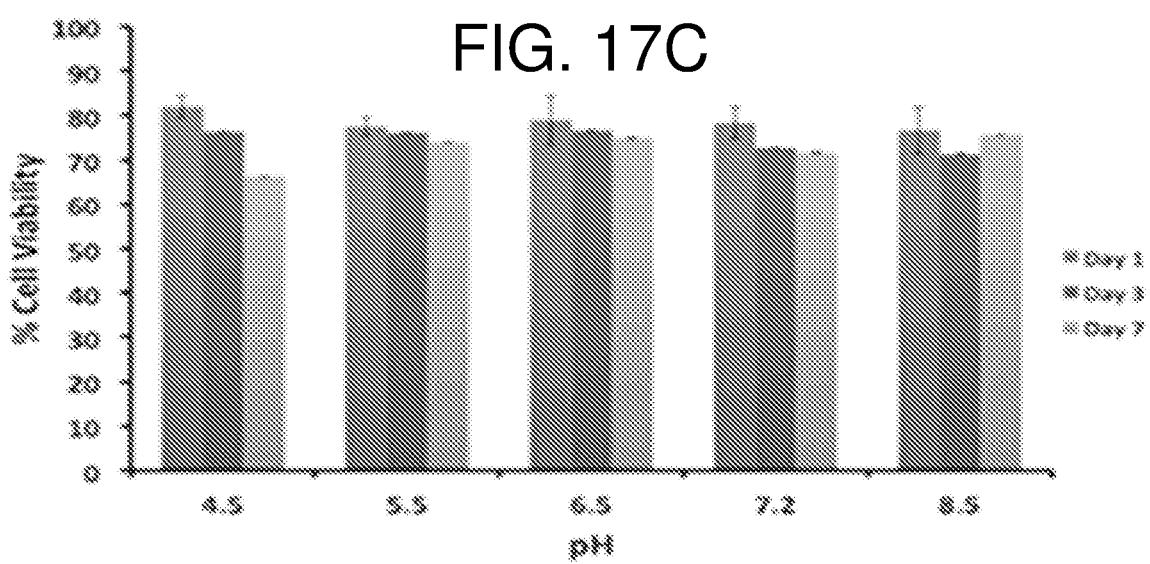

The applicability of this system with conditions closer to a wound environment was demonstrated via the neutralisation of TNF-α spiked into acute wound fluid (AWF) from 3 different patients (FIG. 16B). Time points of 1, 2, 7 and 14 d were analysed with the L929 cell bioassay. L929 cells could recover >25% when exposed to supernatant incubated for 1 and 2 d. This result suggests that the pSi MPs loaded with Infliximab were able to neutralise the TNF-α in actual wound fluid samples. Additionally, the range of conditions in which Infliximab remained active was tested via the L929 assay. We observed that the L929 cells were able to respond to Infliximab treatment when high concentrations (1 mg/mL) of Infliximab were held at pH values ranging from 4.5-8.5 and temperatures ranging from 4° C. to 37° C. for up to 7 d (FIG. 17). It was observed that even at the extreme pH values and temperatures approximately 70% cell recovery was observed.

The data presented here demonstrates that Infliximab is able to bind to TNF-α in a wound environment and subsequently reduces its activity. These results suggest the wide range and applicability of the delivery of Infliximab for applications ranging from wound healing to uveitis.

Conclusions

We demonstrate that oxidized pSi films and MPs have a high loading capacity for Infliximab and extend antibody release in vitro. In particular, we show near linear release kinetics of Infliximab from oxidized pSi MPs over 8 days. The released Infliximab was able to improve the viability of L929 cells for a 7-day period by mopping up the TNF-α in acute wound fluid, an adequate period of time to suit a clinical application.

These experiments support the use of porous silicon substrates as a resorbable and biocompatible therapeutic carrier for antibody administration. The substrate not only allows delivery of an antibody to a proteolytic environment, but allows for extended antibody delivery applications. This is further evidenced by Example 2 below. It is envisaged that pSi MPs can be incorporated into wound dressings materials and deliver Infliximab to wound fluid in order to improve chronic wound healing. The same Infliximab-releasing Si MP format would be suitable for the purpose of treating uveitis.

EXAMPLE 2

Delivery of Flightless I Neutralising Antibody from Porous Silicon Nanoparticles Flightless I (FIii) is elevated in human chronic wounds and is a negative regulator of wound repair. Decreasing its activity improves healing responses. Flii neutralising antibodies (FnAbs) have been developed that decrease FIii activity in vivo and hold significant promise as healing agents. However, in order to avoid the need for repeated application in a clinical setting, and to protect the therapeutic antibody from the hostile environment of the wound, suitable antibody delivery vehicles are required.

The study in this Example therefore aims to demonstrate the versatility of porous silicon (pSi) as a reservoir for FnAb delivery to diabetic wounds. We propose a system where FnAb is delivered from pSi protecting the antibody from the corrosive wound environment, providing an improved therapeutic delivery system for the treatment of chronic wounds.

Experimental Details

Chemicals

Hydrofluoric acid (HF) 48% (Merck), dichloromethahe ($CH_2Cl_2$, Labserv, analytical grade, 99.5%), methanol (Merck, analytical grade, 99.5%), acetone (Ajax, analytical grade, 99.5%), and ethanol (Ajax, absolute, 100%) were used without further purification. N,N-dimethylformamide (DMF, EMD Chemicals, Belgium) was purified via standard laboratory protocols including drying over $MgSO_4$ followed by distillation at reduced pressure (Armarego W, Perrin D. Purification of laboratory chemicals, 4th ed: Butterworth-Heinemann; 1996), Milli-Q water was obtained from an Advantage A10 water purification system provided by Merck Millipore (water resistivity of 18.2 MΩcm at 25° C. TOC<5 ppb). Dulbecco's phosphate buffered saline (PBS) solution, streptozotocin (STZ), bovine serum albumin (BSA), o-phenylenediamine dihydrochloride (OPD) substrate, pepsin from porcine gastric mucosa and fluorescein isothiocyanate (97.5%, FITC) were purchased from Sigma Aldrich and used as received. cOmplete, Mini protease inhibitor cocktail tablets and WST-1 were from Roche, Insulin (2 IU Protaphane/Mixtard) was purchased from Novo-Nordisk Isofluorane (Forthane) was from AbbVie.

Antibodies and Peptides

Affinity purified mouse monoclonal FnAb was prepared in house. To create FnAb, mice were immunised for with a 15-mer peptide unique to the Flightless I protein (CQKLE-HLSVSHNNLT—amino acids 56 to 69 of variant 1—SEQ ID NO: 9). The spleen was extracted from humanely killed mice and splenocytes were isolated and maintained in culture. Splenocytes were fused with myeloma cells to create hybridomas using polyethylene glycol and then seeded one cell per well in 96-well plates and allowed to divide in culture. Culture supernatant was decanted from each well for testing by ELISA, allowing the detection of IgG antibodies with specificity to the FIii peptide (FnAb, clone (G12). Positive clones were cultured in cell factories, with the supernatant collected for FnAb purification. FnAb was purified using a protein G column on a Bio-Rad chromatography system, with the FnAb buffer exchanged into and stored in PBS, pH 7.2.

Affinity-purified rabbit polyclonal FnAb and Flii peptide conjugated to keyhole limpet nemocyanin (Flii-KLH) were obtained from Mimotopes (Clayton, Victoria, Australia). Mouse monoclonal anti-KLH antibody was obtained from Abcam. Polyclonal goat anti-mouse HRP was obtained from Deka Murine IgG non-specific antibody (I8765) was obtained from Sigma (St Louis, Mo.).

pSi MP Preparation

Microparticles were fabricated from p-type Si wafers (boron-doped, resistivity <0.001 Ωcm, <100>) supplied by Virginia Semiconductors (Fredericksburg, Va., USA). The wafer was anodized in an 18 cm$^2$ etching cell in 3:1 HF:ethanol (v/v) solution with a current density of 222 mA/cm$^2$ for 4 min, and then electropolished for 30 s at 500 mA/cm$^2$. Then, 20 min of sonication was performed (S30H Elmasonic, 280W, Elma) to fracture the pSi membrane into MPs. The pSi MP suspension was filtered, washed with ethanol and dichloromethane before drying to completeness.

pSi NP Preparation pSi NPs were fabricated from p-type Si wafers (boron-doped, resistivity 0.0008-0.0012 Ωcm, <100>) supplied by Siltronix (France). The wafer was anodized in an 18 cm$^2$ etching cell in 3:1 HF:ethanol (v/v) solution with a square wave form comprising an initial current density of 50 mA/cm$^2$ for 7.3 seconds and second current density of 400 mA/cm$^2$ for 0.4 seconds. This two-step cycle was repeated continuously for 1 hour, generating a pSi film with alternating low and high porosity layers. The etched layer was removed from the Si substrate via electropolishing in 1.20 HF:EtOH at 4 mA/cm$^2$ for 4 minutes and 10 seconds. Subsequently the pSi membrane was sonicated for 16 hours in DMSO to generate chemically oxidized pSi nanoparticles. These nanoparticles were sized by passing through a 0.22 micron PTFE syringe filter, followed by the collection of the pellet after centrifugation at 22,000×g. This filtration and centrifugation allowed for the removal of large and small nanoparticles and facilitated the harvest of reasonably uniformly sized NPs that permanently remained in solution.

Dynamic Light Scattering

The mean particle size and size distribution of NPs were determined by dynamic light scattering (DLS; Zetasizer Nano ZS, Malvern Instruments, Malvern, UK). The analysis was carried out at a temperature of 25° C. using NPs dispersed in undenatured 100% ethanol. Every sample measurement was repeated 15 times.

Bandage Loading with FnAb-pSi NPs

The silver free polyester layer from Acticoat® bandages (Smith and Nephew, UK) was cut to approximately 1×1 cm$^2$ for loading of En-Ab pSi NPs. A solution of pSi NPs at a known concentration with a known preloaded amount of FnAb was used for the immersion of the bandage pieces. Pieces of bandage were immersed into the NP dispersion and immediately withdrawn and placed into a clean Eppendorf tube to dry. This step was repeated multiple times to ensure that the pSi were evenly distributed through the bandage. The dimensions and mass increase of the dried bandage was found on an analytical balance with 0.01 mg accuracy and used to calculate the loading of FnAb per cm$^2$ of bandage.

Electron Microscopy

Scanning Electron Microscopy (SEM)

SEM was performed on a FEI Quanta 450 FEG environmental SEM fitted with an SSD detector, and operated at 30 keV with a spot size of 2 mm. To help facilitate the dissipation of charge build-up, samples were coated with 5 nm thick layer of Pt prior to analysis. pSi MPs were dispersed directly onto conductive aluminium stubs for analysis, and were not coated for analysis.

Transmission Electron Microscopy (TEM)

The transmission electron microscopy (JEOL JEM-2100F-HR) equipped with a field emission gun was operated at 200 kV. The bright field images were recorded by CCD camera (GATAN Orius SC1000).

Infrared Spectroscopy

Attenuated total reflectance infrared (ATR-IR) spectra were obtained using a Bruker Hyperion 1000 IR microscope operating with a Bruker Vertex 80 IR spectrometer. The IR microscope was equipped with a liquid nitrogen cooled MCI detector. ATR spectra were collected over 64 scans, with a resolution of 4 cm$^{-1}$, using a Ge ATR crystal. All spectra were background corrected with an unetched silicon wafer of the same type. Spectra of the pSi layers were recorded and analysed using OPUS version 7.0 software, in the range of 650-4000 cm$^{-1}$. All IR spectra are presented with absorbance normalised to the Si—O peak at approximately 1100 cm$^{-1}$.

Fluorescence Microscopy

Fluorescence microscopy was performed on an Eclipse 50i microscope equipped with a D-FL universal epi-fluorescence attachment and a 100 W mercury lamp (Nikon Instruments, Japan). Fluorescence images were captured with a CCD camera (Nikon Instruments, Japan), using the following fluorescent filters. Blue channel (violet excitation, blue emission): excitation: 385-400 nm (bandpass, 393 CWL), dichromatic mirror: 435-470 nm (bandpass) and barrier filter wavelength: 450-465 nm (bandpass, 458 CWL). Green channel (blue excitation, green emission): excitation; 475-490 nm (bandpass, 483 CWL), dichromatic mirror: 500-540 nm (bandpass) and barrier filter wavelength: 505-535 nm (bandpass, 520 CWL). Red channel (green excitation, orange/red emission); excitation: 545-565 nm (bandpass, 555 CWL), dichromatic mirror: 570-645 nm (bandpass) and barrier filter wavelength: 580-620 nm (bandpass, 600 CWL). Images were analysed using NIS-elements v3.07 software (Nikon Instruments, Japan).

FnAb Loading and Release

General Experiments

FnAb was aliquoted at 1 mg/mL in PBS and stored at −80° C. when not in use. The loading of FnAb (1 mg/mL, pH 7.4) into the oxidised pSi NPs (denoted FnAb-pSi NPs) was carried out using a sealed low protein binding Eppendorf tube. After loading the NPs were spun to the bottom of the tubes (30 min at 22,000×g) and rinsed with PBS (pH 7.4, 15 min) to remove the weakly adsorbed antibody. The amount of protein loaded was determined from UV-Vis measurements (NanoDrop 2000 Spectrometer, Thermo Scientific) of the supernatant before and after incubation with the pSi NPs. The average loading of all pSi NP preparation used during this study was 268±35 μg of FnAb per mg of pSi. For each experiment with antibody-loaded pSi NPs, the loading regime is mentioned specifically below.

Release Experiments

FnAb (1 mg/mL) was labeled with fluorescein isothiocyanate (FITC) for 4 h in a sodium carbonate buffer (100 mM, pH 9.5). After labelling, the labeled protein was recovered using a Vivaspin 2 10,000 MWCO spin tube (Sartorius Stedim) according to the manufacturers instructions. This FITC labeled protein was then added to unlabeled FnAb at a known ratio and this stock was used to load pSi MPs as outlined above. Release was then monitored at 25° C. on an Agilent Technologies Cary Eclipse fluorimeter fitted with a Peltier temperature control system with a PMT of 650 V and excitation and emission slit widths of 5 nm. The emission was monitored at 525 nm and the excitation was performed at 490 nm. Data was recorded in an automated kinetic mode every 8 h for 7 d. The FITC signal was calibrated against a calibration curve constructed from dilutions of the FITC labeled FnAb stock solution.

Flii Sandwich ELISA (pSi-Bound FnAb Detection)

A sandwich enzyme-linked immunosorbent assay (ELISA) was performed to detect functional FnAb bound to either pSi particles or the well surface of a 96-well plate (assay control; Greiner). Here, pSi MPs were used instead of pSi NPs as excess unbound antibody is simply removed (i.e. pSi MPs can be centrifuged into a pellet), thereby reducing assay interference. Also, rabbit polyclonal FnAb was used instead of mouse monoclonal FnAb to prevent species cross-reactivity with the mouse α-KLH antibody. Both FnAb antibodies were raised to the same peptide sequence and displayed similar binding kinetics by ELISA.

To capture FnAb to the 96-well plate well, FnAb, diluted to 10 µg/mL in 0.1M NaHCO$_3$, was added at 50 µL/well and incubated for 12 h at 4° C. Wells were washed five times with 200 µL/well of 0.02 M Tris/HCl, 0.25 M NaCl buffer, pH 7, using a microtitration plate washer (ADIL Instruments). To quench non-specific binding, wells were blocked by the addition of 200 µL 1% (w/v) BSA in 0.02M Tris/HCl, 0.25M NaCl buffer, pH 7, for 4 h at 20° C. Wells were aspirated and incubated with 100 µL/well block buffer containing 10 µg/mL Flii-KLH, for 2 h at 4° C. Wells were washed five times then incubated with 100 µL/well block buffer containing 10 µg/mL mouse α-KLH antibody, for 12 h at 4° C. Another round of washed were performed before incubation with α-mouse HRP diluted 1/500 in block buffer for 1 h at 20° C. Unbound antibody was again removed by washing. OPD substrate (100 µL) was added to each well and incubated at 20° C. for 20 min to allow color development. The optical density of each well was measured at 450 nm on an automated ELISA plate reader (Sunrise™, Tecan Group Ltd., Australia).

The sandwich ELISA protocol involving FnAb being bound to pSi particles was similar to when FnAb was bound to the 96-well plate. The major difference was the addition of 1 mg FnAb-pSi MP per well to each 96-well plate well prior to the addition of FnAb (35 µg FnAb per mg pSi). Also, pSi was removed for the wash steps and then added back to unused wells for the following steps of the ELISA. Briefly, pSi MPs particles were decanted, centrifuged at 8,000 g for 5 min at 4° C., the supernatant was discarded, and the pSi pellet resuspended in 200 µL wash buffer. The OPD color change step involved the buffer being removed from the well, centrifugation at 8,000×g for 5 min to pellet the pSi particles, and finally the supernatant decanted back into unused wells for substrate detection on the plate reader.

FnAb Detection ELISA (Release from FnAb-pSi NPs)

A direct ELISA to detect FnAb was performed as previously described. [31] Briefly, a 100-µL aliquot of Flii peptide at a concentration of 10 µg/mL, in 0.1 M NaHCO$_3$, pH 8.5, was added to each well of a polyvinylchloride plate and incubated overnight at 4° C. Unbound peptide was aspirated from each well and the wells were washed three times with 0.02 M Tris/HCl, 0.25 M NaCl buffer, pH 7, using a microtitration plate washer (ADIL Instruments). Any remaining reactive sites in the wells were blocked by the addition of 200 µl of (w/v) BSA in 0.02 M Tris/HCl, 0.25 M NaCl buffer, pH 7, for 4 h at 20° C. Supernatant samples were centrifuged at 10,000 g for 30 min at 4° C. to remove pSi NPs, serially diluted in 1% (w/v) BSA in 0.02 M Tris/HCl, 0.25 M NaCl buffer, pH 7, and 50 µL was added to each ELISA well overnight at 4° C. Purified FnAb was also serially diluted, ranging from 12.5-50 µg/mL as a calibration curve. Unbound antibody was then aspirated and the plates were washed three times using a microtitration plate washer. Wells were then incubated with 100 µL of peroxidase-conjugated goat anti-mouse immunoglobulin at a 1/600 dilution in 0.02 M Tris/HCl, 0.25 M NaCl, pH 7, for 1 h at 20° C. Any unbound antibody was removed and the plate washed three times using a microtitration plate washer. OPD substrate (100 µL) was added to each well and incubated at 20° C. for 20 min to allow color development. The optical density of each well was measured at 450 nm on an automated ELISA plate reader (Sunrise™, Tecan Group Ltd., Australia). The concentration of FnAb in each sample was determined by interpolation through the calibration curve.

Protein Assays

Protein and antibody was quantified by NanoDrop (Thermo Scientific, Wilmington, USA) as per the manufacturer's instructions.

In Vitro Wound Healing Assay

The electrical properties of confluent and wounded keratinocytes was examined using Electric Cell-sensing impedance Sensing (ECIS) as previously described (Wegener J et al., 2000, Experimental Cell Research, 259: 158-166) applying the scratch wound assay function (Applied Biophysics, Troy, N.Y., USA) (Heijink I H et al., 2010, Eur. Respir. J., 35: 894-903. Briefly, primary keratinocytes were seeded into an 8W2X1E ECIS Cultureware Array (Applied Biophysics, Troy, N.Y., USA) and cultured until confluence, as determined by a plateau in the impedance signal at 24,000 Hz. FnAb-pSi NPs (290 µg FnAb per mg pSi) were diluted in fresh culture medium, sonicated for 5 min, then added to the culture wells, with each well receiving an equivalent of 20 µg FnAb. The cell impedance signal was tracked for 10 min before the array sensors were wounded at 2,500 µA, 48,000 Hz for 30 s, with effective wounding observed as a drop in impedance signal. The recovery of the wounded area was determined in real time by impedance, with recovery defined as the time taken for the signal to plateau.

Cell Proliferation Assay

Cell proliferation assays were performed using the metabolic substrate WST-1 according to the manufacturer's protocols (Roche Applied Science, Munich, Germany). FnAb-pSi NPs (290 µg FnAb per mg pSi) were diluted in fresh culture medium, sonicated for 5 min, then added to the culture wells, with each well receiving en equivalent of 20 µg FnAb.

Animal Studies

All experiments were approved by the Adelaide Children Youth and Women's Health Service Animal Care and Ethics Committee following the Australian Code of Practice for the Care and Use of Animals for Scientific Purposes (AE 973/03/17 and AE 991/12/17). Six mice were included per treatment group, with only female mice included in the study.

Murine Surgical Techniques

Mice were anaesthetised with inhaled isofluorane, and the dorsum shaved and cleaned with 10% (w/v) povidine iodine solution, incisional wounds were performed on the non-diabetic wild-type Balb/c mice (acute wounds), whilst STZ-induced diabetic mice received excisional wounds (diabetic wounds). In the non-diabetic mice, two equidistant 1 cm full-thickness incisions were made through the skin and panniculus carnosus using fine scissors on the flanks of the animals extending 3.5-4.5 cm from the base of the skull, 1 cm on either side of the spinal column. In the diabetic mice, equidistant 6 mm full-thickness excisions were made using punch biopsy. Incisional and excisional wounds were left to heal by secondary intention (i.e. the wound edges were not closed by sutures). Digital photographs were taken of the wounds daily. A ruler was aligned next to the wound to allow direct wound area and wound gape measurements to be made. Wounds were harvested at either 7 (acute and diabetic wounds) or 14 d (diabetic wounds only) and were bisected. One half was fixed in 10% (v/v) buffered formalin and processed so that the midpoint of the wound was sectioned and compared between groups. The other half was micro-dissected to remove any contaminating normal, unwounded skin and snap-frozen in liquid nitrogen for protein extraction.

Diabetic Mouse Model

Diabetes was induced using multiple low-dose STZ (Johnson M S et al., 2008, Pain, 140: 35-47). STZ is toxic to the pancreatic β-islet cell, rendering the mouse unable to produce an adequate amount of insulin (Michaels J et al., 2007, Wound Rep. Reg., 15: 665-670). Briefly, female 10-14 weeks old Balb/c mice were administered one IP injection of STZ for five consecutive days (STZ: 50 mg/kg, Sigma) in citrate buffer, pH 4.5. Mice were fasted for four hours before STZ injection.

Non-fasting blood glucose levels (BGL) testing commenced 3 weeks post-STZ injection by tail vein sampling. To maintain body weight and prevent ketoacidosis after 4 weeks of the last STZ injection animals with BGL>15 mmol/L were administered subcutaneous injections of insulin (2 IU Protaphane/Mixtard insulin, Novo-Nordisk). Using this regimen, the mice were maintained for a further 6 weeks, then wounded. Mice maintaining a BGL>15 mmol/L for a minimum of 2 weeks were classified as diabetic, with all others excluded from the trial.

Delivery of FnAb-pSi NPs to Mice Wounds

At time of injury, each wound was injected intradermally at the wound margin, using a 21G gauge needle to deliver a total volume of 100 µL. Incisional wounds received 50 µL to each side, whilst excisional wounds received 25 µL in four equidistant locations around the wound margin. All samples were diluted in phosphate buffered saline (PBS), pH 7.2, with pSi NP samples sonicated for 5 min prior to injection. A total of 50 µg antibody was delivered to each wound, with the amount of administered pSi-NP dependent on the efficacy of antibody loading.

Histology Immunohistochemistry and Image Analysis

Histological sections (4 µm) were cut from paraffin-embedded fixed tissue, with sections stained with haema-toxylin and eosin as previously described (R D L, H M F. Histopathologic technic and practical histochemistry. 4th ed, New York: McGraw Hill Book Company; 1976).

Protease Treatment of FnAb-pSi NPs

Proteolytic environments such as those associated with chronic wounds have been reported to contain up to 100-fold more proteases than, for example, acute wounds. Two matrix metalioproteases in particular (MMP-2 and MMP-7) are elevated in chronic wounds and have been shown to degrade IgG antibodies. The use of FnAb and other therapeutic antibodies to treat chronic wounds may therefore provide limited clinical efficacy due to their potential degradation at the wound site. We hypothesised that pSi may provide a protective environment for antibodies, protecting them from rapid protease digestion. Here, FnAb-loaded pSi microparticles (MPs) were incubated with pepsin, a protease known to fragment IgG antibodies. An FnAb release experiment was then performed with the protease treated pSi, with released antibody then tested for degradation.

FnAb-pSi MPs and FnAb-pSi NPs were treated with pepsin, a protease that fragments IgG, to evaluate the protective properties of pSi. Using an orbital shaker (Ratek, Adelab Scientific), FnAb-pSi MPs (66.6 ug FnAb per mg of pSi) and FnAb-pSi NPs (283 µg FnAb per mg of pSi) were incubated with pepsin (0.8% w/v) in 10 mM HCl, pH 2.5, for 90 min at 37° C. As a negative control, an equivalent amount of FnAb-pSi MPs and FnAb-pSi NPs was incubated under the same conditions but in the absence of pepsin. Samples were centrifuged at 8,000 g in an ultracentrifuge (Heraeus Fresco 21, Thermo Scientific) for 5 mm to pellet the pSi MPs and pSi NPs, with the supernatant collected for analysis. To remove residual pepsin, pSi MPs and pSi NPs were resuspended in 500 µL phosphate buffer, pH 7, mixed well then re-spun. Following three rounds of washing, pSi MPs and pSi NPs were resuspended in phosphate buffer, pH 7, containing 200 µg/mL BSA and protease inhibitors. Samples were incubated for 2 weeks at 25° C., with the buffer replaced daily and supernatants retained for further analysis. To confirm pepsin effectively fragmented FnAb, 100 µg of free FnAb (i.e. not associated with pSi) was also incubated with and without pepsin in 10 mM HCl, pH 2.5, for 90 min at 37° C. Although the release experiments in this study were performed at 25° C. (similar to wound environments), all pepsin digestions were performed at 37° C. to allow maximal antibody fragmentation.

SDS PAGE Gel Electrophoresis

Non-denatured sodium dodecyl sulphate-polyacrylamide gel electrophoresis (SOS-PAGE) was used to estimate antibody fragmentation (Gearing A J H et al., 2002, Immunology Letters, 81: 41-48) in response to pepsin treatment of FnAb-pSi NPs. Samples were prepared in SDS running buffer in the absence of 2-mercaptoethanol and there was no boil step performed. The gel, containing 10% (w/v) SDS, was run at 100 V for 60 min. The gel was excised and stained with Coomassie blue for 60 min, then de-stained for 2 h.

Statistical Analysis

Statistical differences were determined using the Student's t-test or an ANOVA. For data not following a normal distribution, the Mann-Whitney U-test was performed. A P value of less than 0.05 was considered significant.

Results

Figure 18A:
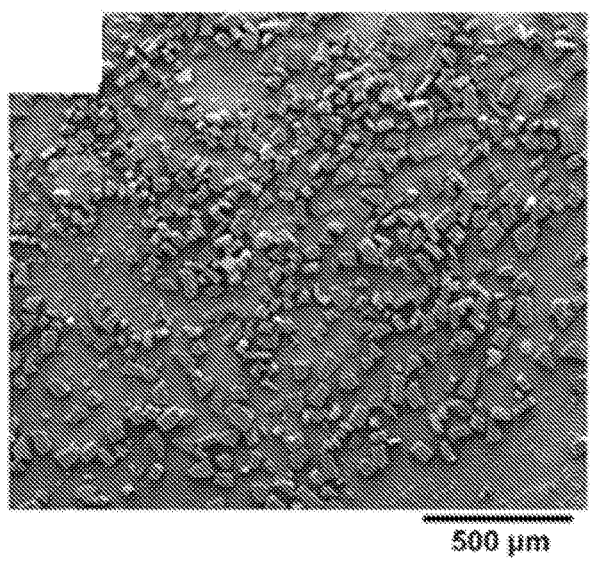
FIG. 18—shows in panel (A) Particle size distribution characterized by SEM and in panel (B) Pore structure and size of the pSi MPs.
Figure 18B:
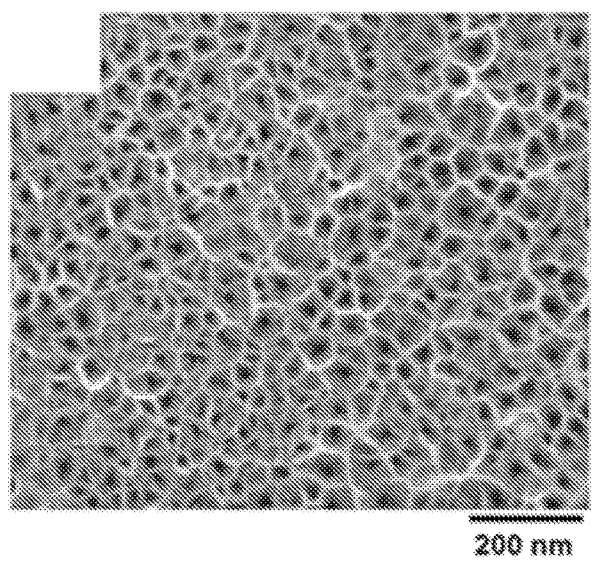
Figure 19:
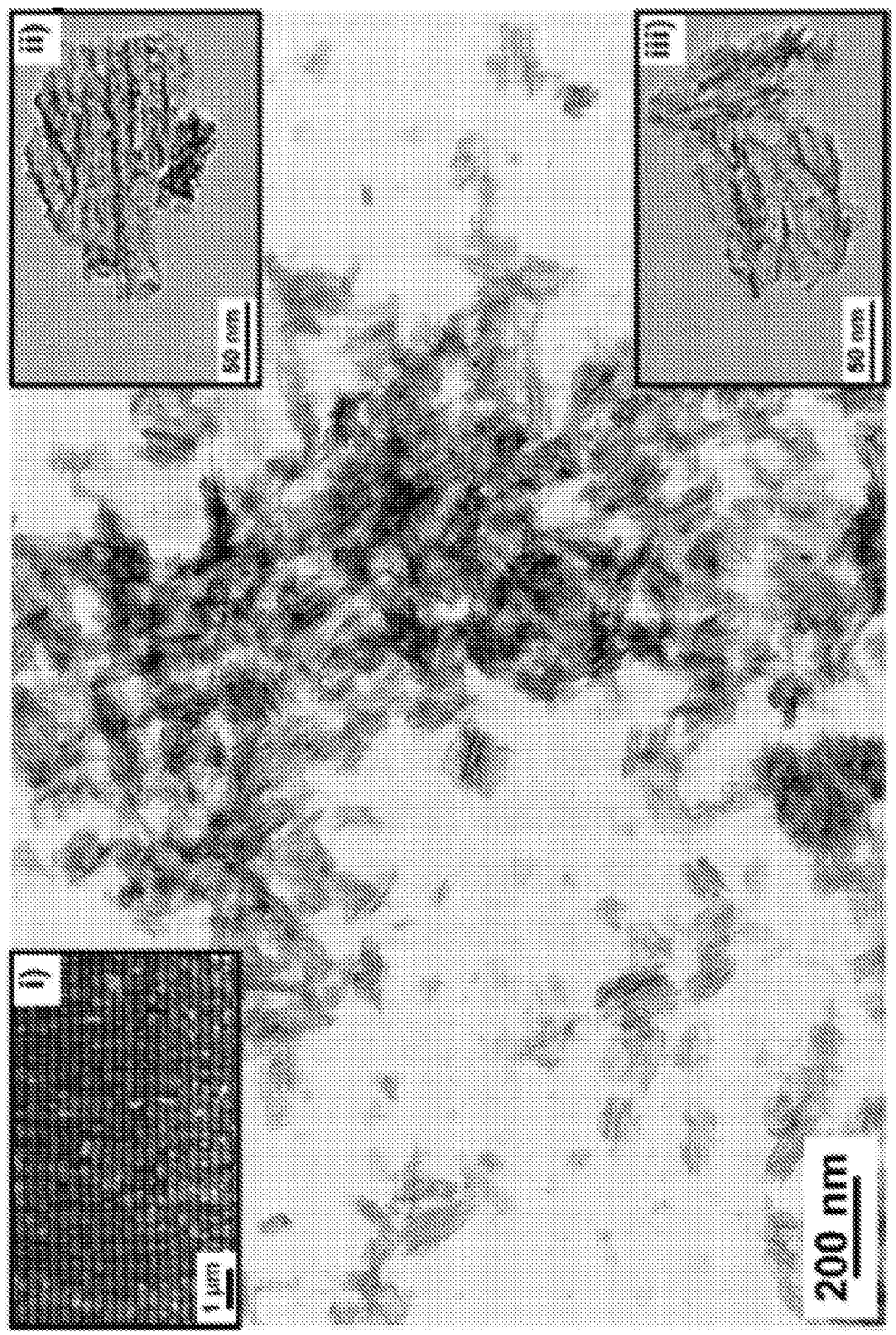
FIG. 19—shows a typical TEM micrograph of pSi NPs. Inset i shows the cross-section SEM image of the perforated membrane structure prior to sonication. Insets ii and iii show individual pSi NPs characterised by TEM.

Particle Fabrication and Characterization pSi microparticles (psi MPs) were fabricated by sonication of a pSi membrane obtained by electropolishing a pSi film from the Si substrate. The particles were characterized by SEM and were observed to have a pore size of 25.3±4.0 nm and particle size of 44.98±6.43 µm (FIG. 18). Particles are sized is the use of mesh sieves. All particles used are obtained from below a 53 micron sine and above a 25 micron sieve.

pSi nanoparticles (pSi NPs) were produced via anodisation of boron-doped Si $p^{++}$-type wafers in a mixture of aqueous hydrofluoric acid (HF) and ethanol in a Teflon cell with a platinum counter electrode. The perforated structure can be visualized by SEM (FIG. 19i). The approximate thickness of the perforated layer was 31.3 microns while the pSi NP layer and the perforation layer measured approximately 176 nm and 37 nm in thickness, respectively. After anodisation, the resulting pSi film was lifted off the Si wafer by electropolishing in dilute HF solution. The pSi film was fractured by ultra-sonication into pSi NPs, which were filtered through a 220 nm filter membrane. After filtration, the pSi NPs were centrifuged at 22000×g to remove small non-porous pSi NPs generated from the perforation layers. The resulting pellet of pSi NPs was re-dispersed in ethanol. TEM images (FIG. 19) of the obtained pSi NPs showed mesoporous nanoparticles with sizes in the range of 161±58 nm and a pore size of 33±7 nm. DLS gave a nanoparticle size of 149±25 nm in good agreement with the TEM based size measurements.

pSi NP Loading with FnAb

All FnAb loadings were performed with approximately 1 mg/mL solutions of FnAb at pH 7.4 in PBS. pSi MPs were able to load an average of 56.09±2.87 µg of FnAb per mg of pSi. pSi NPs were highly efficient at loading FnAb and were able to take an average loading of 268±35 µg of FnAb per mg of pSi. This is possibly due in part to the greater surface area of the pSi NPs. All loadings, for each individual batch of NPs used throughout this example were analysed by UV-Vis before use, allowing accurate loading results to be calculated for each sample and experiment.

IR Analysis

Figure 20:
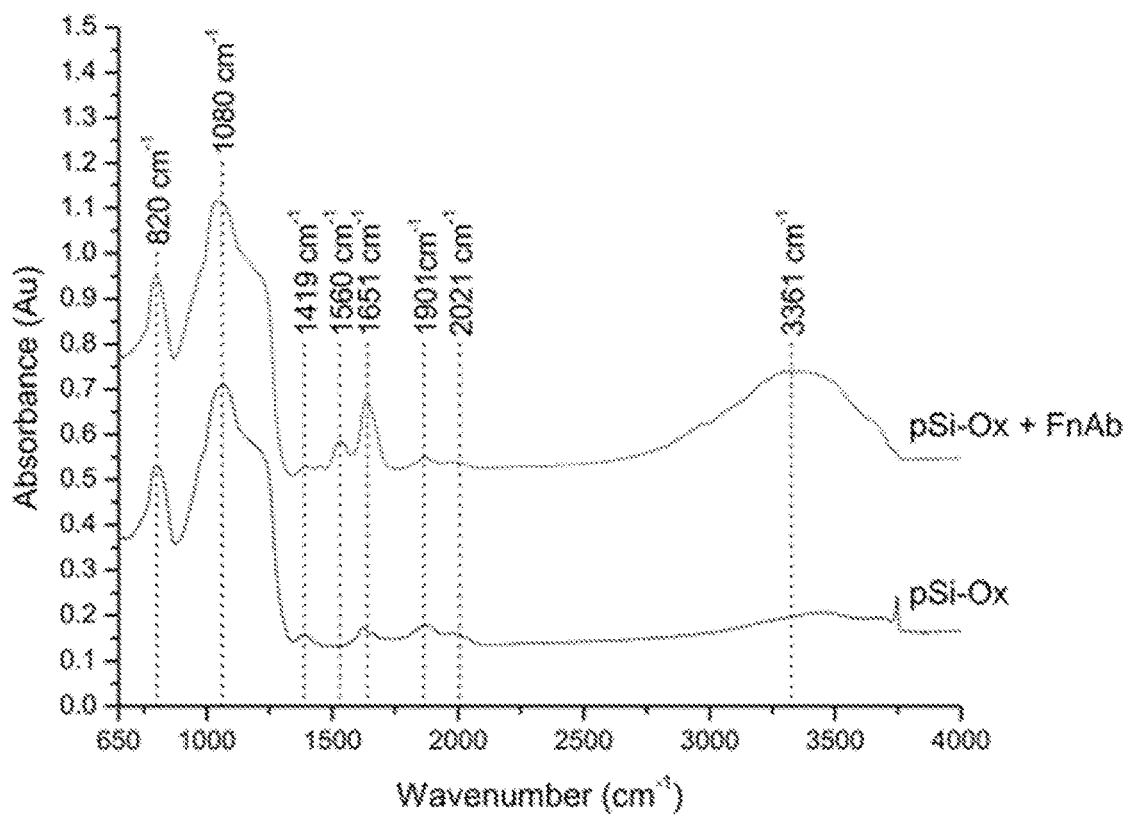
FIG. 20—shows IR spectra of oxidised pSi NPs and oxidised pSi loaded with FnAb.

To confirm the loading of pSi via IR, pSi NPs were deposited onto a 3-6 ohm cm Boron doped wafer, to allow for IR penetration, and analysed in transmission mode. The infrared spectra of ozone-oxidized pSi (FIG. 20, pSi—Ox) showed a strong and broad peak centred at 1080 $cm^{-1}$ due to asymmetric stretching vibrations of Si—O—Si surface bridging groups. It is important to note that the main Si—H, stretching region at 2100 $cm^{-1}$ has been completely removed via the oxidation process. The shoulder located at approximately 1150 $cm^{-1}$ can be attributed to the stretching of O—Si—O surface oxide species. After loading of FnAb into the oxidized pSi film (FIG. 20, pSi—Ox+FnAb), the spectra still showed strong characteristic peaks from the pSi—Ox surface in addition to new peaks at 1560 $cm^{-1}$ and 1651 $cm^{-1}$ for the amide I and II vibrations. Hence, FnAb was successfully loaded into the pSi substrate.

ICPMS Based Degradation

Figure 21:
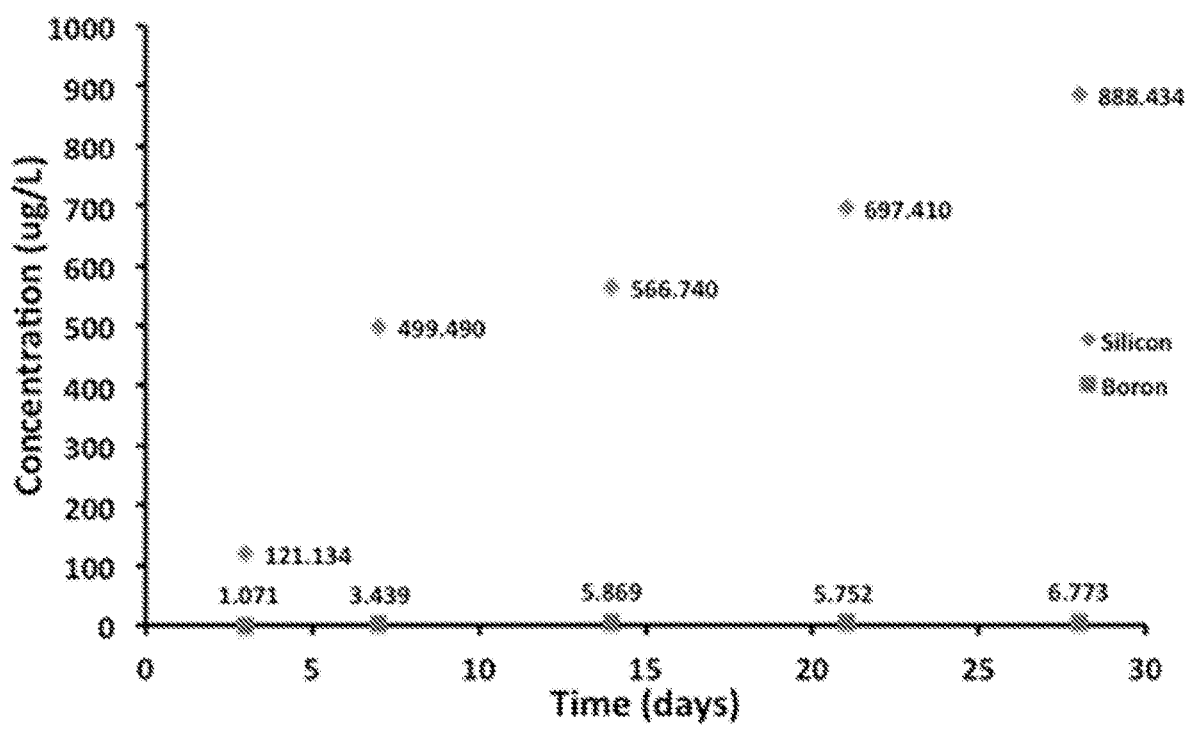
FIG. 21—shows ICPMS analysis of Si and B in the supernatant of Flightless I neutralizing antibody (FnAb) release experiments from pSi MPs over a 28 day period.

ICPMS analysis of Si and B concentrations in the supernatant above pSi based release experiments showed a steadily increasing concentration of Si over the 28 day period. This corresponds to less than 1% of the pSi MPs degrading over the 28 day time period (FIG. 21).

Loading and Release Kinetics

FITC labeled proteins were monitored for their release kinetics via fluorescence. pSi MPs, pSi NPs and Bandages were all monitored and all were found to have different release kinetics.

Figure 22:
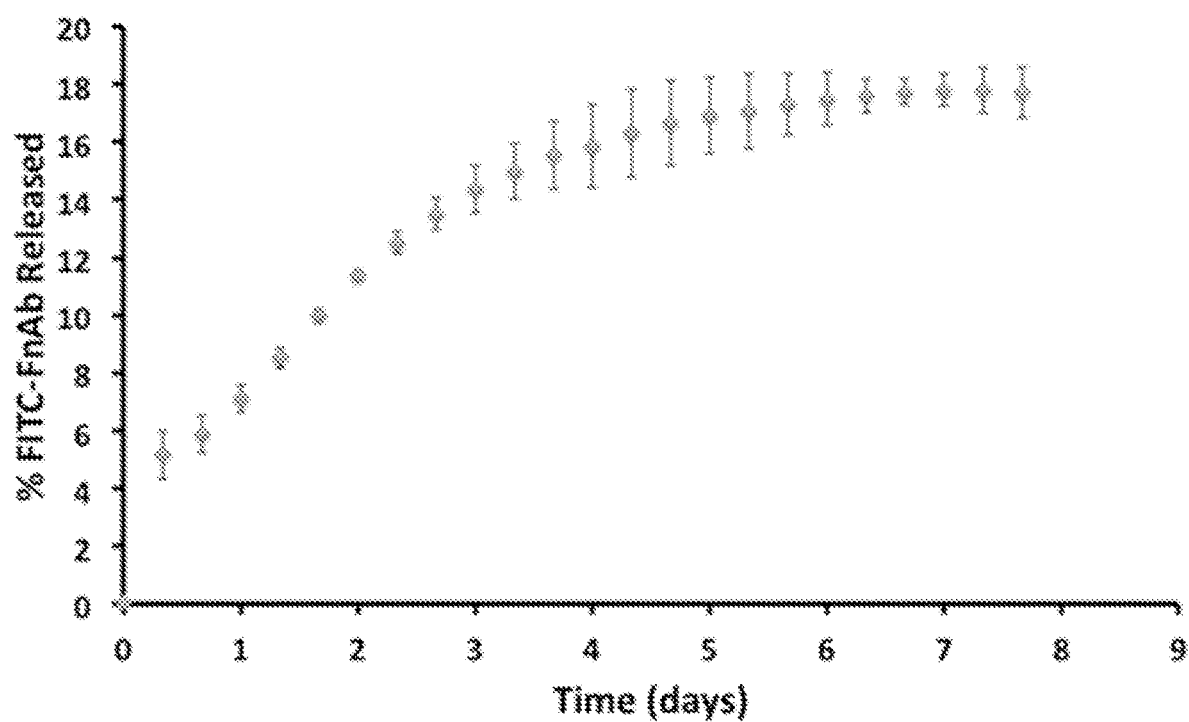
FIG. 22—shows release curves of FITC labeled Flightless I neutralizing antibody (FnAb) from pSi MPs. Release was performed at 37° C. in pH 7.4 PBS.

FIG. 22 shows the release of FITC-FnAb from pSi MPs over an 8 day period. The maximal release was approximately 18% over this 8 day period. The first 8 hours showed a significant burst release of approximately 5%. This was followed by sustained release for up to 3 days, before the release kinetics slowed. We would envision a bandage being changed within this 4 day time point.

Figure 23A:
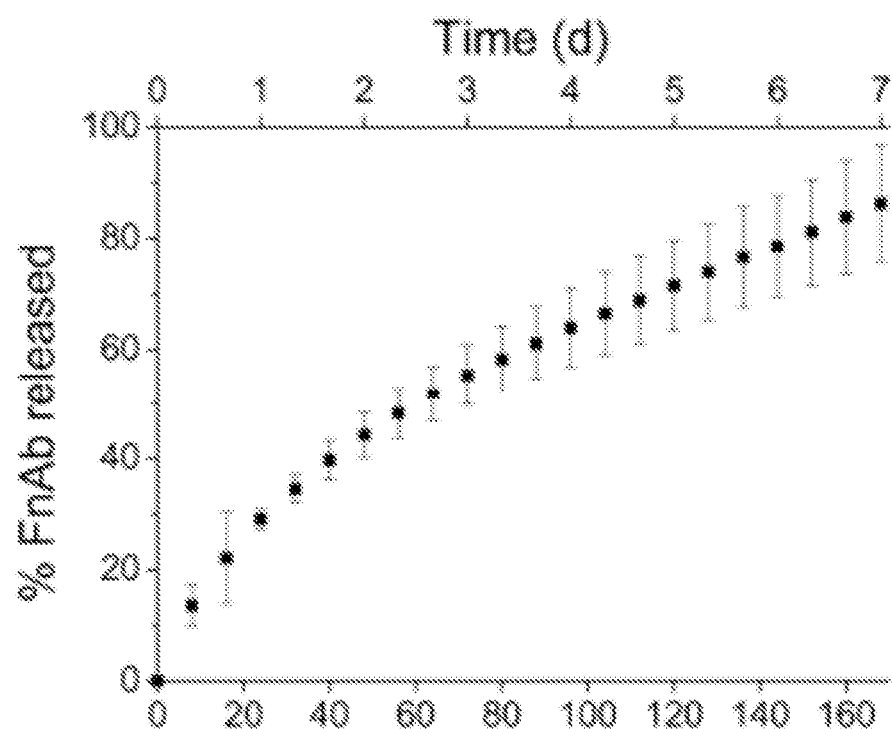
FIG. 23—(A) Release curves of FITC labeled FnAb from pSi NPs in PBS at 25° C. (B) fluorescence micrograph of pSi NPs loaded with FITC labeled FnAb (FITC-FnAb-pSi NPs) dispersed on a glass slide. (C) Sandwich ELISA to detect functional FnAb bound to pSi particles (FnAb-pSi). pSi was also loaded with non-specific IgG (IgG-pSi) or remained unloaded (unloaded pSi). Data presented as signal at 450 nm minus background. (D) Detection of total FnAb released from pSi NPs when incubated in PBS/BSA buffer for 2 weeks at 25° C. The column showing total loaded protein was determined by measuring total protein in the loading buffer before and after the initial load step. The column showing total released protein was evaluated by combining the protein estimates from each individual supernatant sample. (E) A direct ELISA was used to detect functional FnAb (■) in the supernatant samples (i.e. FnAb released from pSi NPs), with data presented as signal at 450 nm minus background. Supernatant was also collected from unloaded pSi NPs (●) and analysed by ELISA. Each supernatant sample contained a similar amount of FnAb. All data presented as mean+/− one standard deviation (n=3). *P<0.05. **P<0.005.
Figure 23B:
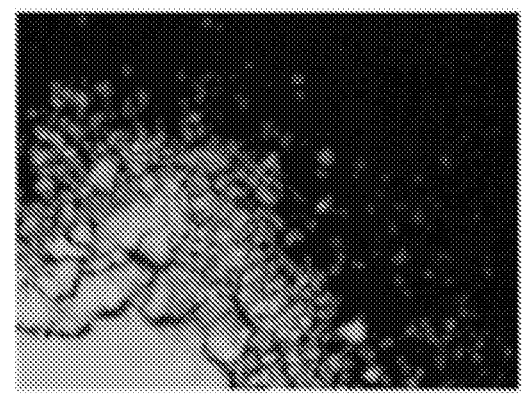
Figure 23C:
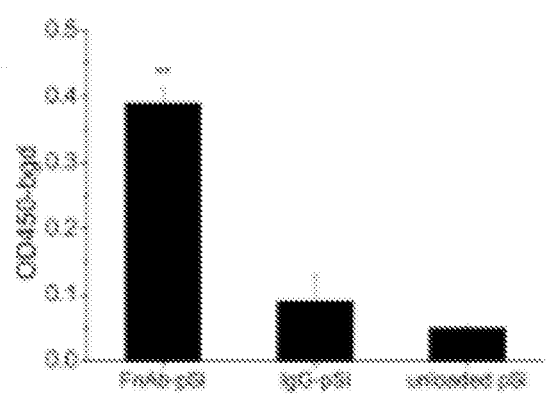

FIG. 23A shows the release of FITC labeled BSA from pSi NPs. FITC labeled proteins were monitored for their release kinetics from pSi NPs via fluorescence. Over the course of 7 d, approximately 86.3% of the antibody was released, the kinetics closely match the Higuchi model ($R^2$=0.998). The Higuchi model is an empirical model commonly used to describe the release kinetics of drugs from insoluble porous materials (Higuchi T J. Pharm Sci. 1951; 50:847), it is well established and commonly used for modeling drug release from matrix systems. The model is based on a square root of a time dependent process of Fickian diffusion. The Ritger-Peppas model also showed a very good fit ($R^2$=0.997) and the n values were above 0.5 (indicating that the FnAb was released according to non-Fickian (anomalous) diffusion) (McInnes S J P et al., 2012, ACS Appl. Mater. Interfaces, 4: 3566-3574). Loading was also qualitatively confirmed by fluorescence microscopy of dried FITC-FnAb loaded pSi NPs (FIG. 23B). An ELISA showed that FnAb, when bound to pSi, retained functionality of binding to the Flii-peptide (FIG. 23C) with minimal non-specific cross reactivity.

Activity Testing of Released FnAb

Figure 23D:
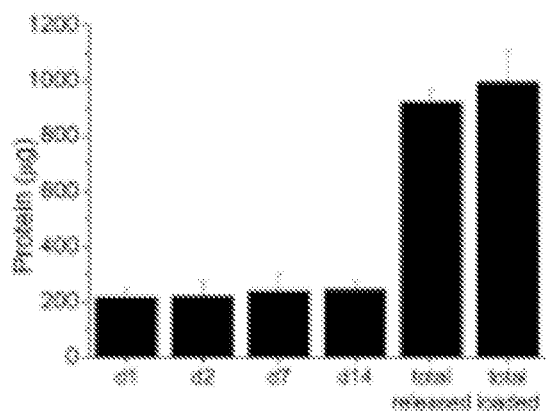
Figure 23E:
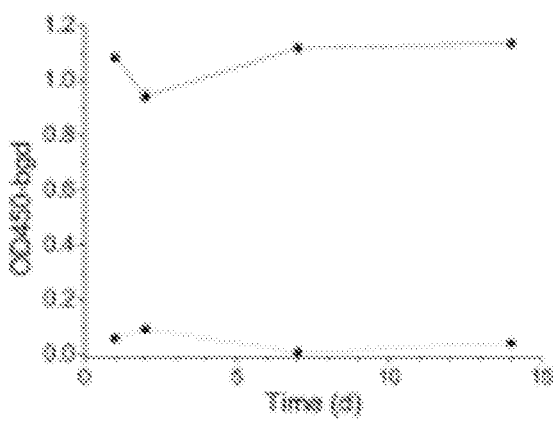

FnAb released from pSi NPs was collected at day 1, 2, 7 and 14, and tested by FnAb functional detection ELISA. FIG. 23D shows that equivalent amounts of FnAb was released at each time point, with 93% of total loaded FnAb released after 14 d. Released FnAb present in the supernatant at each time point was demonstrated to successfully bind to the Flii peptide (FIG. 23E), indicating FnAb retained its functionality for up to 14 d. There was negligible signal detected in the supernatant from unloaded pSi NPs.

Furthermore, the pSi degradation by-products were shown to not interfere with the ELISA assay (FIG. 24). In this regard, FnAb was treated with sodium metasilicate, a major breakdown product of pSi, to determine whether degrading pSi NPs impair antibody functionality. When measured by ELISA, all tested concentrations of sodium metasilicate, had no significant effect on the functional binding of FnAb compared to untreated controls (FIG. 24A). When FnAb was treated with PBS containing pSi MPs, incubated for 20 and 27 d respectively at 25° C. to produce pSi breakdown material, the ELISA detected no change in FnAb reactivity compared to the untreated control (FIG. 24B).

In Vitro Testing

Figure 25A:
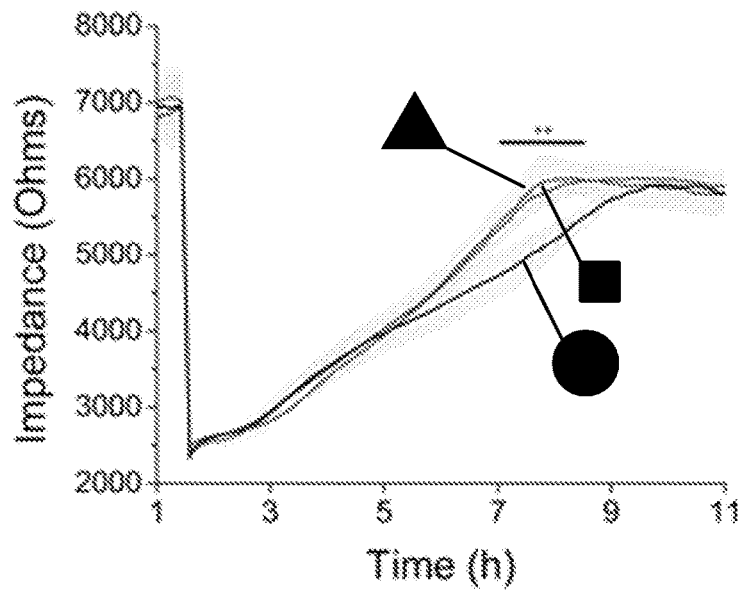
FIG. 25—shows the effect of FnAb-pSi NPs on wound healing and cell proliferation. ECIS wound healing assay (A, B). (A) Primary keratinocytes were grown to confluence in 8W2X1E arrays, treated with FnAb-pSi NPs (t=0), then electrically wounded at 2,500 μA and 48,000 Hz for 30 s (at t=1.5 h). Cells recovery was then monitored by impedance at 24,000 Hz for 10 h. Cells were treated with FnAb-pSi NPs (25 μg pSi NPs/well @292 μg FnAb/mg pSi NPs; ▲, 12.5 μg pSi NPs/well; ■) and unloaded pSi NPs (25 μg pSi NPs/well) (●). Three array sensors were wounded for each treatment group, with data presented as mean+/− one standard deviation. (B) Photographs of the array sensors showing unwounded cells, and wounded cells treated with FnAb- or unloaded pSi NPs. The wound margin is indicated by dotted lines, the scale bar is 125 microns, (C) WST-1 proliferation assay where primary keratinocytes were seeded at $5\times10^4$ cells/ml and incubated for 24 h, washed with PBS, then treated with FnAb-pSi NPs (black bars) or unloaded pSi NPs (grey bars) over a mass range of 1.06-17.12 μg of pSi/well (giving an FnAb concentration of 3.1, 6.3, 12.5, 25 and 50 μg/well). Data presented as mean+/− one standard deviation (n=6). *P<0.05. **P<0.005.
Figure 25B:
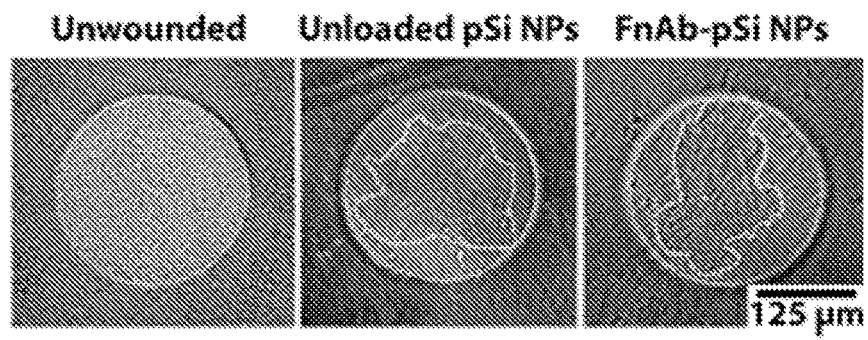
Figure 25C:
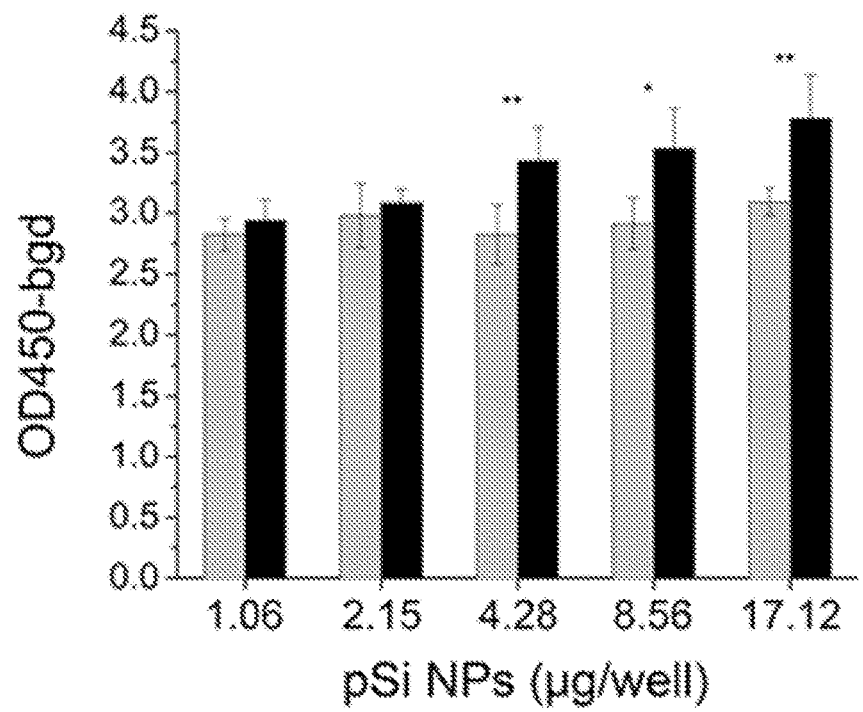

Keratinocytes and fibroblasts treated with FnAb in solution show improved scratch wound closure, cell migration and proliferation. To demonstrate FnAb released from pSi NPs retained its functionality, primary keratinocytes at confluence were electrically wounded (ECIS wound healing assay), treated with FnAb-pSi NPs, then recovery was determined by impedance measurements (FIGS. 25A, B). Cells treated with FnAb-pSi NPs showed a 25% increase in impedance recovery compared to cells treated with unloaded NPs ($P<0.005$ for >1 h in time). A WST-1 assay was performed to determine the effect of FnAb-pSi NPs on cellular proliferation (FIG. 25C). Sub-confluent keratinocytes incubated with FnAb-pSi NPs showed a significant increase in proliferation at 48 h compared to cells treated with unloaded NPs ($P<0.05$).

In Vivo Testing—7 Day Incisional Mouse Model Wound Trial

Figure 27A:
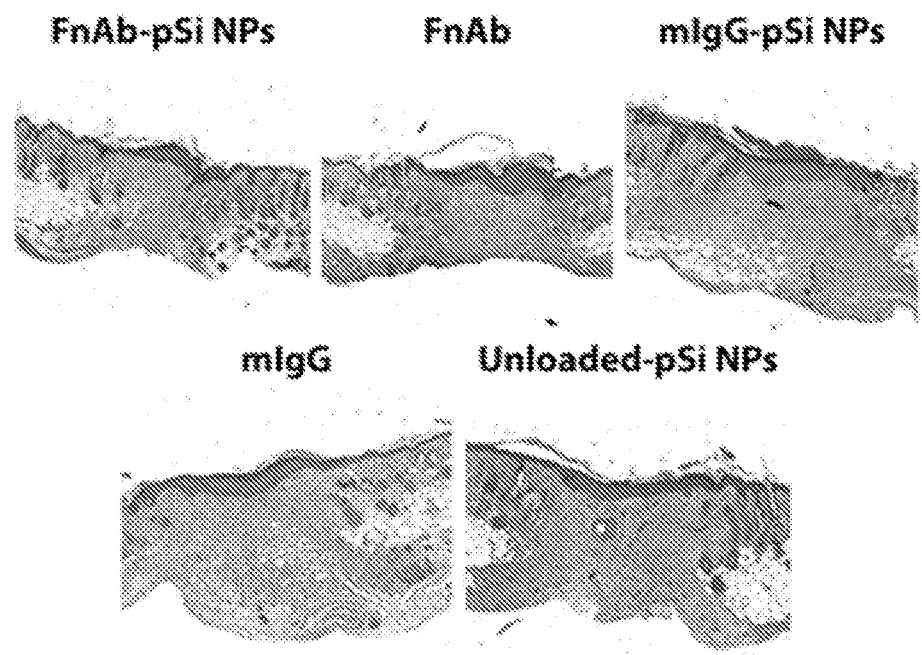
FIG. 27—shows microscopic analysis of incisional wound trial in healthy wild-type mice. Wounds were treated with a single intradermal injection of FnAb-pSi NPs. FnAb alone, mIgG-pSi NPs, mIgG alone or unloaded pSi NPs at the time of injury. Mice were humanely killed at day 7 post-surgery, with wound tissue sectioned, stained with haematoxylin and eosin (A) and wound gape measured (B). Each wound was treated with the equivalent of 50 μg of FnAb or mIgG. Each treatment group contained six mice, with two wounds per mouse. Images in (A) were representative of each treatment group. **P<0.005.
Figure 27B:
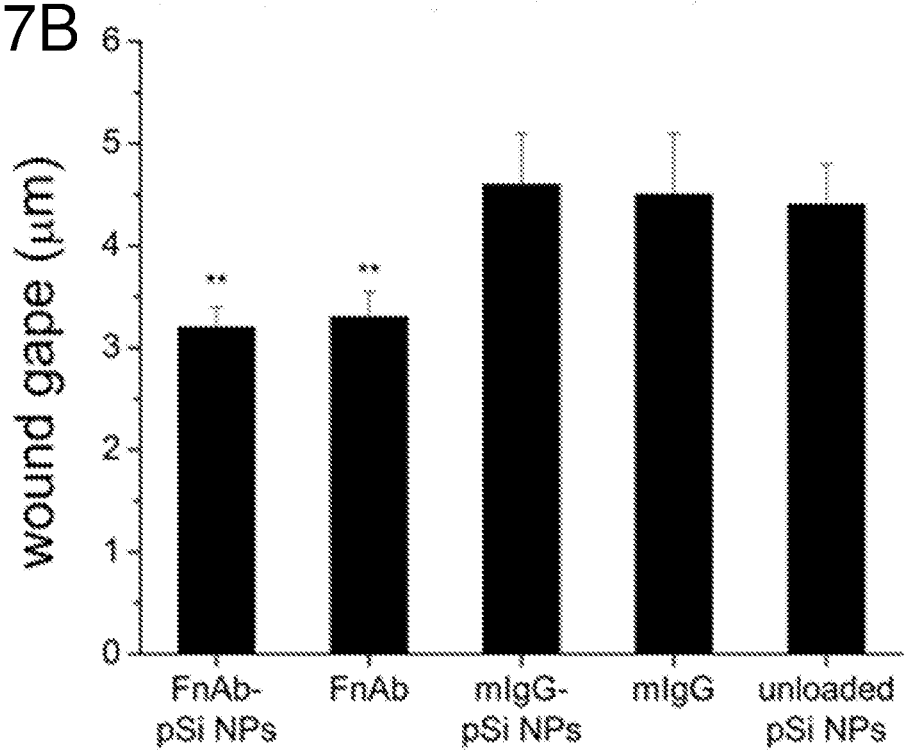

Acute incisional wounds in wild-type mice were treated with FnAb-pSi NPs and mIgG-pSi NPs, involving a single dose at the time of injury. The wound area for all mice increased in the first 24 h as a result of accumulated wound exudate transiently expanding the wound margin. Wounds treated with FnAb-pSi NPs had a significantly smaller wound area at day 6 and 7 than those treated with mIgG-pSi NPs (P<0.005, FIG. 26A). Whilst the wound gape for FnAb-pSi NP treated wounds was significantly smaller than for mIgG-pSi NPs or unloaded pSi NPs, the small improvement compared to free FnAb without pSi NPs was not statistically significant (FIG. 26B). In addition, no statistically significant difference was observed in wound gape between mice treated with mIgG-pSi NPs, mIgG alone and unloaded pSi NPs (FIGS. 26B, C). Microscopic analysis of tissue sections at day 7 by hematoxylin and eosin staining confirmed the macroscopic wound measurements (FIG. 27).

FnAb-pSi NPs Improve Wounding in Diabetic Mice

Figure 28A:
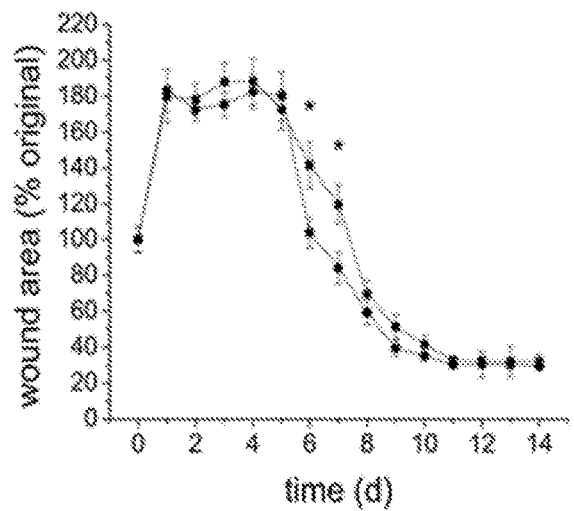
FIG. 28—shows macroscopic analysis of excisional wound trial in diabetic mice. Wounds were treated with intradermal injections of FnAb-pSi NPs (●) or mIgG-pSi NPs (■) at the time of injury (A). Each wound was treated with the equivalent of 50 μg of FnAb or mIgG. At day 7, wound gape was also determined in mice treated with FnAb alone, mIgG alone and unloaded pSi NPs (B, C). Wound area calculated as a % of original wound area. Each treatment group contained six mice, with two wounds per mouse. Images (C) were representative of each treatment group. *P<0.05. **P<0.005.
Figure 28B:
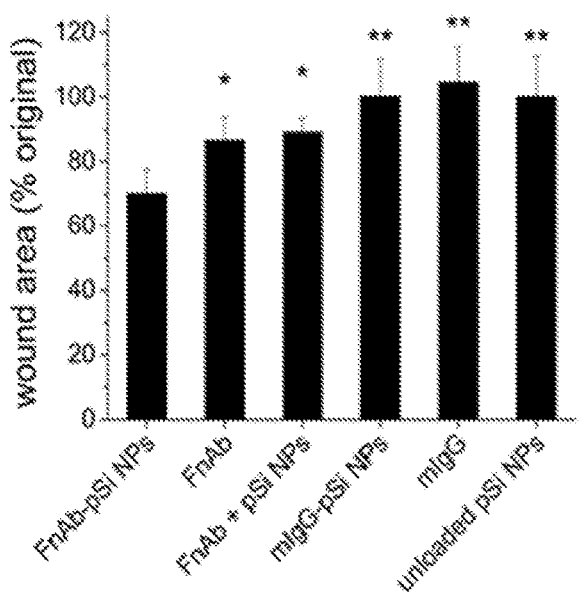
Figure 28C:
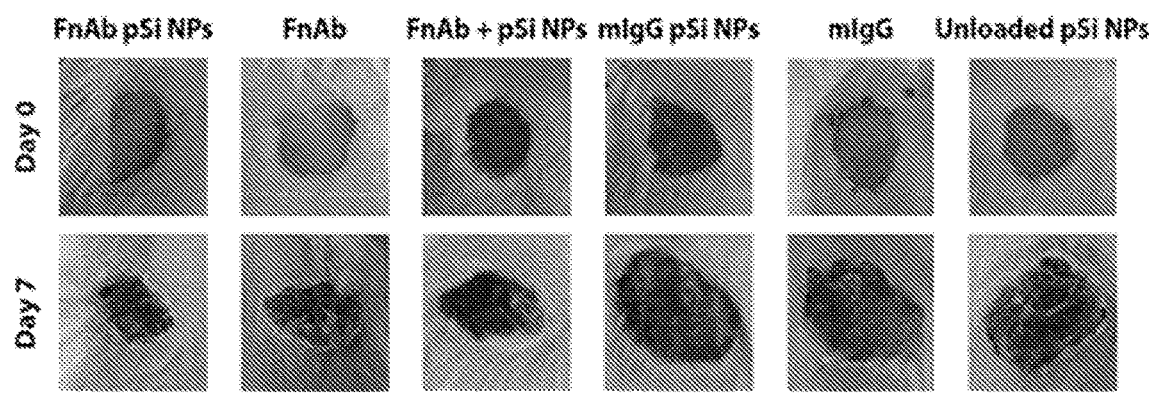
Figure 29A:
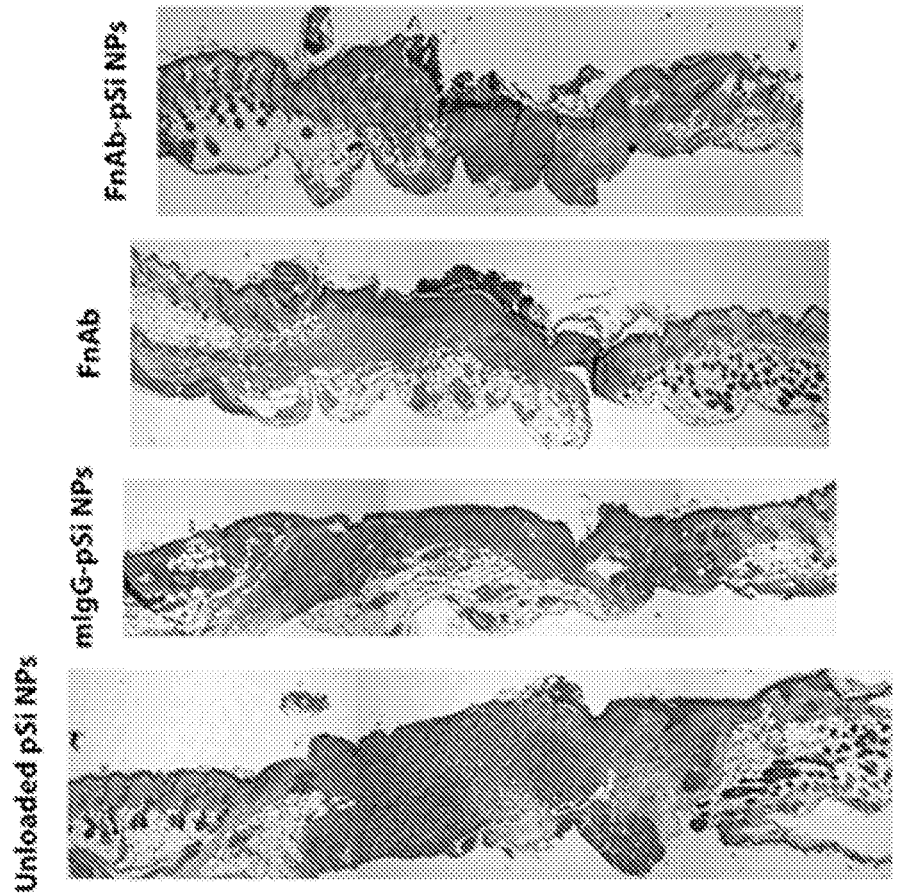
FIG. 29—shows microscopic analysis of excisional wound trial in diabetic mice. Wounds were treated with intradermal injections of FnAb-pSi NPs, FnAb alone, mIgG-pSi NPs or unloaded pSi NPs at the time of injury. Each wound was treated with the equivalent of 50 μg of FnAb or mIgG. Sections of day 7 wounds were stained with haematoxylin and eosin (A), with wound gape measured and presented as the % of mIgG-pSi NPs (B). Each treatment group contained six mice, with two wounds per mouse. Images in (A) were representative of each treatment group, *P<0.05. **P<0.005.
Figure 29B:
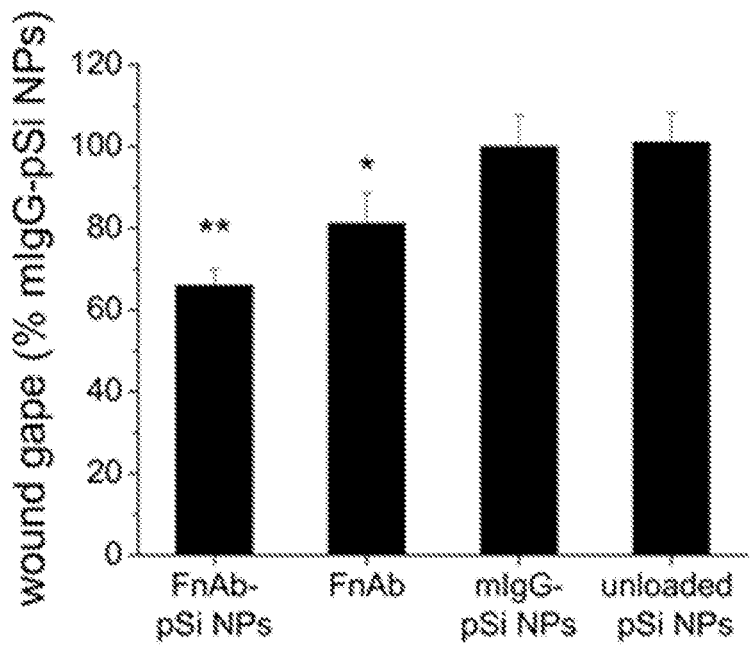

FnAb-pSi NPs were administered to excisional wounds in diabetic mice, involving a single intradermal dose at the time of injury (FIG. 28). The wound area in FnAb-pSi NP treated mice was significantly smaller than mIgG-pSi NP control treated wounds at days 6 and 7 (P<0.005), with wounds closing approximately 2 d earlier (equivalent to 18% faster) (FIG. 28A). FnAb-pSi NP treated mice showed significantly smaller wounds at day 7 than when FnAb was administered alone (P<0.05) (FIGS. 28B, C, FIG. 29). There was no difference in wound area between mice treated intradermally with mIgG-pSi NPs, free mIgG and unloaded pSi NPs. Interestingly, no difference in wound area was seen between treatment with FnAb alone without pSi NPs compared to FnAb and pSi NPs when added together (i.e. NPs were not loaded with antibody prior to administration).

pSi-Loaded FnAb is Protected from Proteases

Figure 30A:
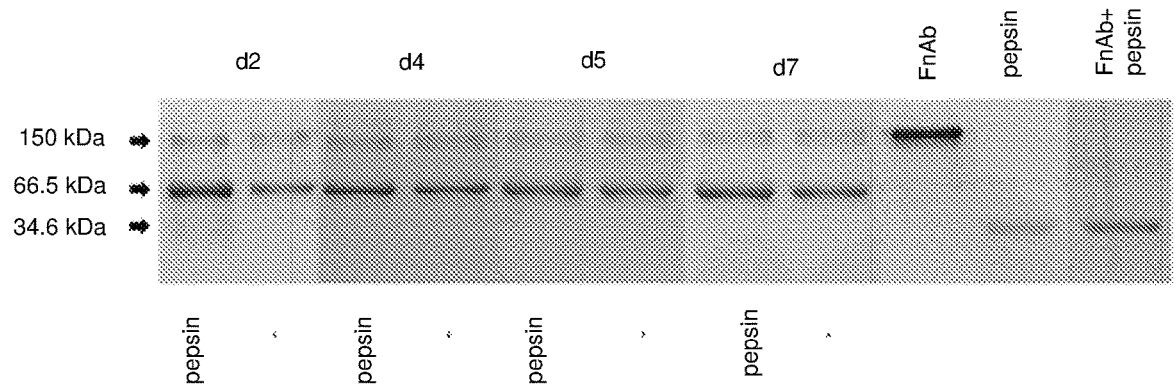
FIG. 30—shows the results of protease treatment of FnAb-pSi MPs (A) and FnAb-pSi NPs (B). FnAb-pSi MPs and FnAb-pSi NPs were transiently incubated with or without pepsin at 37° C., then incubated for 7 d at 25° C., with supernatants decanted daily for analysis of structural integrity. Samples were run on SDS-PAGE gels and then coomassie-stained. Structurally intact FnAb was identified as 150 kDa. Albumin, identified as a 66.5 kDa band, was added to the supernatant during the release experiment to assist with the stability of the released antibody. Pepsin was identified as the 34.6 kDa band on the gel. Free FnAb, incubated with and without pepsin, was also run on the gel, (as positive and negative controls) along with free pepsin.
Figure 30B:
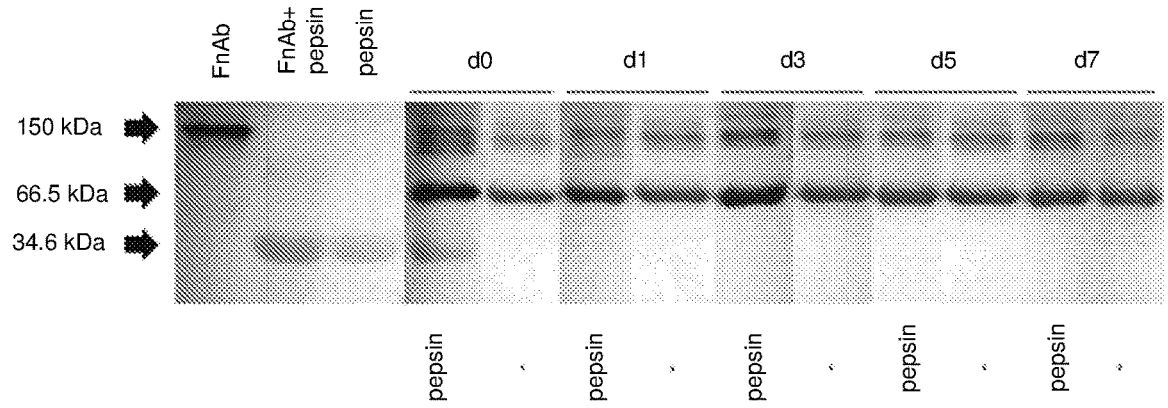

To determine if proteases are able to digest antibody loaded into the pores of the pSi MPs and the pSi NPs, FnAb-pSi MPs and FnAb-pSi NPs were transiently incubated with pepsin, a protease known to fragment IgG antibodies, pSi MPs and pSi NPs were rinsed to remove residual pepsin, then an antibody release experiment was performed over 7 d, with antibody containing supernatant decanted each day for analysis. Results for FnAb-pSi MPs are shown in FIG. 30A and results for FnAb-pSi NPs are shown in FIG. 30B. At each time point, FnAb released from pepsin-treated FnAb-pSi MPs and FnAb-pSi NPs was 150 kDa, indicating the antibody was structurally intact, the same as observed for FnAb-pSi NPs not treated with pepsin. With respect to FnAb-pSi NPs (FIG. 30B), a weak band corresponding to pepsin was observed in the day 0 sample, but not any of the latter time points, suggesting most pepsin was effectively removed prior to commencing the release experiment. Free FnAb incubated with pepsin, using the same digestion conditions the pSi MPs and pSi NPs were exposed to, led to the complete absence of 150 kDa bands on the gel, indicating digestion conditions were sufficient to completely digest unprotected FnAb.

The evidence shows that pSi MPs and pSi NPs can protect FnAb from the action of proteases. This suggests that pSi MPs and pSi NPs provide a useful vehicle to deliver therapeutic antibodies to chronic wounds.

Co-Loading and Pre-Loading with BSA

Figure 31:
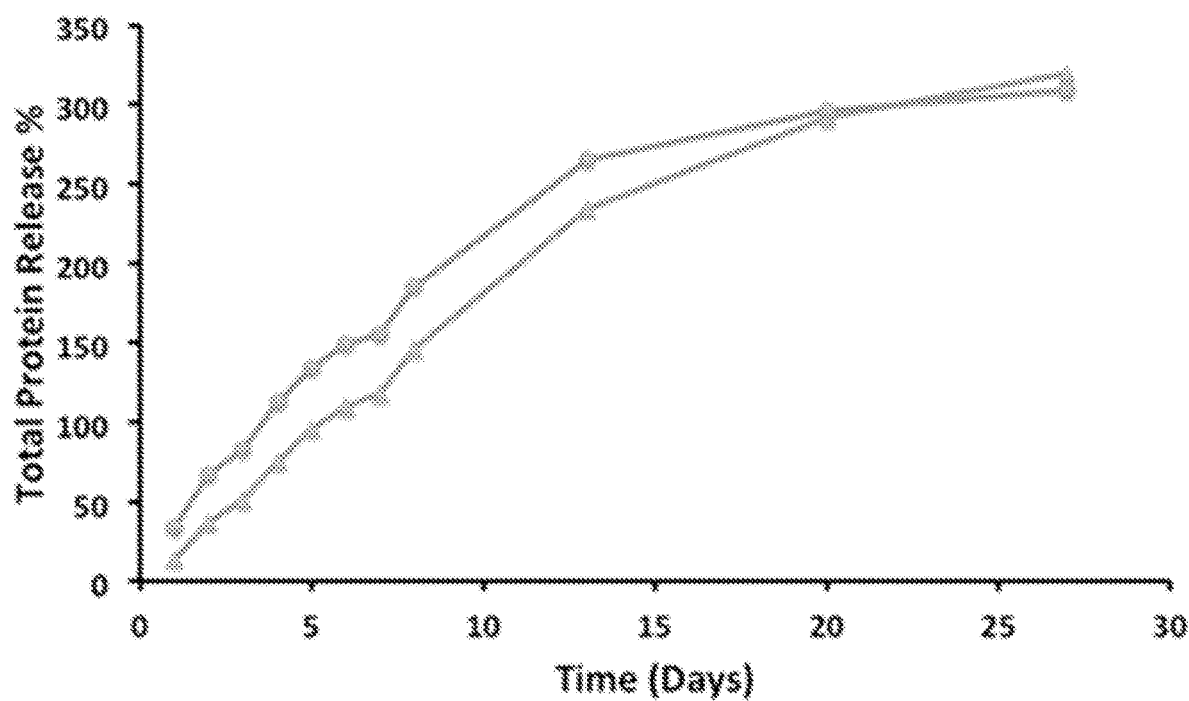
FIG. 31—shows release curve at 37° C. for the full 28 days as monitored via UV-Vis at 280 nm. The antibody was either co-loaded (▲) or pre-loaded (●) with bovine serum albumin (BSA) into the pSi before commencing the release experiment.
Figure 32:
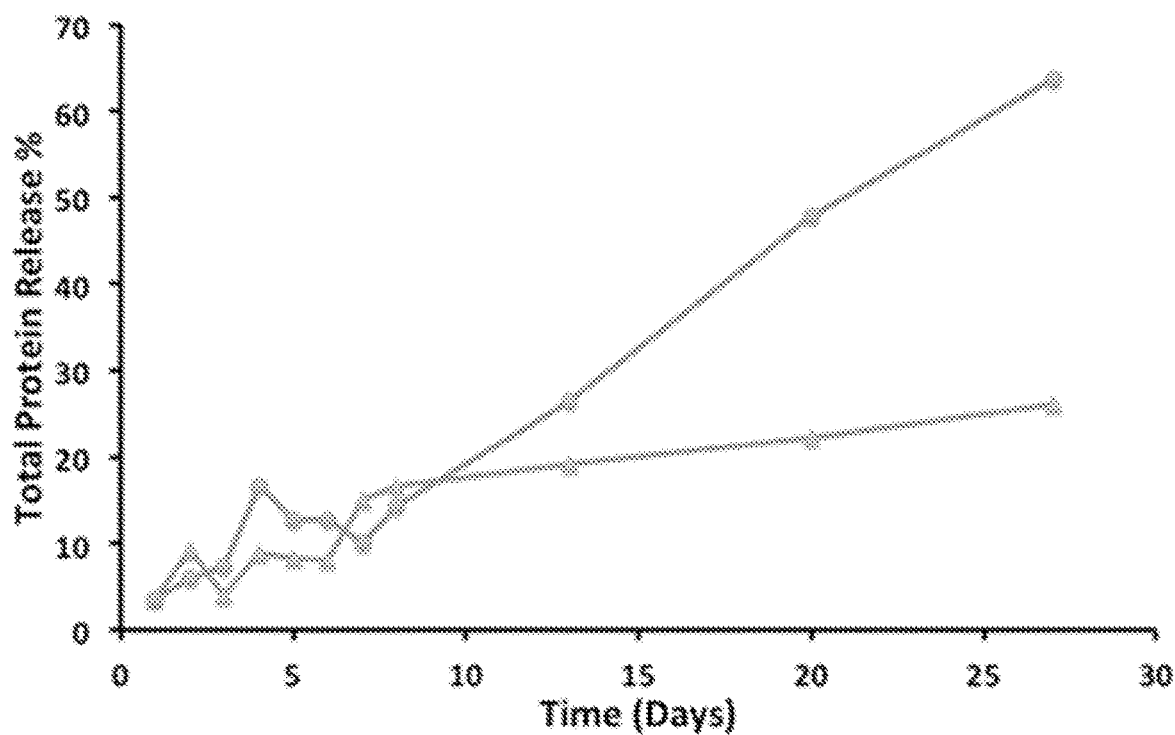
FIG. 32—shows release curve at 4° C. for the full 28 days as monitored via UV-Vis at 280 nm. The antibody was either co-loaded (▲) or pre-loaded (●) with bovine serum albumin (BSA) into the pSi before commencing the release experiment.

To help maintain the activity of the FnAb, 1 mg of BSA was either loaded prior to the FnAb or at the same time as the FnAb. Release was monitored via UV-Vis at 280 nm for 28 days. Both the co-loaded and preloaded samples had similar release kinetics. The release % above 100% could be caused by the production of silicic acid ($Si(OH)_4$), causing an elevation in the base line of the UV-Vis spectra (FIGS. 31 and 32). When the release was performed at 4° C. the release % remained under 100%, possibly due to a lower amount of silicic acid by-products from the pSi degradation.

Figure 33:
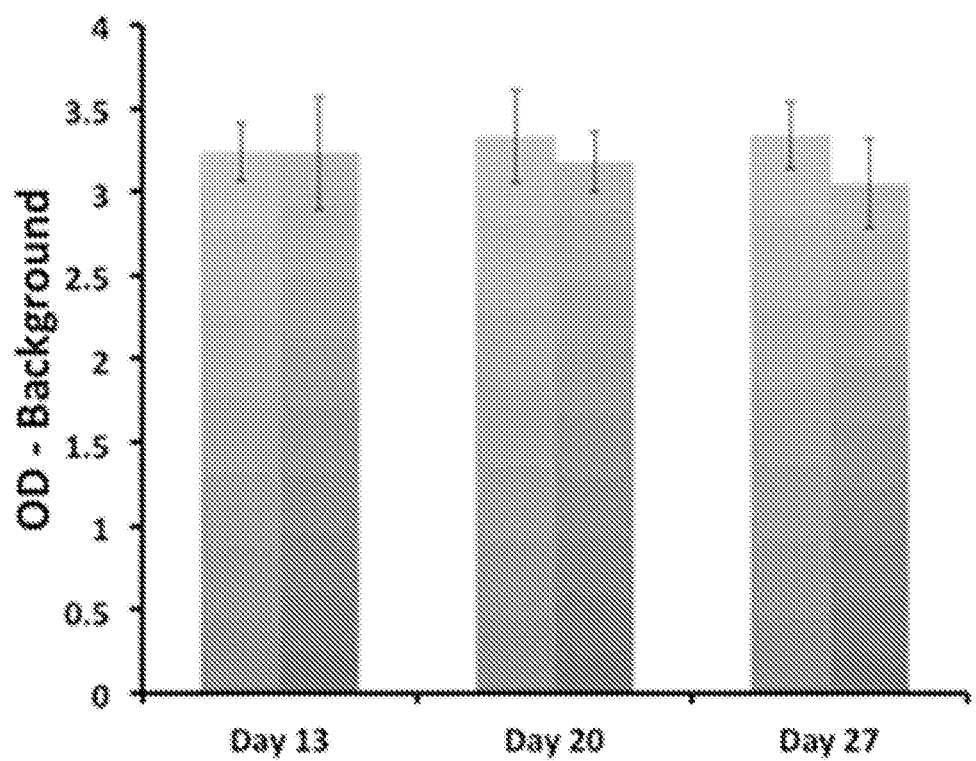
FIG. 33—shows WST-1 proliferation analysis for cultured fibroblasts treated with Flightless neutralizing antibody (FnAb) released from pSi MPs. Bovine serum albumin was pre-loaded into the pSi before FnAb loading. The release experiment was performed at 4° C. (left columns) and 37° C. (right columns). The pre-loaded samples were taken from the release runs in FIGS. 31 and 32.
Figure 34:
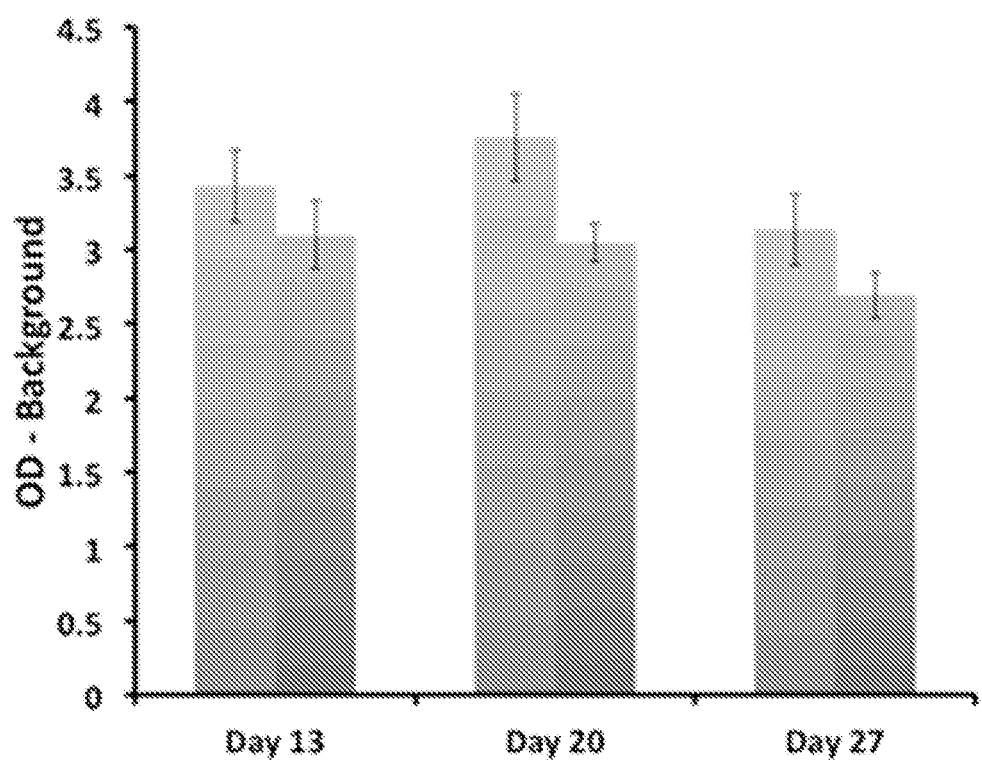
FIG. 34—shows WST-1 proliferation analysis for cultured fibroblasts treated with Flightless neutralizing antibody (FnAb) released from pSi MPs. Bovine serum albumin was co-loaded into the pSi with FnAb. The release experiment was performed at 4° C. (left columns) and 37° C. (right columns). The co-loaded samples taken from the release runs in FIGS. 31 and 32.
Figure 35A:
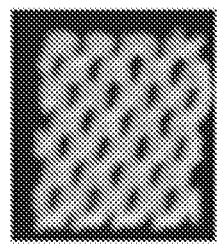
FIG. 35—shows characterisation of bandage materials. (A) Photography of unloaded bandage material. (B) Bandage material loaded with FnAb-pSi NPs after a single immersion. (C) Low resolution SEM micrograph of unloaded bandages and (D) high resolution SEM micrograph of unloaded bandages. (E) Low resolution SEM micrograph of FnAb pSi NP loaded bandages and (F) high resolution SEM micrograph of loaded bandages.
Figure 35B:
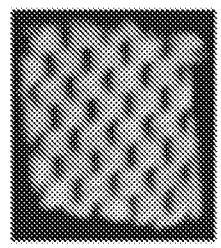
Figure 35C:
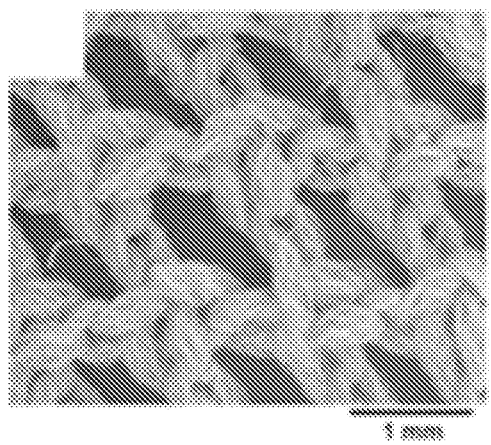
Figure 35D:
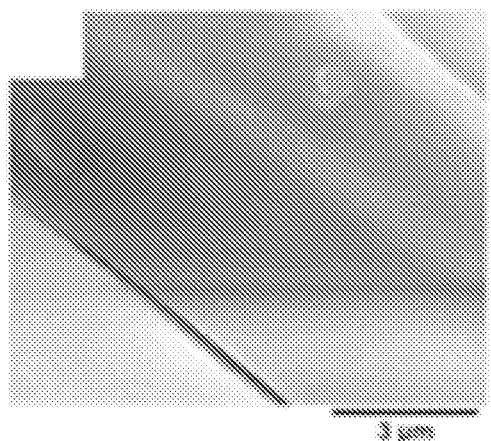
Figure 35E:
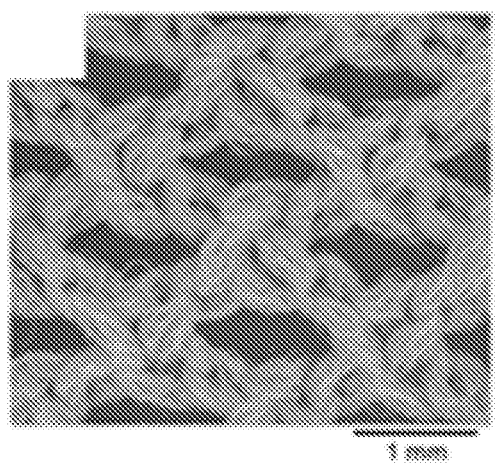
Figure 35F:
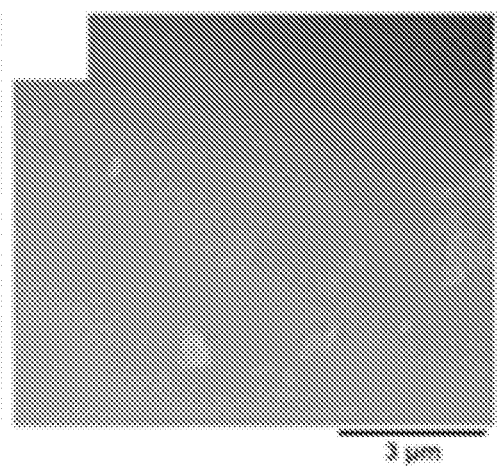

The release solutions were tested for their ability to affect cell proliferation via the WST-1 assay (FIGS. 33 and 34). The 4° C. samples in both cases show an increase in proliferation, possibly due to the lower incubation temperature also assisting with the retention of the stability of the FnAb. This data indicates that the loading of additional proteins such as BSA with the functional antibody may help preserve the activity of the antibody.

Bandage Fabrication and Characterization

The average mass of pSi NPs loaded into the bandages was calculated to be 0.44±0.22 mg of pSi per $cm^2$ of bandage, per immersion and the average FnAb loading of pSi NPs obtained was 268±35 μg of FnAb per mg of pSi. Given these values a single bandage loading via dipping contains approximately 0.118 mg of FnAb per $cm^2$ of bandage, whilst a bandage loaded by six consecutive immersions could potentially contain up to 0.71 mg of FnAb per $cm^2$ of bandage. FIG. 35 shows that the correct morphology of the bandages was maintained after the loading and that NP agglomerates could be visualised on the polyester fibers via SEM.

Figure 36:
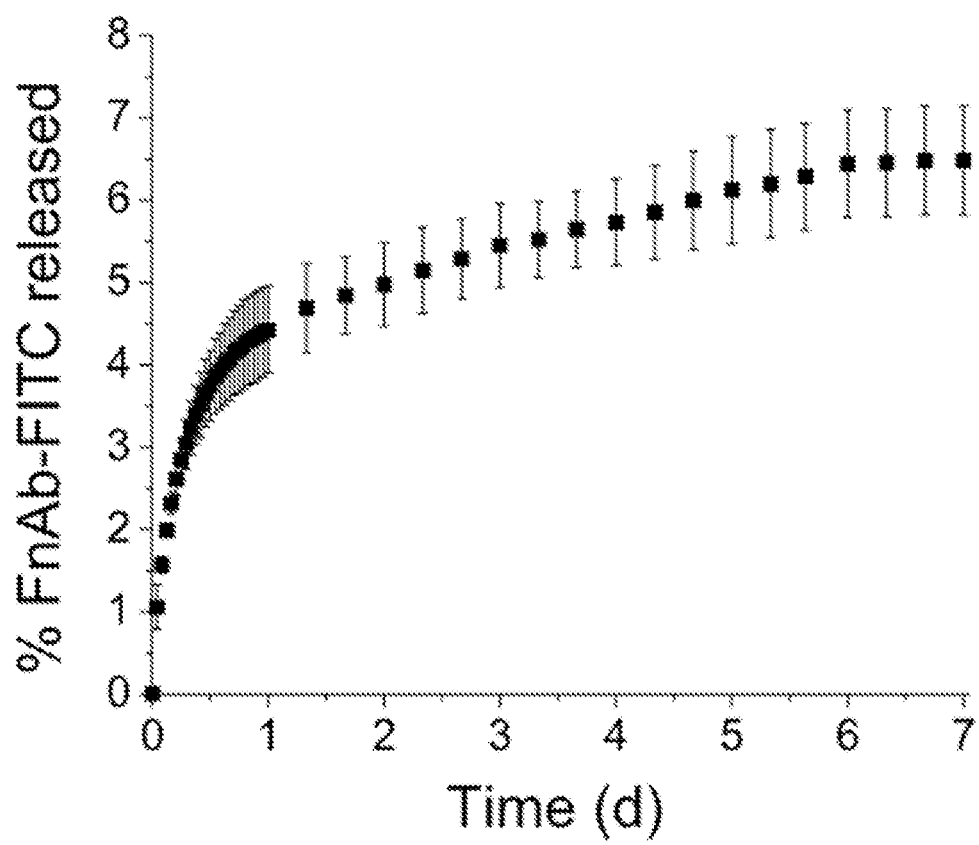
FIG. 36—shows release curves at 25° C. of FITC labeled Flightless I neutralizing antibodies (FnAbs) from pSi NPs loaded into polyester bandages.

FIG. 36 shows the release curve of FITC-FnAb from a pSi NP loaded bandage. The release kinetics show a very small burst release of only 1% and then a maintained release over the day of analysis. This release is slower than that of the pSi NP's alone, possibly indicating that the presence of the polyester bandage slows the release kinetics.

Discussion

In this study, pSi NPs were evaluated as a drug delivery vehicle for chronic wounds, in part due to their ease of fabrication, but also because they can be easily injected or further processed into bandages or gels for topical applications. Importantly, pSi NPs can also be loaded with large payloads of therapeutic antibodies, on average 268 μg per mg pSi NPs and up to 303 μg per mg pSi NPs. This corresponds to an approximately 4-fold higher loading than observed for pSi MPs in the study of Example 1 possibly due to more efficient packing of the antibody.

pSi NPs degrade under physiological conditions, releasing the antibody so it is available to neutralise its target antigen. Here, FnAb-pSi NPs incubated at 25° C., a similar temperature to the to the diabetic ulcer environment, were found to release 86.3% of total loaded FnAb after 7 d, which is expected to be a suitable window for improved wound healing. This was higher than observed in pSi MPs loaded with Infliximab, where approximately 50% of total loaded antibody was released over an equivalent time frame, despite NPs being loaded with more antibody. Using NPs will therefore allow less pSi to be administered to patients where required in particular clinical settings than when using MPs.

As pSi degrades, silicic acid is the major breakdown product produced. Previous studies have found that pSi is biocompatible, biodegradable and bioresorbable in animals and pSi has now been used in human trials. In the current study, the breakdown products of pSi, sodium metasilicate, had no detrimental effect on FnAb functionality. This agrees with the study in Example 1 where the functionality of the therapeutic antibody Infliximab was not affected by release from and degradation of pSi MPs.

The nature of antibody-pSi binding is electrostatic and it is important to carefully control the strength of this binding as damage can be caused to the protein structure, resulting in loss of activity. To demonstrate that loaded antibody retained its functionality, a modified sandwich ELISA was performed, showing FnAb bound to pSi retained its ability to bind to the target antigen. Next, the FnAb detection ELISA was used to test samples of supernatant decanted from FnAb-pSi NPs after incubation at 25° C. FnAb was found to be effectively released from pSi NPs into the supernatant and was able to bind to the Flii antigen target.

Scratch wounding assays and proliferation assays in cultured cells have previously shown increased wound closure and proliferation in response to FnAb treatment. Here, these assays found FnAb retained its functionality, and was released at sufficient levels to have a physiological effect on cultured cells, indicating that loading densities of the particles were sufficiently high to be useful in vitro.

FnAb treatment of cultured cells has previously shown in numerous studies to increase wound closure and proliferation as measured by scratch wounding and proliferation assays. These assays were utilised in the current study to evaluate whether the FnAb released from pSi NPs was structurally intact and without conformational change. Here, FnAb released from pSi NPs was shown to retain its functionality, and moreover was released at sufficient levels to have a physiological effect on cultured cells, indicating that loading densities of the particles were sufficiently high to be useful in vitro.

In the current study, acute wounds treated with a single dose of FnAb-pSi NP at the time of wounding showed a significant reduction in wound area compared to untreated controls. Notably, the reduction in wound gape at day 7 was similar to those wounds treated with tree FnAb in the absence of pSi NPs, providing important evidence that functional FnAb was successfully released from pSi NPs and into the wound environment. The improvement in wound healing indicated that the pSi NP pores were not blocked by wound fluid, which was a possible limitation of using pSi. No difference in wound gape at day 7 between mIgG-pSi NP, mIgG alone and unloaded pSi NP treated wounds was observed, indicating that pSi NPs alone have no effect on wound closure.

The repeated administration of low-dose STZ to healthy wild-type mice induces diabetes, leading to delayed wound closure and elevated protease concentration in wounds. One study showed these mice having elevated matrix metalloproteinase (MMP)-9 protein levels in excisional wounds compared to those in healthy non-diabetic controls at both day 3 and at wound closure, indicating a protease rich wound environment. STZ treated mice therefore provided a valuable in vivo model to evaluate whether pSi NPs improved the delivery of FnAb to protease rich wound environments. Here, treatment with free FnAb accelerated wound closure compared to free mIgG treated controls, suggesting the diabetic wound environment did not completely degrade the administered antibody. Importantly, delivering a single dose of FnAb-pSi NPs showed a further statistically significant improvement in wound closure rate compared to administering an equivalent dose of free FnAb alone. Using psi NPs as a delivery vehicle therefore improves wound healing in STZ-treated wounds. No difference in wound area was seen between treatment with FnAb alone compared to FnAb and pSi NPs when added together (i.e. NPs were not loaded with antibody prior to administration), suggesting FnAb must be loaded into the pores to enhance wound closure. We next tested the hypothesis if the enhancement was due to protection of the FnAb from proteases in the chronic wound environment.

A number of proteases are elevated in chronic wounds, including MMPs, with one study showing 30-fold higher MMP activity in chronic than acute wounds. MMP-3 and MMP-7 are reported to degrade IgG antibodies, therefore likely contributing to impaired efficacy of therapeutic antibodies in diabetic wounds. Experiments were therefore performed to determine whether pSi could actually protect the therapeutic antibody from proteases, providing a mechanism to explain the improved efficacy in diabetic wounds compared to when FnAb was administered alone. Here, FnAb-pSi NPs were incubated with pepsin under conditions that completely degrade FnAb alone. The subsequent release experiment snowed that FnAb released from these particles had retained its structural integrity, thereby confirming that the pSi provides a protective environment from proteases.

In this work, we delivered pSi NPs loaded with FnAb by intradermal injection at the wound margin. Although intradermal injection is not a practical mode of administration for the clinic it was performed in the current study as it is a more effective method of delivering the drug to the wound margin, thereby reducing variability. In the present study we also translated the delivery method into a bandage platform with a view to bringing significant improvements to the ability of diabetic wounds to heal.

Conclusion

We demonstrate that pSi NPs have a high loading capacity for FnAb and can extend antibody release for 7 d in vitro. The released FnAb was active and detectable by ELISA. The released FnAb was also active as determined by in vitro assays in keratinocytes, and when injected in vivo the loaded pSi NPs were able to improve the wound healing of both incisional acute wounds and excisional diabetic wounds. Importantly, the pSi NPs were able to impart protection to the FnAb stored within the pores from proteolytic environments as demonstrated by protease experiments. It is envisaged that pSi NPs can be incorporated into wound dressings materials and deliver FnAb to wound fluid in order to improve chronic wound healing.

EXAMPLE 3

Treatment of Uveitis

For the treatment of uveitis, antibody (for example Infliximab) loadings may be performed with approximately 1 mg/mL solutions of antibody at pH 7.4 in PBS. pSi MPs may be loaded to an average of about 50 to about 70 µg of antibody per mg of pSi whilst pSi NPs may be loaded to about 500 to about 800 µg of antibody per mg of pSi. The porous silicon particles (about 0.1 mg to about 10 mg) may be injected into the conjunctiva to treat the uveitis and the clinical characteristics followed to assess treatment. A suitable dose and treatment regime may be selected by a medical practioner.

EXAMPLE 4

Treatment of Crohn's Disease or Ulcerative Colitis

Infliximab loaded porous silicon particles may be formulated into an oral composition for ingestion for a subject suffering from Crohn's disease or ulcerative colitis. Ingestion of the oral composition may then occur, the particles passing through the proteolytic environment of the stomach, where the antibody is protected by loading onto the porous silicon, and into the remainder of the gastrointestinal tract. Release of the antibody from the particles in the gastrointestinal tract may then be used to treat the diseases/conditions and the clinical characteristics followed to assess treatment. A suitable dose and treatment regime may be selected by a medical practioner.

As used herein, the singular forms "a," "an," and "the" may refer to plural articles unless specifically stated otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

All methods described herein can be performed in any suitable order unless indicated otherwise herein or clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

The description provided herein is in relation to several embodiments which may share common characteristics and features. It is to be understood that one or more features of one embodiment may be combinable with one or more features of the other embodiments. In addition, a single feature or combination of features of the embodiments may constitute additional embodiments.

The subject headings used herein are included only for the ease of reference of the reader and should not be used to limit the subject matter found throughout the disclosure or the claims. The subject headings should not be used in construing the scope of the claims or the claim limitations.

Although the present disclosure has been described with reference to particular examples, it will be appreciated by those skilled in the art that the disclosure may be embodied in many other forms.

The invention claimed is:

1. A method of treating a wound, the method comprising:
    administering a composition to the wound, wherein the composition comprises: a porous silicon substrate, wherein the porous silicon substrate has been thermally oxidized at a temperature less than 600° C.; and a therapeutically effective amount of a wound healing antibody passively bound to pores of the substrate, or passively bound to the surface of the substrate and to pores of the substrate, and
    releasing the wound healing antibody from the substrate so as to treat the wound.

2. The method of claim 1, wherein the porous silicon substrate comprises nanoporous silicon, or mesoporous silicon, or nanoporous silicon and mesoporous silicon.

3. The method of claim 1, wherein the porous silicon substrate comprises a porosified silicon film produced from a crystalline silicon wafer by more than one etching step.

4. The method of claim 1, wherein the porous silicon substrate comprises mesoporous nanoparticles, or mesoporous microparticles, or mesoporous nanoparticles and mesoporous microparticles.

5. The method of claim 4, wherein the mesoporous nanoparticles or mesoporous microparticles are produced by sonication of the porous silicon substrate.

6. The method of claim 4, wherein the mesoporous nanoparticles comprise an average size of between about 100 nm to about 1000 nm, and the mesoporous microparticles comprise an average size of between about 1 µm to about 500 µm.

7. The method of claim 1, wherein the porous silicon substrate comprises an average pore size of between about 10 nm to about 40 nm.

8. The method of claim 1, wherein the wound is an acute wound, a chronic wound, or a wound in an individual with compromised wound healing capacity.

9. The method of claim 8, wherein the acute wound is the result of a penetrative injury, a burn, nerve damage or from elective surgery, or wherein the chronic wound is a diabetic, veneous, arterial, or decubitus ulcer.

10. The method of claim 1, wherein the wound healing antibody is a monoclonal antibody to Flightless I, or a monoclonal antibody to TNF-α.

11. The method of claim 1, wherein the administering comprises: (i) exposing the wound to a dressing or bandage that comprises the composition; or (ii) topical administration of the composition to the wound; or (iii) systemic administration of the composition.

12. A wound healing composition comprising: a porous silicon substrate, wherein the porous silicon substrate has been thermally oxidized at a temperature less than 600° C.; and a therapeutically effective amount of a wound healing antibody passively bound to pores of the substrate, or passively bound to the surface of the substrate and to pores of the substrate, wherein the composition protects the wound healing antibody from degradation in a wound.

13. The composition of claim 12, wherein the porous silicon substrate comprises nanoporous silicon, or mesoporous silicon, or nanoporous silicon and mesoporous silicon.

14. The composition of claim 12, wherein the porous silicon substrate comprises mesoporous nanoparticles, or mesoporous microparticles, or mesoporous nanoparticles and mesoporous microparticles.

15. The composition of claim 14, wherein the mesoporous nanoparticles comprise an average size of between about 100 nm to about 1000 nm, and the mesoporous microparticles comprise an average size of between about 1 µm to about 500 µm.

16. The composition of claim 12, wherein the porous silicon substrate comprises an average pore size of between about 10 nm to about 40 nm.

17. The composition of claim 12, wherein the composition is part of a dressing or bandage.

18. The method of claim 10, wherein the monoclonal antibody to TNF-α is Infliximab.

19. The composition of claim 12, wherein the wound healing antibody is a monoclonal antibody to Flightless I, or a monoclonal antibody to TNF-α.

20. The composition of claim 19, wherein the monoclonal antibody to TNF-α is Infliximab.

21. The method of claim 1, wherein the porous silicon substrate has been thermally oxidized at a temperature less than about 500° C.

22. The method of claim 1, wherein the porous silicon substrate has been thermally oxidized at a temperature of less than about 400° C.

* * * * *

SEQUENCE LISTING

```
<160> NUMBER OF SEQ ID NOS: 9

<210> SEQ ID NO 1
<211> LENGTH: 4387
<212> TYPE: DNA
<213> ORGANISM: Homo sapiens

<400> SEQUENCE: 1
aactccagca caggggggc ccgcactcct tggtgcctcc gcagtcttcg aacagacggg      60
gaaactgagg ccctaagagg cctaaagcct acacttcccc gcggaatgcg gcgggcgcgg    120
gcgggttaaa ggggcggggc cggcgctggc ccagcccgcg gctcccccca gcgccctcgc    180
cccggcgctc cctagcccgg cgcggcccgg cagcgagagc ggcgccatgg aggccaccgg    240
ggtgctgccg ttcgtgcgtg gcgtggacct cagcggcaac gacttcaagg gcggctactt    300
ccctgagaat gtcaaggcca tgaccagcct gcggtggctg aagctgaacc gcactggcct    360
ctgctacctg cccgaggagc tggccgccct gcagaagctg gaacacttgt ctgtgagcca    420
caacaacctg accacgcttc atggggagct gtccagcctg ccatcgctgc gcgccatcgt    480
ggcccgagcc aacagtctga agaattccgg agtccccgat gacatcttca agctagatga    540
tctctcagtc ctggacttga gccacaacca gctgacagag tgcccgcggg agctggagaa    600
cgccaagaac atgctggtgc tgaacctcag ccacaacagc atcgacacca tcccccaacca    660 gctcttcatc aacctcactg acctactata cctggacctc agcgagaacc gcctggagag    720
cctgcccccg cagatgcgcc gcctggtgca cctgcagacg ctcgtgctca atggaaaccc    780
cctgctgcat gcacagctcc ggcagctccc agcgatgacg gccctgcaga ccctgcacct    840
gcggagcacc cagcgcaccc agagcaacct gcccaccagc ctggagggtc tgagcaacct    900
cgcagacgtg gatctgtcct gcaatgacct gacacgggtg cccgagtgtc tgtacaccct    960
ccccagcctg cgccgcctca acctcagcag caaccagatc acggagctgt ccctgtgcat   1020
agaccagtgg gtgcacgtgg aaactctgaa cctgtcccga aatcagctca cctcactgcc   1080
ctcagccatt tgcaagctga cgcaagctgaa gaagctgtac ctgaattcca acaagctgga   1140
ctttgacggg ctgccctcag gcattggcaa gctcaccaac ctggaagagt tcatggctgc   1200
caacaacaac ctggagctgg tccctgaaag tctctgcagg tgcccaaagc tgaggaaact   1260
tgtcctgaac aagaaccacc tggtgaccct cccagaagcc atccatttcc tgacggagat   1320
cgaggtcctg gatgtgcggg agaacccaa cctggtcatg ccgccaagc ccgcagaccg   1380 tgccgctgag tggtacaaca tcgacttctc gctgcagaac cagctgcggc tagcgggtgc   1440
```

```
ctctcctgct accgtggctg cagctgcagc tgcagggagt gggcccaagg accctatggc    1500
tcgcaagatg cgactgcgga ggcgcaagga ttcagcccag gatgaccagg ccaagcaggt    1560
gctgaagggc atgtcagatg ttgcccagga gaagaacaaa aagcaggagg agagcgcaga    1620
tgcccgggcc cccagcggga aggtgcggcg ttgggaccag ggcctggaga gccccgcct     1680 tgactactcc gagttcttca cggaggacgt gggccagctg cccggactga ccatctggca    1740
gatagagaac ttcgtgcctg tgctggtgga ggaagccttc cacggcaagt tctacgaggc    1800
tgactgctac attgtgctca agacctttct ggatgacagc ggctccctca actgggagat    1860
ctactactgg attggcgggg aggccacact cgacaagaaa gcttgctctg ccatccacgc    1920
tgtcaacttg cgcaactacc tgggtgctga gtgccgcact gtccgggagg agatgggcga    1980
tgagagcgag gagttcctgc aggtgtttga caacgacatc tcctacattg agggtggaac    2040
agccagtggc ttctacactg tggaagacac acactatgtc accaggatgt atcgtgtgta    2100
tgggaaaaag aacatcaagt tggagcctgt gcccctcaag gggacctctc tggacccaag    2160 gtttgtttc  ctgctggacc gagggctaga catctacgta tggcgggggg cccaggccac    2220
actgagcagc accaccaagg ccaggctctt tgcagagaaa attaacaaga atgagcggaa    2280
agggaaggct gagatcacac tgctggtgca gggccaggag ctcccagagt tctgggaggc    2340
actgggtggg gagccctctg agatcaagaa gcacgtgcct gaagacttct ggccgccgca    2400
gcccaagctg tacaaggtgg gcctgggctt ggctacctg gagctgccac agatcaacta     2460
caagctctcc gtggaacata agcagcgtcc caaggtggag ctgatgccaa gaatgcggct    2520
gctgcagagt ctgctggaca cgcgctgcgt gtacattctg gactgttggt ccgacgtgtt    2580
catctggctc ggccgcaagt ccccgcgcct ggtgcgcgct gccgccctca gctgggtca     2640 ggagctgtgc gggatgctgc accggccacg ccatgccacg gtcagccgca gcctcgaggg    2700
caccgaggcg caggtgttca aggccaagtt caagaattgg gacgatgtgt tgacggtgga    2760
ctacacacgc aatgcggagg ccgtgctgca gagcccgggt ctctccggga aggtgaaacg    2820
cgacgccgag aagaaagacc agatgaaggc tgacctcact gcgcttttcc tgccgcggca    2880
gccgcccatg tcgctggccg aggcggagca gctgatggag gagtggaacg aagacctaga    2940
cggcatggag ggtttcgtgc tggagggcaa gaagtttgcg cggctgccgg aagaggagtt    3000
tggccacttc tacacgcagg actgctacgt cttcctctgc aggtactggg tgcctgtgga    3060
gtacgaggag gaggaaaaga aggaagacaa ggaggagaag gccgagggca agaaggcga     3120 ggaagcaacc gctgaggcag aggagaagca gccagaggag gacttccagt gcatcgtgta    3180
cttctggcag ggccgtgaag cctccaatat gggctggctc accttcacct tcagcctgca    3240
aaagaagttc gagagcctct tccctgggaa gctggaggtg gtacgcatga cgcagcagca    3300
ggagaacccc aagttcctgt cccatttcaa gaggaagttc atcatccacc ggggcaagag    3360
gaaggcggtc cagggcgccc aacagcccag cctctaccag atccgcacca acggcagcgc    3420
cctctgcacc cggtgcatcc agatcaacac cgactccagc ctcctcaact ccgagttctg    3480
cttcatcctc aaggttccct ttgagagtga ggacaaccag ggcatcgtgt atgcctgggt    3540
gggccgggca tcagaccctg acgaagccaa gttggcagaa gacatcctga acaccatgtt    3600
tgacacctcc tacagcaagc aggttatcaa cgaaggtgag gagcctgaga acttcttctg    3660
ggtgggcatt gggcacagaa gccctatga  tgacgatgcc gagtacatga acacacacg     3720 tctcttccgg tgctccaacg agaagggcta ctttgcagtg actgagaaat gctccgactt    3780
ttgccaagat gacctggcag atgatgacat catgttgcta gacaatggcc aagaggtcta    3840
```

```
catgtgggtg gggacccaga ctagccaggt ggagatcaag ctgagcctga aggcctgcca    3900
ggtatatatc cagcacatgc ggtccaagga acatgagcgg ccgcgccggc tgcgcctggt    3960
ccgcaagggc aatgagcagc acgcctttac ccgctgcttc cacgcctgga gcgccttctg    4020
caaggccctg gcctaagaca ggctggcaca gccccaggct tggtgaggaa gaggaagggg    4080
cctcatccac tgtctgctag caaagaatgt actcaggtga caccacctgc tccagccacg    4140
tccagtgcca cagtcccag tagcctcaag cagcaccaat ggggatgacc ctgacaggtg     4200
ccctcagggg tctgggaaat ccaactctct ccacagtgtg agtgcacgtg tgaagccccc    4260
tcactcttcc gctagggata aagcagatgt ggatgcccctt taagagatat taaatgcttt   4320
tattttcaat attaaaaatc agtattttta atattaaaaa aaaaaaaaaa aaaaaaaaaa    4380
aaaaaaa                                                              4387
```

<210> SEQ ID NO 2
<211> LENGTH: 1269
<212> TYPE: PRT
<213> ORGANISM: Homo sapiens

<400> SEQUENCE: 2

```
Met Glu Ala Thr Gly Val Leu Pro Phe Val Arg Gly Val Asp Leu Ser
1               5                   10                  15

Gly Asn Asp Phe Lys Gly Gly Tyr Phe Pro Glu Asn Val Lys Ala Met
            20                  25                  30

Thr Ser Leu Arg Trp Leu Lys Leu Asn Arg Thr Gly Leu Cys Tyr Leu
        35                  40                  45

Pro Glu Glu Leu Ala Ala Leu Gln Lys Leu Glu His Leu Ser Val Ser
    50                  55                  60

His Asn Asn Leu Thr Thr Leu His Gly Glu Leu Ser Ser Leu Pro Ser
65                  70                  75                  80

Leu Arg Ala Ile Val Ala Arg Ala Asn Ser Leu Lys Asn Ser Gly Val
                85                  90                  95

Pro Asp Asp Ile Phe Lys Leu Asp Asp Leu Ser Val Leu Asp Leu Ser
            100                 105                 110

His Asn Gln Leu Thr Glu Cys Pro Arg Glu Leu Glu Asn Ala Lys Asn
        115                 120                 125

Met Leu Val Leu Asn Leu Ser His Asn Ser Ile Asp Thr Ile Pro Asn
    130                 135                 140

Gln Leu Phe Ile Asn Leu Thr Asp Leu Leu Tyr Leu Asp Leu Ser Glu
145                 150                 155                 160

Asn Arg Leu Glu Ser Leu Pro Pro Gln Met Arg Arg Leu Val His Leu
                165                 170                 175

Gln Thr Leu Val Leu Asn Gly Asn Pro Leu Leu His Ala Gln Leu Arg
            180                 185                 190

Gln Leu Pro Ala Met Thr Ala Leu Gln Thr Leu His Leu Arg Ser Thr
        195                 200                 205

Gln Arg Thr Gln Ser Asn Leu Pro Thr Ser Leu Glu Gly Leu Ser Asn
    210                 215                 220

Leu Ala Asp Val Asp Leu Ser Cys Asn Asp Leu Thr Arg Val Pro Glu
225                 230                 235                 240

Cys Leu Tyr Thr Leu Pro Ser Leu Arg Arg Leu Asn Leu Ser Ser Asn
                245                 250                 255

Gln Ile Thr Glu Leu Ser Leu Cys Ile Asp Gln Trp Val His Val Glu
            260                 265                 270
```

```
Thr Leu Asn Leu Ser Arg Asn Gln Leu Thr Ser Leu Pro Ser Ala Ile
            275                 280                 285

Cys Lys Leu Ser Lys Leu Lys Lys Leu Tyr Leu Asn Ser Asn Lys Leu
        290                 295                 300

Asp Phe Asp Gly Leu Pro Ser Gly Ile Gly Lys Leu Thr Asn Leu Glu
305                 310                 315                 320

Glu Phe Met Ala Ala Asn Asn Asn Leu Glu Leu Val Pro Glu Ser Leu
                325                 330                 335

Cys Arg Cys Pro Lys Leu Arg Lys Leu Val Leu Asn Lys Asn His Leu
            340                 345                 350

Val Thr Leu Pro Glu Ala Ile His Phe Leu Thr Glu Ile Glu Val Leu
        355                 360                 365

Asp Val Arg Glu Asn Pro Asn Leu Val Met Pro Pro Lys Pro Ala Asp
370                 375                 380

Arg Ala Ala Glu Trp Tyr Asn Ile Asp Phe Ser Leu Gln Asn Gln Leu
385                 390                 395                 400

Arg Leu Ala Gly Ala Ser Pro Ala Thr Val Ala Ala Ala Ala Ala Ala
                405                 410                 415

Gly Ser Gly Pro Lys Asp Pro Met Ala Arg Lys Met Arg Leu Arg Arg
            420                 425                 430

Arg Lys Asp Ser Ala Gln Asp Gln Ala Lys Gln Val Leu Lys Gly
        435                 440                 445

Met Ser Asp Val Ala Gln Glu Lys Asn Lys Gln Glu Glu Ser Ala
        450                 455                 460

Asp Ala Arg Ala Pro Ser Gly Lys Val Arg Arg Trp Asp Gln Gly Leu
465                 470                 475                 480

Glu Lys Pro Arg Leu Asp Tyr Ser Glu Phe Phe Thr Glu Asp Val Gly
            485                 490                 495

Gln Leu Pro Gly Leu Thr Ile Trp Gln Ile Glu Asn Phe Val Pro Val
                500                 505                 510

Leu Val Glu Glu Ala Phe His Gly Lys Phe Tyr Glu Ala Asp Cys Tyr
            515                 520                 525

Ile Val Leu Lys Thr Phe Leu Asp Asp Ser Gly Ser Leu Asn Trp Glu
        530                 535                 540

Ile Tyr Tyr Trp Ile Gly Gly Glu Ala Thr Leu Asp Lys Lys Ala Cys
545                 550                 555                 560

Ser Ala Ile His Ala Val Asn Leu Arg Asn Tyr Leu Gly Ala Glu Cys
                565                 570                 575

Arg Thr Val Arg Glu Glu Met Gly Asp Glu Ser Glu Glu Phe Leu Gln
            580                 585                 590

Val Phe Asp Asn Asp Ile Ser Tyr Ile Glu Gly Gly Thr Ala Ser Gly
        595                 600                 605

Phe Tyr Thr Val Glu Asp Thr His Tyr Val Thr Arg Met Tyr Arg Val
        610                 615                 620

Tyr Gly Lys Lys Asn Ile Lys Leu Glu Pro Val Pro Leu Lys Gly Thr
625                 630                 635                 640

Ser Leu Asp Pro Arg Phe Val Phe Leu Leu Asp Arg Gly Leu Asp Ile
                645                 650                 655

Tyr Val Trp Arg Gly Ala Gln Ala Thr Leu Ser Ser Thr Thr Lys Ala
            660                 665                 670

Arg Leu Phe Ala Glu Lys Ile Asn Lys Asn Glu Arg Lys Gly Lys Ala
        675                 680                 685
```

-continued

```
Glu Ile Thr Leu Leu Val Gln Gly Gln Glu Leu Pro Glu Phe Trp Glu
690                 695                 700
Ala Leu Gly Gly Glu Pro Ser Glu Ile Lys Lys His Val Pro Glu Asp
705                 710                 715                 720
Phe Trp Pro Pro Gln Pro Lys Leu Tyr Lys Val Gly Leu Gly Leu Gly
                725                 730                 735
Tyr Leu Glu Leu Pro Gln Ile Asn Tyr Lys Leu Ser Val Glu His Lys
            740                 745                 750
Gln Arg Pro Lys Val Glu Leu Met Pro Arg Met Arg Leu Gln Ser
        755                 760                 765
Leu Leu Asp Thr Arg Cys Val Tyr Ile Leu Asp Cys Trp Ser Asp Val
770                 775                 780
Phe Ile Trp Leu Gly Arg Lys Ser Pro Arg Leu Val Arg Ala Ala Ala
785                 790                 795                 800
Leu Lys Leu Gly Gln Glu Leu Cys Gly Met Leu His Arg Pro Arg His
                805                 810                 815
Ala Thr Val Ser Arg Ser Leu Glu Gly Thr Glu Ala Gln Val Phe Lys
            820                 825                 830
Ala Lys Phe Lys Asn Trp Asp Asp Val Leu Thr Val Asp Tyr Thr Arg
        835                 840                 845
Asn Ala Glu Ala Val Leu Gln Ser Pro Gly Leu Ser Gly Lys Val Lys
850                 855                 860
Arg Asp Ala Glu Lys Lys Asp Gln Met Lys Ala Asp Leu Thr Ala Leu
865                 870                 875                 880
Phe Leu Pro Arg Gln Pro Pro Met Ser Leu Ala Glu Ala Glu Gln Leu
                885                 890                 895
Met Glu Glu Trp Asn Glu Asp Leu Asp Gly Met Glu Gly Phe Val Leu
            900                 905                 910
Glu Gly Lys Lys Phe Ala Arg Leu Pro Glu Glu Glu Phe Gly His Phe
        915                 920                 925
Tyr Thr Gln Asp Cys Tyr Val Phe Leu Cys Arg Tyr Trp Val Pro Val
930                 935                 940
Glu Tyr Glu Glu Glu Lys Lys Glu Asp Lys Glu Glu Lys Ala Glu
945                 950                 955                 960
Gly Lys Glu Gly Glu Glu Ala Thr Ala Glu Ala Glu Glu Lys Gln Pro
                965                 970                 975
Glu Glu Asp Phe Gln Cys Ile Val Tyr Phe Trp Gln Gly Arg Glu Ala
            980                 985                 990
Ser Asn Met Gly Trp Leu Thr Phe  Thr Phe Ser Leu Gln  Lys Lys Phe
        995                 1000                1005
Glu Ser  Leu Phe Pro Gly Lys  Leu Glu Val Val Arg  Met Thr Gln
        1010                1015                1020
Gln Gln  Glu Asn Pro Lys Phe  Leu Ser His Phe Lys  Arg Lys Phe
        1025                1030                1035
Ile Ile  His Arg Gly Lys Arg  Lys Ala Val Gln Gly  Ala Gln Gln
        1040                1045                1050
Pro Ser  Leu Tyr Gln Ile Arg  Thr Asn Gly Ser Ala  Leu Cys Thr
        1055                1060                1065
Arg Cys  Ile Gln Ile Asn Thr  Asp Ser Ser Leu Leu  Asn Ser Glu
        1070                1075                1080
Phe Cys  Phe Ile Leu Lys Val  Pro Phe Glu Ser Glu  Asp Asn Gln
        1085                1090                1095
```

Gly Ile Val Tyr Ala Trp Val Gly Arg Ala Ser Asp Pro Asp Glu
    1100                1105                1110

Ala Lys Leu Ala Glu Asp Ile Leu Asn Thr Met Phe Asp Thr Ser
    1115                1120                1125

Tyr Ser Lys Gln Val Ile Asn Glu Gly Glu Pro Glu Asn Phe
    1130                1135                1140

Phe Trp Val Gly Ile Gly Ala Gln Lys Pro Tyr Asp Asp Ala
    1145                1150                1155

Glu Tyr Met Lys His Thr Arg Leu Phe Arg Cys Ser Asn Glu Lys
    1160                1165                1170

Gly Tyr Phe Ala Val Thr Glu Lys Cys Ser Asp Phe Cys Gln Asp
    1175                1180                1185

Asp Leu Ala Asp Asp Asp Ile Met Leu Leu Asp Asn Gly Gln Glu
    1190                1195                1200

Val Tyr Met Trp Val Gly Thr Gln Thr Ser Gln Val Glu Ile Lys
    1205                1210                1215

Leu Ser Leu Lys Ala Cys Gln Val Tyr Ile Gln His Met Arg Ser
    1220                1225                1230

Lys Glu His Glu Arg Pro Arg Arg Leu Arg Leu Val Arg Lys Gly
    1235                1240                1245

Asn Glu Gln His Ala Phe Thr Arg Cys Phe His Ala Trp Ser Ala
    1250                1255                1260

Phe Cys Lys Ala Leu Ala
    1265

<210> SEQ ID NO 3
<211> LENGTH: 4208
<212> TYPE: DNA
<213> ORGANISM: Homo sapiens

<400> SEQUENCE: 3

```
ttcctgtccc gctcggctcc aggccctgcg tgtcccaggg actgcggccg gggcggggtg      60
gggctctccc ctggccagga atggacctcc gaggcctccg cccagtgcct ggcggctact     120
tccctgagaa tgtcaaggcc atgaccagcc tgcggtggct gaagctgaac cgcactggcc     180
tctgctacct gcccgaggag ctggccgccc tgcagaagct ggaacacttg tctgtgagcc     240
acaacaacct gaccacgctt catggggagc tgtccagcct gccatcgctg cgcgccatcg     300
tggcccgagc caacagtctg aagaattccg agtccccga tgacatcttc aagctagatg     360
atctctcagt cctggacttg agccacaacc agctgacaga gtgcccgcgg agctggagag     420
acgccaagaa catgctggtg ctgaacctca gccacaacag catcgacacc atccccaacc     480
agctcttcat caacctcact gacctactat acctggacct cagcgagaac cgcctggaga     540
gcctgccccc gcagatgcgc cgcctggtgc acctgcagac gctcgtgctc aatggaaacc     600
ccctgctgca tgcacagctc cggcagctcc agcgatgac ggccctgcag acctgcacc     660
tgcggagcac ccagcgcacc cagagcaacc tgcccaccag cctggagggt ctgagcaacc     720
tcgcagacgt ggatctgtcc tgcaatgacc tgacacgggt gcccgagtgt ctgtacaccc     780
tccccagcct gcgccgcctc aacctcagca gcaaccagat cacggagctg tcccgtgca     840
tagaccagtg ggtgcacgtg aaactctga acctgtcccg aaatcagctc acctcactgc     900
cctcagccat ttgcaagctg agcaagctga agaagctgta cctgaattcc aacaagctgg     960
actttgacgg gctgccctca ggcattggca agctcaccaa cctggaagag ttcatggctg    1020
ccaacaacaa cctggagctg gtccctgaaa gtctctgcag gtgcccaaag ctgaggaaac    1080
```

```
ttgtcctgaa caagaaccac ctggtgaccc tcccagaagc catccatttc ctgacggaga    1140
tcgaggtcct ggatgtgcgg gagaacccca acctggtcat gccgcccaag cccgcagacc    1200
gtgccgctga gtggtacaac atcgacttct cgctgcagaa ccagctgcgg ctagcgggtg    1260
cctctcctgc taccgtggct gcagctgcag ctgcagggag tgggcccaag gaccctatgg    1320
ctcgcaagat gcgactgcgg aggcgcaagg attcagccca ggatgaccag gccaagcagg    1380
tgctgaaggg catgtcagat gttgcccagg agaagaacaa aaagcaggag gagagcgcag    1440
atgcccgggc ccccagcggg aaggtgcggc gttgggacca gggcctggag aagccccgcc    1500
ttgactactc cgagttcttc acggaggacg tgggccagct gcccggactg accatctggc    1560
agatagagaa cttcgtgcct gtgctggtgg aggaagcctt ccacggcaag ttctacgagg    1620
ctgactgcta cattgtgctc aagacctttc tggatgacag cggctcccct aactgggaga    1680
tctactactg gattggcggg gaggccacac tcgacaagaa agcttgctct gccatccacg    1740
ctgtcaactt gcgcaactac ctgggtgctg agtgccgcac tgtccgggag gagatgggcg    1800
atgagagcga ggagttcctg caggtgtttg acaacgacat ctcctacatt gagggtggaa    1860
cagccagtgg cttctacact gtggaagaca cacactatgt caccaggatg tatcgtgtgt    1920
atgggaaaaa gaacatcaag ttggagcctg tgcccctcaa ggggacctct ctggacccaa    1980
ggtttgtttt cctgctggac cgagggctag acatctacgt atggcggggg gcccaggcca    2040
cactgagcag caccaccaag gccaggctct ttgcagagaa aattaacaag aatgagcgga    2100
aagggaaggc tgagatcaca ctgctggtgc agggccagga gctcccagag ttctgggagg    2160
cactgggtgg ggagccctct gagatcaaga agcacgtgcc tgaagacttc tggccgccgc    2220
agcccaagct gtacaaggtg ggcctgggct tgggctacct ggagctgcca cagatcaact    2280
acaagctctc cgtggaacat aagcagcgtc ccaaggtgga gctgatgcca gaatgcggc    2340
tgctgcagag tctgctggac acgcgctgcg tgtacattct ggactgttgg tccgacgtgt    2400
tcatctggct cggccgcaag tccccgcgcc tggtgcgcgc tgccgccctc aagctgggtc    2460
aggagctgtg cgggatgctg caccggccac gccatgccac ggtcagccgc agcctcgagg    2520
gcaccgaggc gcaggtgttc aaggccaagt tcaagaattg ggacgatgtg ttgacggtgg    2580
actacacacg caatgcggag gccgtgctgc agagcccggg tctctccggg aaggtgaaac    2640
gcgacgccga aagaaagac cagatgaagg ctgacctcac tgcgcttttc ctgccgcggc    2700
agccgcccat gtcgctggcc gaggcggagc agctgatgga ggagtggaac gaagacctag    2760
acggcatgga gggtttcgtg ctggagggca gaaagtttgc gcggctgccg gaagaggagt    2820
ttggccactt ctacacgcag gactgctacg tcttcctctg caggtactgg gtgcctgtgg    2880
agtacgagga ggaggaaaag aaggaagaca aggaggagaa ggccgagggc aaagaaggcg    2940
aggaagcaac cgctgaggca gaggagaagc agccagagga ggacttccag tgcatcgtgt    3000
acttctggca gggccgtgaa gcctccaata tgggctggct cacccttcacc ttcagcctgc    3060
aaaagaagtt cgagagcctc ttccctggga agctggaggt ggtacgcatg acgcagcagc    3120
aggagaaccc caagttcctg tcccatttca gaggaagtt catcatccac cggggcaaga    3180
ggaaggcggt ccagggcgcc caacagccca gcctctacca gatccgcacc aacgcagcg    3240
ccctctgcac ccggtgcatc cagatcaaca ccgactccag cctcctcaac tccgagttct    3300
gcttcatcct caaggttccc tttgagagtg aggacaacca gggcatcgtg tatgcctggg    3360
tgggccgggc atcagaccct gacgaagcca agttggcaga agacatcctg aacaccatgt    3420
ttgacacctc ctacagcaag caggttatca acgaaggtga ggagcctgag aacttcttct    3480
```

-continued

```
gggtgggcat tggggcacag aagccctatg atgacgatgc cgagtacatg aaacacacac    3540
gtctcttccg gtgctccaac gagaagggct actttgcagt gactgagaaa tgctccgact    3600
tttgccaaga tgacctggca gatgatgaca tcatgttgct agacaatggc caagaggtct    3660
acatgtgggt ggggacccag actagccagg tggagatcaa gctgagcctg aaggcctgcc    3720
aggtatatat ccagcacatg cggtccaagg aacatgagcg gccgcgccgg ctgcgcctgg    3780
tccgcaaggg caatgagcag cacgccttta cccgctgctt ccacgcctgg agcgccttct    3840
gcaaggccct ggcctaagac aggctggcac agccccaggc ttggtgagga agaggaaggg    3900
gcctcatcca ctgtctgcta gcaaagaatg tactcaggtg acaccacctg ctccagccac    3960
gtccagtgcc acagtcccca gtagcctcaa gcagcaccaa tggggatgac cctgacaggt    4020
gccctcaggg gtctgggaaa tccaactctc tccacagtgt gagtgcacgt gtgaagcccc    4080
ctcactcttc cgctagggat aaagcagatg tggatgccct taagagata ttaaatgctt    4140
ttattttcaa tattaaaaat cagtatttt aatattaaaa aaaaaaaaaa aaaaaaaaa    4200
aaaaaaaa                                                            4208
```

<210> SEQ ID NO 4
<211> LENGTH: 1258
<212> TYPE: PRT
<213> ORGANISM: Homo sapiens

<400> SEQUENCE: 4

```
Met Asp Leu Arg Gly Leu Arg Pro Val Pro Gly Gly Tyr Phe Pro Glu
1               5                   10                  15

Asn Val Lys Ala Met Thr Ser Leu Arg Trp Leu Lys Leu Asn Arg Thr
            20                  25                  30

Gly Leu Cys Tyr Leu Pro Glu Glu Leu Ala Ala Leu Gln Lys Leu Glu
        35                  40                  45

His Leu Ser Val Ser His Asn Asn Leu Thr Thr Leu His Gly Glu Leu
    50                  55                  60

Ser Ser Leu Pro Ser Leu Arg Ala Ile Val Ala Arg Ala Asn Ser Leu
65                  70                  75                  80

Lys Asn Ser Gly Val Pro Asp Asp Ile Phe Lys Leu Asp Asp Leu Ser
                85                  90                  95

Val Leu Asp Leu Ser His Asn Gln Leu Thr Glu Cys Pro Arg Glu Leu
            100                 105                 110

Glu Asn Ala Lys Asn Met Leu Val Leu Asn Leu Ser His Asn Ser Ile
        115                 120                 125

Asp Thr Ile Pro Asn Gln Leu Phe Ile Asn Leu Thr Asp Leu Leu Tyr
    130                 135                 140

Leu Asp Leu Ser Glu Asn Arg Leu Glu Ser Leu Pro Pro Gln Met Arg
145                 150                 155                 160

Arg Leu Val His Leu Gln Thr Leu Val Leu Asn Gly Asn Pro Leu Leu
                165                 170                 175

His Ala Gln Leu Arg Gln Leu Pro Ala Met Thr Ala Leu Gln Thr Leu
            180                 185                 190

His Leu Arg Ser Thr Gln Arg Thr Gln Ser Asn Leu Pro Thr Ser Leu
        195                 200                 205

Glu Gly Leu Ser Asn Leu Ala Asp Val Asp Leu Ser Cys Asn Asp Leu
    210                 215                 220

Thr Arg Val Pro Glu Cys Leu Tyr Thr Leu Pro Ser Leu Arg Arg Leu
225                 230                 235                 240
```

```
Asn Leu Ser Ser Asn Gln Ile Thr Glu Leu Ser Leu Cys Ile Asp Gln
            245                 250                 255

Trp Val His Val Glu Thr Leu Asn Leu Ser Arg Asn Gln Leu Thr Ser
        260                 265                 270

Leu Pro Ser Ala Ile Cys Lys Leu Ser Lys Leu Lys Lys Leu Tyr Leu
        275                 280                 285

Asn Ser Asn Lys Leu Asp Phe Asp Gly Leu Pro Ser Gly Ile Gly Lys
        290                 295                 300

Leu Thr Asn Leu Glu Glu Phe Met Ala Ala Asn Asn Leu Glu Leu
305                 310                 315                 320

Val Pro Glu Ser Leu Cys Arg Cys Pro Lys Leu Arg Lys Leu Val Leu
                325                 330                 335

Asn Lys Asn His Leu Val Thr Leu Pro Glu Ala Ile His Phe Leu Thr
            340                 345                 350

Glu Ile Glu Val Leu Asp Val Arg Glu Asn Pro Asn Leu Val Met Pro
        355                 360                 365

Pro Lys Pro Ala Asp Arg Ala Glu Trp Tyr Asn Ile Asp Phe Ser
        370                 375                 380

Leu Gln Asn Gln Leu Arg Leu Ala Gly Ala Ser Pro Ala Thr Val Ala
385                 390                 395                 400

Ala Ala Ala Ala Gly Ser Gly Pro Lys Asp Pro Met Ala Arg Lys
                405                 410                 415

Met Arg Leu Arg Arg Arg Lys Asp Ser Ala Gln Asp Gln Ala Lys
                420                 425                 430

Gln Val Leu Lys Gly Met Ser Asp Val Ala Gln Glu Lys Asn Lys Lys
        435                 440                 445

Gln Glu Glu Ser Ala Asp Ala Arg Ala Pro Ser Gly Lys Val Arg Arg
        450                 455                 460

Trp Asp Gln Gly Leu Glu Lys Pro Arg Leu Asp Tyr Ser Glu Phe Phe
465                 470                 475                 480

Thr Glu Asp Val Gly Gln Leu Pro Gly Leu Thr Ile Trp Gln Ile Glu
                485                 490                 495

Asn Phe Val Pro Val Leu Val Glu Glu Ala Phe His Gly Lys Phe Tyr
            500                 505                 510

Glu Ala Asp Cys Tyr Ile Val Leu Lys Thr Phe Leu Asp Asp Ser Gly
            515                 520                 525

Ser Leu Asn Trp Glu Ile Tyr Tyr Trp Ile Gly Gly Glu Ala Thr Leu
        530                 535                 540

Asp Lys Lys Ala Cys Ser Ala Ile His Ala Val Asn Leu Arg Asn Tyr
545                 550                 555                 560

Leu Gly Ala Glu Cys Arg Thr Val Arg Glu Glu Met Gly Asp Glu Ser
                565                 570                 575

Glu Glu Phe Leu Gln Val Phe Asp Asn Asp Ile Ser Tyr Ile Glu Gly
            580                 585                 590

Gly Thr Ala Ser Gly Phe Tyr Thr Val Glu Asp Thr His Tyr Val Thr
        595                 600                 605

Arg Met Tyr Arg Val Tyr Gly Lys Lys Asn Ile Lys Leu Glu Pro Val
        610                 615                 620

Pro Leu Lys Gly Thr Ser Leu Asp Pro Arg Phe Val Phe Leu Leu Asp
625                 630                 635                 640

Arg Gly Leu Asp Ile Tyr Val Trp Arg Gly Ala Gln Ala Thr Leu Ser
                645                 650                 655
```

-continued

Ser Thr Thr Lys Ala Arg Leu Phe Ala Glu Lys Ile Asn Lys Asn Glu
                660                 665                 670

Arg Lys Gly Lys Ala Glu Ile Thr Leu Leu Val Gln Gly Gln Glu Leu
                675                 680                 685

Pro Glu Phe Trp Glu Ala Leu Gly Gly Glu Pro Ser Glu Ile Lys Lys
                690                 695                 700

His Val Pro Glu Asp Phe Trp Pro Gln Pro Lys Leu Tyr Lys Val
705                 710                 715                 720

Gly Leu Gly Leu Gly Tyr Leu Glu Leu Pro Gln Ile Asn Tyr Lys Leu
                725                 730                 735

Ser Val Glu His Lys Gln Arg Pro Lys Val Glu Leu Met Pro Arg Met
                740                 745                 750

Arg Leu Leu Gln Ser Leu Leu Asp Thr Arg Cys Val Tyr Ile Leu Asp
                755                 760                 765

Cys Trp Ser Asp Val Phe Ile Trp Leu Gly Arg Lys Ser Pro Arg Leu
                770                 775                 780

Val Arg Ala Ala Ala Leu Lys Leu Gly Gln Glu Leu Cys Gly Met Leu
785                 790                 795                 800

His Arg Pro Arg His Ala Thr Val Ser Arg Ser Leu Glu Gly Thr Glu
                805                 810                 815

Ala Gln Val Phe Lys Ala Lys Phe Lys Asn Trp Asp Val Leu Thr
                820                 825                 830

Val Asp Tyr Thr Arg Asn Ala Glu Ala Val Leu Gln Ser Pro Gly Leu
                835                 840                 845

Ser Gly Lys Val Lys Arg Asp Ala Glu Lys Lys Asp Gln Met Lys Ala
850                 855                 860

Asp Leu Thr Ala Leu Phe Leu Pro Arg Gln Pro Met Ser Leu Ala
865                 870                 875                 880

Glu Ala Glu Gln Leu Met Glu Glu Trp Asn Glu Asp Leu Asp Gly Met
                885                 890                 895

Glu Gly Phe Val Leu Glu Gly Lys Lys Phe Ala Arg Leu Pro Glu Glu
                900                 905                 910

Glu Phe Gly His Phe Tyr Thr Gln Asp Cys Tyr Val Phe Leu Cys Arg
                915                 920                 925

Tyr Trp Val Pro Val Glu Tyr Glu Glu Glu Lys Lys Glu Asp Lys
                930                 935                 940

Glu Glu Lys Ala Glu Gly Lys Glu Gly Glu Ala Thr Ala Glu Ala
945                 950                 955                 960

Glu Glu Lys Gln Pro Glu Glu Asp Phe Gln Cys Ile Val Tyr Phe Trp
                965                 970                 975

Gln Gly Arg Glu Ala Ser Asn Met Gly Trp Leu Thr Phe Thr Phe Ser
                980                 985                 990

Leu Gln Lys Lys Phe Glu Ser Leu Phe Pro Gly Lys Leu Glu Val Val
                995                 1000                1005

Arg Met Thr Gln Gln Gln Glu Asn Pro Lys Phe Leu Ser His Phe
        1010                1015                1020

Lys Arg Lys Phe Ile Ile His Arg Gly Leu Arg Lys Ala Val Gln
        1025                1030                1035

Gly Ala Gln Gln Pro Ser Leu Tyr Gln Ile Arg Thr Asn Gly Ser
        1040                1045                1050

Ala Leu Cys Thr Arg Cys Ile Gln Ile Asn Thr Asp Ser Ser Leu
        1055                1060                1065

| | | | | | | | | | | | |
|---|---|---|---|---|---|---|---|---|---|---|---|
|Leu|Asn|Ser|Glu|Phe|Cys|Phe|Ile|Leu|Lys|Val|Pro|Phe|Glu|Ser|
|1070| | | | |1075| | | | |1080| | | | |

Glu Asp Asn Gln Gly Ile Val Tyr Ala Trp Val Gly Arg Ala Ser
    1085                1090                1095

Asp Pro Asp Glu Ala Lys Leu Ala Glu Asp Ile Leu Asn Thr Met
    1100                1105                1110

Phe Asp Thr Ser Tyr Ser Lys Gln Val Ile Asn Glu Gly Glu Glu
    1115                1120                1125

Pro Glu Asn Phe Phe Trp Val Gly Ile Gly Ala Gln Lys Pro Tyr
    1130                1135                1140

Asp Asp Asp Ala Glu Tyr Met Lys His Thr Arg Leu Phe Arg Cys
    1145                1150                1155

Ser Asn Glu Lys Gly Tyr Phe Ala Val Thr Glu Lys Cys Ser Asp
    1160                1165                1170

Phe Cys Gln Asp Asp Leu Ala Asp Asp Ile Met Leu Leu Asp
    1175                1180                1185

Asn Gly Gln Glu Val Tyr Met Trp Val Gly Thr Gln Thr Ser Gln
    1190                1195                1200

Val Glu Ile Lys Leu Ser Leu Lys Ala Cys Gln Val Tyr Ile Gln
    1205                1210                1215

His Met Arg Ser Lys Glu His Glu Arg Pro Arg Arg Leu Arg Leu
    1220                1225                1230

Val Arg Lys Gly Asn Glu Gln His Ala Phe Thr Arg Cys Phe His
    1235                1240                1245

Ala Trp Ser Ala Phe Cys Lys Ala Leu Ala
    1250                1255

<210> SEQ ID NO 5
<211> LENGTH: 4222
<212> TYPE: DNA
<213> ORGANISM: Homo sapiens

<400> SEQUENCE: 5

```
aactccagca caggggggc cgcactcct tggtgcctcc gcagtcttcg aacagacggg    60
gaaactgagg ccctaagagg cctaaagcct acacttcccc gcggaatgcg gcgggcgcgg   120
gcgggttaaa ggggcggggc cggcgctggc ccagcccgcg gctcccccca gcgccctcgc   180
cccggcgctc cctagcccgg cgcggccccgg cagcgagagc ggcgccatgg aggccaccgg   240
ggtgctgccg ttcgtgcgtg cgtggaccct cagcggcaac gacttcaagg gcggctactt   300
ccctgagaat gtcaaggcca tgaccagcct gcggtggctg aagctgaacc gcactggcct   360
ctgctacctg cccgaggagc tggccgcccc gcagaagctg aacacttgt ctgtgagcca   420 caacaacctg accacgcttc atggggagct gtccagcctg ccatcgctgc gcgccatcgt   480
ggcccgagcc aacagtctga gaattccgg agtccccgat gacatcttca agctagatga   540
tctctcagtc ctggacttga gccacaacca gctgacagag tgcccgcggg agctggagaa   600
cgccaagaac atgctggtgc tgaacctcag ccacaacagg cagctcccag cgatgacggc   660
cctgcagacc ctgcacctgc ggagcacccca gcgcacccag agcaacctgc ccaccagcct   720
ggagggtctg agcaacctcg cagacgtgga tctgtcctgc aatgacctga cacgggtgcc   780
cgagtgtctg tacaccctcc ccagcctgcg ccgcctcaac ctcagcagca accagatcac   840
ggagctgtcc ctgtgcatag accagtgggt gcacgtggaa actctgaacc tgtcccgaaa   900
tcagctcacc tcactgccct cagccatttg caagctgagc aagctgaaga agctgtacct   960
```

```
gaattccaac aagctggact tgacgggct gccctcaggc attggcaagc tcaccaacct      1020
ggaagagttc atggctgcca acaacaacct ggagctggtc cctgaaagtc tctgcaggtg      1080
cccaaagctg aggaaacttg tcctgaacaa gaaccacctg gtgaccctcc cagaagccat      1140
ccatttcctg acggagatcg aggtcctgga tgtgcgggag aaccccaacc tggtcatgcc      1200
gcccaagccc gcagaccgtg ccgctgagtg gtacaacatc gacttctcgc tgcagaacca      1260
gctgcggcta gcgggtgcct ctcctgctac cgtggctgca gctgcagctg ggagtgggcc      1320
caaggaccct atggctcgca agatgcgact gcggaggcgc aaggattcag cccaggatga      1380
ccaggccaag caggtgctga agggcatgtc agatgttgcc caggagaaga acaaaaagca      1440
ggaggagagc gcagatgccc gggcccccag cgggaaggtg cggcgttggg accagggcct      1500
ggagaagccc cgccttgact actccgagtt cttcacggag gacgtgggcc agctgcccgg      1560
actgaccatc tggcagatag agaacttcgt gcctgtgctg gtggaggaag ccttccacgg      1620
caagttctac gaggctgact gctacattgt gctcaagacc tttctggatg acagcggctc      1680
cctcaactgg gagatctact actggattgg cggggaggcc acactcgaca gaaaagcttg      1740
ctctgccatc cacgctgtca acttgcgcaa ctacctgggt gctgagtgcc gcactgtccg      1800
ggaggagatg ggcgatgaga gcgaggagtt cctgcaggtg tttgacaacg acatctccta      1860
cattgagggt ggaacagcca gtggcttcta cactgtggaa gacacacact atgtcaccag      1920
gatgtatcgt gtgtatggga aaagaacat caagttggag cctgtgcccc tcaaggggac      1980
ctctctggac ccaaggtttg ttttcctgct ggaccgaggg ctagacatct acgtatggcg      2040
gggggcccag gccacactga gcagcaccac caaggccagg ctctttgcag agaaaattaa      2100
caagaatgag cggaaaggga aggctgagat cacactgctg gtgcagggcc aggagctccc      2160
agagttctgg gaggcactgg gtggggagcc ctctgagatc aagaagcacg tgcctgaaga      2220
cttctggccg ccgcagccca gctgtacaa ggtgggcctg gcttgggct acctggagct      2280
gccacagatc aactcaagc tctccgtgga acataagcag cgtcccaagg tggagctgat      2340
gccaagaatg cggctgctgc agagtctgct ggacacgcgc tgcgtgtaca ttctggactg      2400
ttggtccgac gtgttcatct ggctcggccg caagtcccg cgcctggtgc gcgctgccgc      2460
cctcaagctg ggtcaggagc tgtgcgggat gctgcaccgg ccacgccatg ccacggtcag      2520
ccgcagcctc gagggcaccg aggcgcaggt gttcaaggcc aagttcaaga attgggacga      2580
tgtgttgacg gtggactaca cacgcaatgc ggaggccgtg ctgcagagcc cgggtctctc      2640
cgggaaggtg aaacgcgacg ccgagaagaa agaccagatg aaggctgacc tcactgcgct      2700
tttcctgccg cggcagccgc ccatgtcgct ggccgaggcg gagcagctga tggaggagtg      2760
gaacgaagac ctagacggca tggagggttt cgtgctggag ggcaagaagt ttgcgcggct      2820
gccggaagag gagtttggcc acttctacac gcaggactgc tacgtcttcc tctgcaggta      2880
ctgggtgcct gtggagtacg aggaggagga aagaaggaa gacaaggagg agaaggccga      2940
gggcaaagaa ggcgaggaag caaccgctga ggcagaggag aagcagccag aggaggactt      3000
ccagtgcatc gtgtacttct ggcagggccg tgaagcctcc aatatgggct ggctcacctt      3060
cacccttcagc ctgcaaaaga agttcgagag cctcttccct gggaagctgg aggtggtacg      3120
catgacgcag cagcaggaga accccaagtt cctgtcccat ttcaagagga agttcatcat      3180
ccaccggggc aagaggaagg cggtccaggg cgcccaacag cccagcctct accagatccg      3240
caccaacggc agcgccctct gcacccgtg catccagatc aacaccgact ccagcctcct      3300
caactccgag ttctgcttca tcctcaaggt tcccctttgag agtgaggaca accagggcat      3360
```

| | |
|---|---|
| cgtgtatgcc tgggtgggcc gggcatcaga ccctgacgaa gccaagttgg cagaagacat | 3420 |
| cctgaacacc atgtttgaca cctcctacag caagcaggtt atcaacgaag gtgaggagcc | 3480 |
| tgagaacttc ttctgggtgg cattggggc acagaagccc tatgatgacg atgccgagta | 3540 |
| catgaaacac acacgtctct tccggtgctc aacgagaag ggctactttg cagtgactga | 3600 |
| gaaatgctcc gacttttgcc aagatgacct ggcagatgat gacatcatgt tgctagacaa | 3660 |
| tggccaagag gtctacatgt gggtggggac ccagactagc caggtggaga tcaagctgag | 3720 |
| cctgaaggcc tgccaggtat atatccagca catgcggtcc aaggaacatg agcggccgcg | 3780 |
| ccggctgcgc ctggtccgca agggcaatga gcagcacgcc tttacccgct gcttccacgc | 3840 |
| ctggagcgcc ttctgcaagg ccctggccta agacaggctg gcacagcccc aggcttggtg | 3900 |
| aggaagagga agggcctca tccactgtct gctagcaaag aatgtactca ggtgacacca | 3960 |
| cctgctccag ccacgtccag tgccacagtc cccagtagcc tcaagcagca ccaatgggga | 4020 |
| tgaccctgac aggtgccctc aggggtctgg gaaatccaac tctctccaca gtgtgagtgc | 4080 |
| acgtgtgaag ccccctcact cttccgctag ggataaagca gatgtggatg cccttttaaga | 4140 |
| gatattaaat gcttttattt tcaatattaa aaatcagtat ttttaatatt aaaaaaaaaa | 4200 |
| aaaaaaaaaa aaaaaaaaaa aa | 4222 |

<210> SEQ ID NO 6
<211> LENGTH: 1214
<212> TYPE: PRT
<213> ORGANISM: Homo sapiens

<400> SEQUENCE: 6

```
Met Glu Ala Thr Gly Val Leu Pro Phe Val Arg Gly Val Asp Leu Ser
1               5                   10                  15

Gly Asn Asp Phe Lys Gly Gly Tyr Phe Pro Glu Asn Val Lys Ala Met
            20                  25                  30

Thr Ser Leu Arg Trp Leu Lys Leu Asn Arg Thr Gly Leu Cys Tyr Leu
        35                  40                  45

Pro Glu Glu Leu Ala Ala Leu Gln Lys Leu Glu His Leu Ser Val Ser
    50                  55                  60

His Asn Asn Leu Thr Thr Leu His Gly Glu Leu Ser Ser Leu Pro Ser
65                  70                  75                  80

Leu Arg Ala Ile Val Ala Arg Ala Asn Ser Leu Lys Asn Ser Gly Val
                85                  90                  95

Pro Asp Asp Ile Phe Lys Leu Asp Asp Leu Ser Val Leu Asp Leu Ser
            100                 105                 110

His Asn Gln Leu Thr Glu Cys Pro Arg Glu Leu Glu Asn Ala Lys Asn
        115                 120                 125

Met Leu Val Leu Asn Leu Ser His Asn Arg Gln Leu Pro Ala Met Thr
    130                 135                 140

Ala Leu Gln Thr Leu His Leu Arg Ser Thr Gln Arg Thr Gln Ser Asn
145                 150                 155                 160

Leu Pro Thr Ser Leu Glu Gly Leu Ser Asn Leu Ala Asp Val Asp Leu
                165                 170                 175

Ser Cys Asn Asp Leu Thr Arg Val Pro Glu Cys Leu Tyr Thr Leu Pro
            180                 185                 190

Ser Leu Arg Arg Leu Asn Leu Ser Ser Asn Gln Ile Thr Glu Leu Ser
        195                 200                 205

Leu Cys Ile Asp Gln Trp Val His Val Glu Thr Leu Asn Leu Ser Arg
    210                 215                 220
```

-continued

```
Asn Gln Leu Thr Ser Leu Pro Ser Ala Ile Cys Lys Leu Ser Lys Leu
225                 230                 235                 240

Lys Lys Leu Tyr Leu Asn Ser Asn Lys Leu Asp Phe Asp Gly Leu Pro
            245                 250                 255

Ser Gly Ile Gly Lys Leu Thr Asn Leu Glu Glu Phe Met Ala Ala Asn
        260                 265                 270

Asn Asn Leu Glu Leu Val Pro Glu Ser Leu Cys Arg Cys Pro Lys Leu
            275                 280                 285

Arg Lys Leu Val Leu Asn Lys Asn His Leu Val Thr Leu Pro Glu Ala
        290                 295                 300

Ile His Phe Leu Thr Glu Ile Glu Val Leu Asp Val Arg Glu Asn Pro
305                 310                 315                 320

Asn Leu Val Met Pro Pro Lys Pro Ala Asp Arg Ala Ala Glu Trp Tyr
                325                 330                 335

Asn Ile Asp Phe Ser Leu Gln Asn Gln Leu Arg Leu Ala Gly Ala Ser
            340                 345                 350

Pro Ala Thr Val Ala Ala Ala Ala Gly Ser Gly Pro Lys Asp Pro
        355                 360                 365

Met Ala Arg Lys Met Arg Leu Arg Arg Arg Lys Asp Ser Ala Gln Asp
370                 375                 380

Asp Gln Ala Lys Gln Val Leu Lys Gly Met Ser Asp Val Ala Gln Glu
385                 390                 395                 400

Lys Asn Lys Lys Gln Glu Glu Ser Ala Asp Ala Arg Ala Pro Ser Gly
                405                 410                 415

Lys Val Arg Arg Trp Asp Gln Gly Leu Glu Lys Pro Arg Leu Asp Tyr
            420                 425                 430

Ser Glu Phe Phe Thr Glu Asp Val Gly Gln Leu Pro Gly Leu Thr Ile
            435                 440                 445

Trp Gln Ile Glu Asn Phe Val Pro Val Leu Val Glu Glu Ala Phe His
450                 455                 460

Gly Lys Phe Tyr Glu Ala Asp Cys Tyr Ile Val Leu Lys Thr Phe Leu
465                 470                 475                 480

Asp Asp Ser Gly Ser Leu Asn Trp Glu Ile Tyr Tyr Trp Ile Gly Gly
                485                 490                 495

Glu Ala Thr Leu Asp Lys Lys Ala Cys Ser Ala Ile His Ala Val Asn
            500                 505                 510

Leu Arg Asn Tyr Leu Gly Ala Glu Cys Arg Thr Val Arg Glu Glu Met
        515                 520                 525

Gly Asp Glu Ser Glu Glu Phe Leu Gln Val Phe Asp Asn Asp Ile Ser
    530                 535                 540

Tyr Ile Glu Gly Gly Thr Ala Ser Gly Phe Tyr Thr Val Glu Asp Thr
545                 550                 555                 560

His Tyr Val Thr Arg Met Tyr Arg Val Tyr Gly Lys Lys Asn Ile Lys
                565                 570                 575

Leu Glu Pro Val Pro Leu Lys Gly Thr Ser Leu Asp Pro Arg Phe Val
            580                 585                 590

Phe Leu Leu Asp Arg Gly Leu Asp Ile Tyr Val Trp Arg Gly Ala Gln
        595                 600                 605

Ala Thr Leu Ser Ser Thr Thr Lys Ala Arg Leu Phe Ala Glu Lys Ile
    610                 615                 620

Asn Lys Asn Glu Arg Lys Gly Lys Ala Glu Ile Thr Leu Leu Val Gln
625                 630                 635                 640
```

-continued

Gly Gln Glu Leu Pro Glu Phe Trp Glu Ala Leu Gly Glu Pro Ser
            645                 650                 655

Glu Ile Lys Lys His Val Pro Glu Asp Phe Trp Pro Gln Pro Lys
            660                 665                 670

Leu Tyr Lys Val Gly Leu Gly Leu Gly Tyr Leu Glu Leu Pro Gln Ile
            675                 680                 685

Asn Tyr Lys Leu Ser Val Glu His Lys Gln Arg Pro Lys Val Glu Leu
            690                 695                 700

Met Pro Arg Met Arg Leu Leu Gln Ser Leu Leu Asp Thr Arg Cys Val
705                     710                 715                 720

Tyr Ile Leu Asp Cys Trp Ser Asp Val Phe Ile Trp Leu Gly Arg Lys
                    725                 730                 735

Ser Pro Arg Leu Val Arg Ala Ala Leu Lys Leu Gly Gln Glu Leu
            740                 745                 750

Cys Gly Met Leu His Arg Pro Arg His Ala Thr Val Ser Arg Ser Leu
            755                 760                 765

Glu Gly Thr Glu Ala Gln Val Phe Lys Ala Lys Phe Lys Asn Trp Asp
            770                 775                 780

Asp Val Leu Thr Val Asp Tyr Thr Arg Asn Ala Glu Ala Val Leu Gln
785                     790                 795                 800

Ser Pro Gly Leu Ser Gly Lys Val Lys Arg Asp Ala Glu Lys Lys Asp
            805                 810                 815

Gln Met Lys Ala Asp Leu Thr Ala Leu Phe Leu Pro Arg Gln Pro Pro
            820                 825                 830

Met Ser Leu Ala Glu Ala Glu Gln Leu Met Glu Glu Trp Asn Glu Asp
            835                 840                 845

Leu Asp Gly Met Glu Gly Phe Val Leu Glu Gly Lys Lys Phe Ala Arg
            850                 855                 860

Leu Pro Glu Glu Glu Phe Gly His Phe Tyr Thr Gln Asp Cys Tyr Val
865                     870                 875                 880

Phe Leu Cys Arg Tyr Trp Val Pro Val Glu Tyr Glu Glu Glu Lys
                    885                 890                 895

Lys Glu Asp Lys Glu Glu Lys Ala Glu Gly Lys Glu Gly Glu Ala
            900                 905                 910

Thr Ala Glu Ala Glu Glu Lys Gln Pro Glu Glu Asp Phe Gln Cys Ile
            915                 920                 925

Val Tyr Phe Trp Gln Gly Arg Glu Ala Ser Asn Met Gly Trp Leu Thr
            930                 935                 940

Phe Thr Phe Ser Leu Gln Lys Lys Phe Glu Ser Leu Phe Pro Gly Lys
945                     950                 955                 960

Leu Glu Val Val Arg Met Thr Gln Gln Gln Glu Asn Pro Lys Phe Leu
            965                 970                 975

Ser His Phe Lys Arg Lys Phe Ile Ile His Arg Gly Lys Arg Lys Ala
            980                 985                 990

Val Gln Gly Ala Gln Gln Pro Ser Leu Tyr Gln Ile Arg Thr Asn Gly
            995                 1000                1005

Ser Ala Leu Cys Thr Arg Cys Ile Gln Ile Asn Thr Asp Ser Ser
            1010                1015                1020

Leu Leu Asn Ser Glu Phe Cys Phe Ile Leu Lys Val Pro Phe Glu
            1025                1030                1035

Ser Glu Asp Asn Gln Gly Ile Val Tyr Ala Trp Val Gly Arg Ala
            1040                1045                1050

| | | | | | | | | | |
|---|---|---|---|---|---|---|---|---|---|
| Ser | Asp | Pro | Asp | Glu | Ala | Lys | Leu | Ala | Glu | Asp | Ile | Leu | Asn | Thr |

Ser Asp Pro Asp Glu Ala Lys Leu Ala Glu Asp Ile Leu Asn Thr
1055              1060              1065

Met Phe Asp Thr Ser Tyr Ser Lys Gln Val Ile Asn Glu Gly Glu
1070              1075              1080

Glu Pro Glu Asn Phe Phe Trp Val Gly Ile Gly Ala Gln Lys Pro
1085              1090              1095

Tyr Asp Asp Asp Ala Glu Tyr Met Lys His Thr Arg Leu Phe Arg
1100              1105              1110

Cys Ser Asn Glu Lys Gly Tyr Phe Ala Val Thr Glu Lys Cys Ser
1115              1120              1125

Asp Phe Cys Gln Asp Leu Ala Asp Asp Ile Met Leu Leu
1130              1135              1140

Asp Asn Gly Gln Glu Val Tyr Met Trp Val Gly Thr Gln Thr Ser
1145              1150              1155

Gln Val Glu Ile Lys Leu Ser Leu Lys Ala Cys Gln Val Tyr Ile
1160              1165              1170

Gln His Met Arg Ser Lys Glu His Glu Arg Pro Arg Arg Leu Arg
1175              1180              1185

Leu Val Arg Lys Gly Asn Glu Gln His Ala Phe Thr Arg Cys Phe
1190              1195              1200

His Ala Trp Ser Ala Phe Cys Lys Ala Leu Ala
1205              1210

<210> SEQ ID NO 7
<211> LENGTH: 1686
<212> TYPE: DNA
<213> ORGANISM: Homo sapiens

<400> SEQUENCE: 7

```
cagacgctcc ctcagcaagg acagcagagg accagctaag agggagagaa gcaactacag      60
accccccctg aaaacaaccc tcagacgcca catcccctga caagctgcca ggcaggttct     120
cttcctctca catactgacc cacggctcca ccctctctcc cctggaaagg acaccatgag     180
cactgaaagc atgatccggg acgtggagct ggccgaggag gcgctcccca agaagacagg     240
gggcccccag ggctccaggc ggtgcttgtt cctcagcctc ttctccttcc tgatcgtggc     300
aggcgccacc acgctcttct gcctgctgca ctttggagtg atcggccccc agagggaaga     360
gttccccagg gacctctctc taatcagccc tctggcccag gcagtcagat catcttctcg     420
aaccccgagt gacaagcctg tagcccatgt tgtagcaaac cctcaagctg aggggcagct     480
ccagtggctg aaccgccggg ccaatgccct cctggccaat ggcgtggagc tgagagataa     540
ccagctggtg gtgccatcag agggcctgta cctcatctac tcccaggtcc tcttcaaggg     600
ccaaggctgc ccctccaccc atgtgctcct cacccacacc atcagccgca tcgccgtctc     660
ctaccagacc aaggtcaacc tcctctctgc catcaagagc cctgccaga gggagacccc      720
agaggggct gaggccaagc cctggtatga gcccatctat ctgggagggg tcttccagct     780
ggagaagggt gaccgactca gcgctgagat caatcggccc gactatctcg actttgccga     840
gtctgggcag gtctactttg gatcattgc cctgtgagga ggacgaacat ccaaccttcc     900
caaacgcctc ccctgcccca atccctttat tacccctcc ttcagacacc ctcaacctct     960
tctggctcaa aaagagaatt gggggcttag ggtcggaacc caagcttaga actttaagca    1020
acaagaccac cacttcgaaa cctgggattc aggaatgtgt ggcctgcaca gtgaagtgct    1080
ggcaaccact aagaattcaa actggggcct ccagaactca ctggggccta cagctttgat    1140
```

```
ccctgacatc tggaatctgg agaccaggga gcctttggtt ctggccagaa tgctgcagga    1200
cttgagaaga cctcacctag aaattgacac aagtggacct taggccttcc tctctccaga   1260
tgtttccaga cttccttgag acacggagcc cagccctccc catggagcca gctccctcta   1320
tttatgtttg cacttgtgat tatttattat ttatttatta tttatttatt tacagatgaa   1380
tgtatttatt tgggagaccg gggtatcctg ggggacccaa tgtaggagct gccttggctc   1440
agacatgttt tccgtgaaaa cggagctgaa cataggctg ttcccatgta gcccctggc    1500 ctctgtgcct tcttttgatt atgttttta aaatatttat ctgattaagt tgtctaaaca   1560
atgctgattt ggtgaccaac tgtcactcat tgctgagcct ctgctcccca ggggagttgt   1620
gtctgtaatc gccctactat tcagtggcga gaaataaagt ttgcttagaa agaaaaaaa    1680 aaaaaa                                                              1686
```

<210> SEQ ID NO 8
<211> LENGTH: 233
<212> TYPE: PRT
<213> ORGANISM: Homo sapiens

<400> SEQUENCE: 8

```
Met Ser Thr Glu Ser Met Ile Arg Asp Val Glu Leu Ala Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230
```

<210> SEQ ID NO 9
<211> LENGTH: 15
<212> TYPE: PRT
<213> ORGANISM: Homo sapiens

-continued

```
<400> SEQUENCE: 9

Cys Gln Lys Leu Glu His Leu Ser Val Ser His Asn Asn Leu Thr
1               5                   10                  15
```